(12) United States Patent
Zahler et al.

(10) Patent No.: US 11,573,224 B2
(45) Date of Patent: Feb. 7, 2023

(54) METHODS OF DETECTION USING X-RAY FLUORESCENCE

(71) Applicant: Icagen, LLC, San Diego, CA (US)

(72) Inventors: Nathan Zahler, Durham, NC (US); Jonathan Theile, Durham, NC (US)

(73) Assignee: ICAGEN, LLC, Emeryville, CA (US)

( * ) Notice: Subject to any disclaimer, the term of this patent is extended or adjusted under 35 U.S.C. 154(b) by 364 days.

(21) Appl. No.: 16/646,736

(22) PCT Filed: Sep. 14, 2018

(86) PCT No.: PCT/US2018/051025
§ 371 (c)(1),
(2) Date: Mar. 12, 2020

(87) PCT Pub. No.: WO2019/055754
PCT Pub. Date: Mar. 21, 2019

(65) Prior Publication Data
US 2020/0278346 A1    Sep. 3, 2020

Related U.S. Application Data

(60) Provisional application No. 62/558,528, filed on Sep. 14, 2017.

(51) Int. Cl.
*G01N 23/223* (2006.01)
*G01N 33/543* (2006.01)

(52) U.S. Cl.
CPC ..... *G01N 33/54313* (2013.01); *G01N 23/223* (2013.01); *G01N 2223/0766* (2013.01)

(58) Field of Classification Search
CPC ........... G01N 33/543; G01N 33/54313; G01N 33/54373; G01N 23/223; G01N 2223/0766; B01D 15/3828
See application file for complete search history.

(56) References Cited

U.S. PATENT DOCUMENTS

| | | |
|---|---|---|
| 7,858,385 B2 | 12/2010 | Warner et al. |
| 9,465,036 B2 | 10/2016 | Winnik et al. |
| 2012/0028273 A1 | 2/2012 | Straume et al. |
| 2016/0341678 A1 | 11/2016 | Peterson et al. |

FOREIGN PATENT DOCUMENTS

WO    WO 2017/184564 A1    10/2017

OTHER PUBLICATIONS

International Search Report & Written Opinion, PCT Application No. PCT/US18/51025, dated Jan. 4, 2019, 13 pages.

*Primary Examiner* — Jurie Yun
(74) *Attorney, Agent, or Firm* — Knobbe, Martens, Olson & Bear LLP

(57) ABSTRACT

The present invention relates, in part, to methods of using X-ray fluorescence (XRF) spectrometry for analyzing (e.g., measuring) the binding of a soluble target to an insoluble material.

26 Claims, 3 Drawing Sheets

Specification includes a Sequence Listing.

SEQUENCE LISTING

```
<160> NUMBER OF SEQ ID NOS: 16

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)
<220> FEATURE:
<221> NAME/KEY: 4-bromophenylalanine
<222> LOCATION: (10)..(10)

<400> SEQUENCE: 1

Phe Cys Asp Ile Cys Pro Asn His Cys Phe
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)
<220> FEATURE:
<221> NAME/KEY: 4-bromophenylalanine
<222> LOCATION: (10)..(10)

<400> SEQUENCE: 2

Phe Cys Gln Arg Cys Glu Arg Trp Cys Phe
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)
<220> FEATURE:
<221> NAME/KEY: 4-bromophenylalanine
<222> LOCATION: (10)..(10)

<400> SEQUENCE: 3

Phe Cys Phe His Cys Phe Ser Glu Cys Phe
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
```

```
<222> LOCATION: (1)..(1)
<220> FEATURE:
<221> NAME/KEY: 4-bromophenylalanine
<222> LOCATION: (10)..(10)

<400> SEQUENCE: 4

Phe Cys Ala Gly Cys Phe Thr Gly Cys Phe
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)
<220> FEATURE:
<221> NAME/KEY: 4-bromophenylalanine
<222> LOCATION: (10)..(10)

<400> SEQUENCE: 5

Phe Cys Gln Leu Cys Asn Val Leu Cys Phe
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)

<400> SEQUENCE: 6

Phe Cys Asp Ile Cys Pro Asn His Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)

<400> SEQUENCE: 7

Phe Cys Gln Arg Cys Glu Arg Trp Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)

<400> SEQUENCE: 8

Phe Cys His Thr Cys Phe Gln Thr Cys
1               5

<210> SEQ ID NO 9
```

```
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: 3,5-dibromotyrosine
<222> LOCATION: (1)..(1)
<220> FEATURE:
<221> NAME/KEY: MISC_FEATURE
<222> LOCATION: (4)..(4)
<223> OTHER INFORMATION: Xaa can be Glutamine (Q) or Threonine (T)

<400> SEQUENCE: 9

Tyr Cys Arg Xaa Ser Cys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: 3,5-dibromotyrosine
<222> LOCATION: (1)..(1)

<400> SEQUENCE: 10

Tyr Cys Arg Thr Ser Cys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: 3,5-dibromotyrosine
<222> LOCATION: (1)..(1)

<400> SEQUENCE: 11

Tyr Cys Arg Gln Ser Cys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: mono-iodo tyrosine
<222> LOCATION: (1)..(1)
<220> FEATURE:
<221> NAME/KEY: MISC_FEATURE
<222> LOCATION: (4)..(4)
<223> OTHER INFORMATION: Xaa can be Glutamine (Q) or Threonine (T)

<400> SEQUENCE: 12

Tyr Cys Arg Xaa Ser Cys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: mono-iodo tyrosine
```

```
-continued

<222> LOCATION: (1)..(1)

<400> SEQUENCE: 13

Tyr Cys Arg Thr Ser Cys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: mono-iodo tyrosine
<222> LOCATION: (1)..(1)

<400> SEQUENCE: 14

Tyr Cys Arg Gln Ser Cys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 15

Cys Arg Thr Ser Cys
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 16

Cys Arg Gln Ser Cys
1               5
```

METHODS OF DETECTION USING X-RAY FLUORESCENCE

CROSS-REFERENCE TO RELATED APPLICATIONS

This application claims the benefit of U.S. Provisional Patent Application No. 62/558,528, filed Sep. 14, 2017, the entire contents of which are herein incorporated by reference.

TECHNICAL FIELD

The present invention relates, in part, to methods of using X-ray fluorescence (XRF) spectrometry for analyzing (e.g., measuring) the binding of a soluble target to an insoluble material.

BACKGROUND

XRF spectrometry is a powerful spectroscopic technique commonly used for elemental analysis and chemical analysis. During XRF analysis, a sample is irradiated with X-rays emitted from an X-ray source, and fluorescent X-rays, which are characteristic X-rays released from the sample, are detected by an X-ray detector. A spectrum is obtained from the energy of the detected X-rays, and the sample is qualitatively or quantitatively analyzed.

More recently, XRF has been employed for quantifying molecular binding. However, the process requires separation of unbound analytes from the bound complexes. Further, the technique is not conducive to high-throughput screening of a large number of soluble test materials, or testing of a large number of solution conditions, as is required for measurements of equilibrium binding constants.

Accordingly, improved XRF methods are needed for applications that require high-throughput screening and analysis of a large number of samples.

SUMMARY

In various aspects and embodiments, the present invention provides compositions and methods for analyzing (e.g., measuring) the binding of a soluble target to an insoluble material. In various embodiments, the present methods comprise providing a first solution comprising a soluble target. An insoluble material is then exposed to the first solution to allow the formation of a complex comprising the soluble target and the insoluble material. Subsequently, the first solution comprising unbound soluble target is removed, while the insoluble test material (comprising bound soluble target) is retained. The retained insoluble test material is resuspended in a second solution containing at least one non-volatile component and then dried in a multi-well plate. The present methods further comprise measuring the amount of soluble target bound to the insoluble material using XRF.

In various embodiments, the compositions and methods of the invention are amenable to high-throughput and/or multiplexing formats. In various embodiments, the present methods allow for multiple parallel runs in which the identity or the concentration of the soluble target is varied. In various embodiments, the present methods also allow for multiple parallel runs in which the identity or amount of the insoluble material is varied.

In various embodiments, the present invention provides compositions and methods for detection of a soluble target, such as an inorganic ion or inorganic compound, an organic ion or organic compound, and a biological molecule such as a protein, cofactor, nucleotide, and nucleic acid. Accordingly, in various embodiments, the present invention relates to methods for drug discovery.

DETAILED DESCRIPTION

The present invention provides improved methods for measuring the binding of a soluble target to an insoluble material using XRF. Methods of the invention provides various advantages, including being able to be performed in a high-throughput format. More particularly, the present methods allow for multiple parallel runs thereby making possible the simultaneous testing of multiple binding conditions.

Methods

In various embodiments, the present invention provides methods for analyzing (e.g., measuring) the binding of a soluble target to an insoluble material. The present methods also allow for an analysis of a modulator that modulates the binding of the soluble target to the insoluble material. Methods of the invention further comprise using an XRF spectrometer to obtain spectral features associated with binding of the soluble target to the insoluble material.

Figure 1:
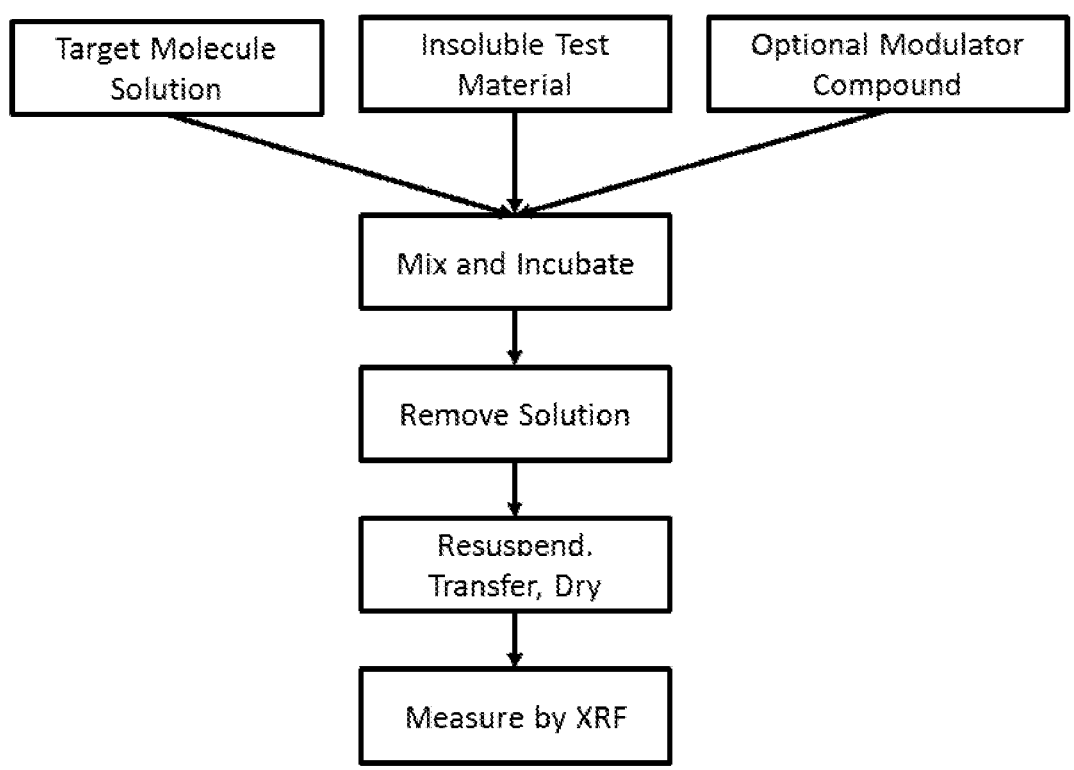
FIG. 1 provides a schematic illustration of an illustrative method of the invention.

Specifically, in various embodiments, the present methods involves equilibrating the soluble target with the insoluble material, which requires the combination of the target and the insoluble material in solution, and incubation of the target and the insoluble material in solution for sufficient time to ensure that chemical equilibrium is obtained; separating the unbound/excess target in a manner that does not unacceptably perturb the binding, and assaying the insoluble material for the bound target. A schematic representation of an illustrative method of the invention is provided in FIG. 1.

In various embodiments, the present methods comprise providing a first solution comprising a soluble target. An insoluble material is then exposed to the first solution to allow the formation of a complex comprising the soluble target and the insoluble material. Subsequently, the first solution comprising unbound soluble target is removed, while the insoluble test material (comprising bound soluble target) is retained. The retained insoluble test material is resuspended in a second solution containing at least one non-volatile component and then dried in a multi-well plate. The present methods further comprise measuring in the sample the amount of soluble target bound to the insoluble material using XRF.

In various embodiments, the present methods allow for multiple parallel runs in which the identity or amount of the insoluble material can be varied. In various embodiments, the present methods also allow for multiple parallel runs in which the identity or the concentration of the soluble target can be varied.

In various embodiments, the present method comprises providing a first solution comprising a soluble target. In some embodiments, the method allows for an analysis of the binding activity of a soluble target which comprises a chemical element having an atomic number of about 9 or higher. In some embodiments, the chemical element is a heavy element having an atomic number of about 9, about 10, about 11, about 12, about 13, about 14, about 15, about 16, about 17, about 18, about 19, or higher. In illustrative embodiments, the chemical element is sulfur, phosphorus, silicon, potassium, calcium, manganese, iron, cobalt, nickel, copper, zinc, arsenic, rhodium, molybdenum, chromium, selenium, bromine, silver, cadmium, platinum, gold, mercury, lead, gadolinium, dysprosium, terbium, europium, strontium, cesium, barium, or iodine.

In some embodiments, the soluble target is selected from, but not limited to, an inorganic ion or inorganic compound, an organic ion or organic compound, salts, metal ions, or a biological molecule such as a protein, cofactor, nucleotide, or nucleic acid. In an embodiment, the soluble target is an inorganic ion. Illustrative soluble targets that may be tested using the methods of the invention are provided in US Patent Publication No. 2015/0309021, the entire disclosure is hereby incorporated by reference. For example, illustrative soluble targets include, but are not limited to, one or more of Lithium, Beryllium, Boron, Sodium, Magnesium, Aluminum, Silicon, Potassium, Calcium, Scandium, Titanium, Vanadium, Chromium, Manganese, Iron, Cobalt, Nickel, Copper, Zinc, Gallium, Germanium, Arsenic, Rubidium, Strontium, Yttrium, Zirconium, Niobium, Molybdenum, Technetium, Ruthenium, Rhodium, Palladium, Silver, Cadmium, Indium, Tin, Antimony, Tellurium, Cesium, Barium, Lanthanum, Cerium, Praseodymium, Neodymium, Promethium, Samarium, Europium, Gadolinium, Terbium, Dysprosium, Holmium, Erbium, Thulium, Ytterbium, Lutetium, Hafnium, Tantalum, Tungsten, Rhenium, Osmium, Iridium, Platinum, Gold, Mercury, Thallium, Lead, Bismuth, Francium, Radium, Actinium, Thorium, Protactinium, Uranium, Neptunium, Plutonium, Americium, Curium, Berkelium, Californium, Einsteinium, Fermium, Mendelevium, Nobelium, Lawrencium, Rutherfordium, Dubnium, Seaborgium, Bohrium, Hassium, Meitnerium, Darmstadtium, Roentgenium, Copernicium, Ununtrium, Flerovium, Ununpentium, and Livermorium; Chlorpheniramine; Methimazole; Nelfinavir; Zonisamide; Naltrexone; Carmustine; Ifosfamide; Rizatriptan; Ramipril; Milrinone; Tenoxicam; Apraclonidine; Neomycin; Gabapentin; Anastrozole; Alitretinoin; Oxytetracycline; Prazosin; Amifostine; Desipramine; Hydroxyurea; Naloxone; Kanamycin; Candoxatril; Tramadol; Chlorpropamide; Oxaprozin; Trichlormethiazide; Sulpiride; Cyproheptadine; Brimonidine; Tamsulosin; Misoprostol; Pentolinium; Donepezil; Itraconazole; Penciclovir; Bicalutamide; Epinastine; Trimethaphan; R-mephobarbital; Clavulanate; Nitrofurazone; Bethanechol; Losartan; Gemifloxacin; Clonazepam; Atorvastatin; Heparin; Methohexital; Efavirenz; Duloxetine; Cyclizine; Methoxamine; Benazepril; Amsacrine; Fluticasone Propionate; Divalproex; Etodolac; Enoxaparin; Indinavir; Trihexyphenidyl; Tadalafil; Progabide; Pantoprazole; Meperidine; Guanfacine; Sulfamethoxazole; Lansoprazole; Porfimer; Triamterene; Cocaine; Ribavirin; Theophylline; Vitamin C; Dopamine; Minoxidil; Nicardipine; Phenacemide; Dexrazoxane; Carvedilol; Hydrochlorothiazide; Phentermine; Rifabutin; Zolpidem; Tegaserod; Orphenadrine; Digoxin; Phenelzine; Aprepitant; Vinorelbine; Cerivastatin; Trimethoprim; Simvastatin; Argatroban; Norgestrel; Perhexiline; Pefloxacin; Indomethacin; Levobupivacaine; Rescinnamine; Dicyclomine; Bexarotene; Chlorambucil; Lorazepam; Hesperetin; Melphalan; Acetazolamide; Codeine; Pentoxifylline; Dobutamine; Tamoxifen; Dactinomycin; Venlafaxine; Idarubicin; Chlorthalidone; Tizanidine; Flecainide; Uracil Mustard; Dichlorphenamide; Adenosine; Valsartan; Nandrolone Phenpropionate; Ouabain; Quinidine; Methacycline; Olanzapine; Isotretinoin; Balsalazide; Amoxapine; Vitamin D4 (Dihydrotachysterol); Exemestane; Riluzole; Tolterodine; Citalopram; Cidofovir; Delavirdine; Nilutamide; Rofecoxib; Sulfasalazine; Nitroglycerin; Thiamylal; Cilostazol; Pramipexole; Methoxsalen; Oxymorphone; Succinylcholine; Carbidopa; Mupirocin; Remikiren; Captopril; Levobunolol; Phenindione; Probenecid; Solifenacin succinate; Almotriptan; Tolazoline; Arsenic Trioxide; Atenolol; Trifluoperazine; Clonidine; Sertraline; Tubocurarine; Propantheline; Sirolimus; Prilocaine; Clarithromycin; Isoproterenol; Valdecoxib; Phenobarbitone; Doxorubicin; Oxaliplatin; Risperidone; Proguanil; Oxyphenonium; Sulfadiazine; Nitrofurantoin; Lercanidipine; Propranolol; Carteolol; Cefadroxil; Prednisolone; Reboxetine; Caspofungin; Nicotine; Gemcitabine; Pentostatin; Capecitabine; Vitamin B6 (Pyridoxine); Leflunomide; Galantamine; Rifampin; Metoprolol; Streptozocin; Metaproterenol; Crotamiton; Isoflurane; Cyclobenzaprine; Gentamicin; Morphine; Abacavir; Torasemide; Pimozide; Sevoflurane; Naratriptan; Memantine; Buspirone; Olmesartan Medoxomil; Cevimeline; Piperazine; Emtricitabine; Amitriptyline; Phenprocoumon; Timolol; Suprofen; Ibandronate; Netilmicin; Glyburide; Enflurane; Levothyroxine; Paramethadione; Topiramate; Etoposide; Didanosine; Phenytoin; Mexiletine; Cefaclor; Clotrimazole; Betaxolol; Calcitriol; Bupivacaine; Amoxicillin; Mechlorethamine; Cephalexin; Ethacrynic acid; Acetaminophen; Clomipramine; Ranitidine; Orlistat; Valproic Acid; Bisoprolol; Trimeprazine; Paclitaxel; Cladribine; Propafenone; Phenmetrazine; Ganciclovir; Aspirin; Zileuton; Butalbital; Tolbutamide; Trimetrexate; Picrotoxin; Frovatriptan; Ridogrel; Demeclocycline; Enprofylline; Loperamide; Tacrolimus; Salmeterol; Clofazimine; Alprazolam; Moxifloxacin; Vigabatrin; Mitomycin; Cefuroxime; Tridihexethyl; Tropicamide; Amiodarone; Mometasone; Thioguanine; Lomustine; Gemfibrozil; Bumetanide; Torsemide; Famotidine; Propylthiouracil; Isradipine; Flucytosine; Mefloquine; Nadolol; Ropinirole; Pentamidine; Tirofiban; Sertaconazole; Triprolidine; Clobazam; Chlorzoxazone; Levodopa; Olopatadine; Estradiol; Ritonavir; Triazolam; Methscopolamine; Trimethadione; Remoxipride; Quinacrine; Ethosuximide; Fenfluramine; Ampicillin; Rivastigmine; Thiethylperazine; Desloratadine; Piperacillin; Vitamin B12; Fluconazole; Pravastatin; Aminophylline; Dacarbazine; Cinnarizine; Vidarabine; Verapamil; Cromolyn; Carbamazepine; Propiomazine; Prednisone; Warfarin; Methylprednisolone; Clomocycline; Tiagabine; Dapsone; Fluvastatin; Fentanyl; Fexofenadine; Palonosetron; Methotrexate; Meclizine; Zopiclone; Promazine; Cisplatin; Dipyridamole; Epirubicin; Tretinoin; Esomeprazole; Paroxetine; Phenylephrine; Diphenoxylate; Dofetilide; Acrosoxacin; Lovastatin; Mitoxantrone; Ibuprofen; Celecoxib; Felodipine; Zolmitriptan; Zafirlukast; Zanamivir; Sumatriptan; Pyridostigmine; Glimepiride; Pilocarpine; Procyclidine; Loratadine; Dutasteride; Mequitazine; Oxycodone; Flupenthixol; Toremifene; Vindesine; Trospium; Pemirolast; Ceftriaxone; Conjugated Estrogens; Azithromycin; Doxepin; Oxyphencyclimine; Raloxifene; Ketoconazole; Nefazodone; Rosiglitazone;

Chloroprocaine; Fenofibrate; Physostigmine; Cyclophosphamide; Phenylbutazone; Risedronate; Zaleplon; Streptomycin; Irbesartan; Entacapone; Carisoprodol; Domperidone; Halofantrine; Candesartan; Nitrendipine; Triamcinolone; Penicillin V; Ciprofloxacin; Fluvoxamine; Vitamin D2 (Ergocalciferol); Oxybutynin; Calcidiol; Perphenazine; Raltitrexed; Eszopiclone; Mifepristone; Testosterone; Montelukast; Allopurinol; Glipizide; Sulfanilamide; Repaglinide; Stavudine; Protriptyline; Budesonide; Omapatrilat; Clopidogrel; Tolcapone; Omeprazole; Zidovudine; Epinephrine; Sulfacetamide; Bleomycin; Cisapride; Isosorbide Dinitrate; Sibutramine; Phenylpropanolamine; Mecamylamine; Gliclazide; Cefprozil; Acetophenazine; Methysergide; Phytonadione; Triflupromazine; Carboplatin; Chloroquine; Norfloxacin; Clozapine; Reserpine; Diltiazem; Doxazosin; Brinzolamide; Dihydroergotamine; Levofloxacin; Lidocaine; Amphetamine; Ondansetron; Chlorpromazine; Telithromycin; Methadone; VitaminA; Guanabenz; Troglitazone; Alfuzosin; Sulfapyridine; Ropivacaine; Ketamine; Mitotane; Vincristine; Phensuximide; Secobarbital; Trimipramine; Cytarabine; Fondaparinux; Ofloxacin; Carbimazole; Idoxuridine; Felbamate; Vitamin D3 (Cholecalciferol); Disopyramide; Terbinafine; Procainamide; Enalapril; Phenformin; Mephenytoin; Betamethasone; Metaxalone; Pirenzepine; Fluorouracil; Sulfametopyrazine; Dolasetron; Amlodipine; Daunorubicin; Proparacaine; Quinapril; Selegiline; Fosinopril; Diclofenac; Isosorbide Mononitrate; Meloxicam; Fluoxetine; Apomorphine; Trazodone; Modafinil; Proflavine; Vitamin B3 (Niacin); Ipratropium; Haloperidol; Benzocaine; Ziprasidone; Ritodrine; Voriconazole; Chlorhexidine; Rosuvastatin; Minocycline; Propoxyphene; Primidone; Amikacin; Baclofen; Vitamin BI (Thiamine); Albuterol; Metaraminol; Sildenafil; Temozolomide; Nitazoxanide; Marimastat; Lisinopril; Alendronate; Zalcitabine; Quinine; Beclomethasone; Lymecycline; Clindamycin; Acyclovir; Cimetidine; Norgestimate; Lamotrigine; Marinol; Tetracycline; Pemetrexed; Loxapine; Sotradecol; Dorzolamide; Dexmedetomidine; Irinotecan; Alosetron; Tobramycin; Cefixime; Astemizole; Diphenhydramine; Estrone; Terbutaline; Nifedipine; Hydrocodone; Aminoglutethimide; Nateglinide; Fludarabine; Sulfisoxazole; Thioridazine; Doxycycline; Halothane; Pyrimethamine; Famciclovir; Promethazine; Nortriptyline; Moclobemide; Primaquine; Amprenavir; Terfenadine; Hyoscyamine; Furosemide; Flucloxacillin; Mesoridazine; Nimodipine; Encainide; Atomoxetine; Phentolamine; Scopolamine; Nicergoline; Framycetin; Ezetimibe; Sulfinpyrazone; Bupropion; Bromocriptine; Saquinavir; Prochlorperazine; Estramustine; Vitamin B2 (Riboflavin); Medroxyprogesterone; Papaverine; Benzonatate; Cetirizine; Metronidazole; Finasteride; Fluphenazine; Pseudoephedrine; Nisoldipine; Lisuride; Cinalukast; Aripiprazole; Clodronate; Testolactone; Formoterol; Diazepam; Cefdinir; Tranylcypromine; Penicillin G; Mimosine; Dexfenfluramine; Teniposide; Procaine; Phenoxybenzamine; Altretamine; Pioglitazone; Fulvestrant; Dextromethorphan; Acarbose; Methylphenidate; Terconazole; Thiopental; Acamprosate; Valrubicin; Pergolide; Busulfan; Metoclopramide; Bendroflumethiazide; Terazosin; Metipranolol; Foscarnet; Buprenorphine; Sufentanil; Imipramine; Caffeine; Dexamethasone; Quetiapine; Temazepam; Ergotamine; Pindolol; Norethindrone; Midazolam; Lamivudine; Chlordiazepoxide; Escitalopram; Sulfamethizole; Mirtazapine; Cetrorelix; Topotecan; Hydroxyzine; Tripelennamine; Tacrine; Ethinyl Estradiol; Floxuridine; Pipobroman; Novobiocin; Procarbazine; Decamethonium; Valacyclovir; Leucovorin; Vardenafil; Progesterone; Isocarboxazid; Cerulenin; Sulfoxone; Nevirapine; Nizatidine; Eplerenone; Vinblastine; Desoxycorticosterone Pivalate; Bromodiphenhydramine; Ergoloid Mesylate; Gallamine Triethiodide; Methdilazine; Betazole; Chlorotrianisene; Chlorprothixene; Diphenylpyraline; Chlorothiazide; Hexachlorophene; Buclizine; Adinazolam; Biperiden; Alfentanil; Bepridil; Benzthiazide; Ethopropazine; Mefenamic acid; Cycrimine; Ethoxzolamide; Levallorphan; Methyprylon; Minaprine; Alprenolol; Clidinium; Ethanol; Methylergonovine; Methazolamide; Anileridine; Melatonin; Methoxyflurane; Levomethadyl Acetate; Maprotiline; Benztropine; Aminosalicylic Acid; Isoetharine; Methantheline; Butabarbital; Flurbiprofen; L-Norgestrel; Fludrocortisone; Metharbital; Benzphetamine; Ethynodiol Diacetate; Dicumarol; Desogestrel; Isoflurophate; Levorphanol; Carbinoxamine; Etonogestrel; Disulfiram; Dyphylline; Dexbrompheniramine; Ambenonium; Acebutolol; Acetohexamide; Acetohydroxamic Acid; Acitretin; Adapalene; Adefovir Dipivoxil; Albendazole; Alclometasone; Alprostadil; Alseroxylon; Amantadine; Amcinonide; Amdinocillin; Amiloride; Aminocaproic Acid; Aminohippurate; Aminolevulinic Acid; Amlexanox; Amodiaquine; Amphotericin B; Anagrelide; Anisindione; Anisotropine Methylbromide; Arbutamine; Ardeparin; Atazanavir; Atovaquone; Atracurium; Atropine; Auranofin; Azacitidine; Azatadine; Azathioprine; Azelaic Acid; Azelastine; Azlocillin; Aztreonam; Bacitracin; Oxybuprocaine; Bentiromide; Bentoquatam; Benzquinamide; Benzyl Benzoate; Benzylpenicilloyl Polylysine; Betanidine; Bimatoprost; Bitolterol Mesylate; Bortezomib; Bosentan; Bretylium; Bromfenac; Brompheniramine; Butenafine; Butoconazole; Butorphanol Tartrate; Cabergoline; Calcium Acetate; Calcium Chloride; Calcium Gluceptate; Candicidin; Capreomycin; Carbachol; Carbenicillin; Carboprost Tromethamine; Carphenazine; Carprofen; Cefditoren Pivoxil; Cefmenoxime; Cefmetazole; Ceforanide; Cefotaxime; Cefotiam; Cefpiramide; Ceftazidime; Cephaloglycin; Cephalothin; Cephapirin; Ceruletide; Chloramphenicol; Chlormerodrin; Chlormezanone; Chloroxine; Chlorphenesin; Ciclopirox; Cinacalcet; Cinoxacin; Cisatracurium Besylate; Clemastine; Clobetasol; Clocortolone; Clofarabine; Clofibrate; Clomifene; Clorazepate; Cloxacillin; Colesevelam; Colestipol; Colistimethate; Colistin; Cryptenamine; Cyclacillin; Cyclopentolate; Cycloserine; Cyclothiazide; Cysteamine Bitartrate; Dantrolene; Dapiprazole; Darifenacin; Deferoxamine; Demecarium bromide; Deserpidine; Desflurane; Deslanoside; Desoximetasone; Dextrothyroxine; Dezocine; Diatrizoate; Diazoxide; Dibucaine; Dicloxacillin; Dienestrol; Diethylcarbamazine; Diethyipropion; Diethylstilbestrol; Diflorasone; Diflunisal; Dimenhydrinate; Dimethyl Sulfoxide; Dinoprost Tromethamine; Dinoprostone; Diphemanil Methylsulfate; Diphenidol; Dipivefrin; Dirithromycin; Docetaxel; Docosanol; Doxacurium Chloride; Doxapram; Doxylamine; Dromostanolone; Droperidol; Dyclonine; Dydrogesterone; Echothiophate Iodide; Econazole; Edrophonium; Eletriptan; Emedastine; Enoxacin; Entecavir; Epoprostenol; Eprosartan; Erlotinib; Ertapenem; Erythromycin; Esmolol; Estazolam; Ethambutol; Ethchlorvynol; Ethinamate; Ethiodol; Ethionamide; Ethotoin; Etidronate; Etomidate; Etretinate; Fenoldopam; Fenoprofen; Flavoxate; Flumazenil; Flumethasone Pivalate; Flunisolide; Fluocinolone Acetonide; Fluocinonide; Fluorescein; Fluorometholone; Fluoxymesterone; Flurandrenolide; Flurazepam; Flutamide; Fomepizole; Fomivirsen; Fosfomycin; Furazolidone; Gadobenate dimeglumine; Gadodiamide; Gadopentetate dimeglumine; Gadoteridol; Gadoversetamide; Galsulfase; Ganirelix; Gatifloxacin; Gefitinib; Gentian Violet; Glatiramer Acetate; Glycopyrrolate; Gonadorelin; Granisetron; Grepafloxacin; Griseofulvin; Guaifenesin; Guanadrel Sulfate; Guanethidine; Guanidine; Halazepam; Halobetasol Propionate; Haloprogin; Hetacillin; Hexafluorenium Bromide; Hexylcaine; Histamine Phosphate; Homatropine Methylbromide; Hydrocortamate; Hydrocortisone; Hydroflumethiazide; Hydromorphone; Hydroxocobalamin; Hydroxypropyl Cellulose; Hydroxystilbamidine Isethionate; Ibutilide Fumarate; Icodextrin; Iloprost; Imatinib; Imiquimod; Indapamide; Indecainide; Inulin; Iron Dextran; Isoniazid; Ivermectin; Ketoprofen; Ketorolac; Ketotifen Fumarate; Labetalol; Lactulose; Latanoprost; Letrozole; Levamisole; Levetiracetam; Levocabastine; Levocarnitine; Lindane; Linezolid; Liothyronine; Lomefloxacin; Loracarbef; Loteprednol Etabonate; Magnesium Sulfate; Malathion; Mannitol; Masoprocol; Mazindol; Mebendazole; Meclofenamate; Medrysone; Megestrol; Mepivacaine; Meprobamate; Mercaptopurine; Meropenem; Mesalamine; Metformin; Metixene; Methocarbamol; Methyclothiazide; Methyl aminolevulinate; Methyldopa; Metolazone; Metyrapone; Metyrosine; Mezlocillin; Micafungin; Miconazole; Midodrine; Miglitol; Miglustat; Mivacurium; Moexipril; Monobenzone; Moricizine; Nabilone; Nabumetone; Nafarelin; Nafcillin; Naftifine; Nalbuphine; Nalidixic Acid; Naproxen; Natamycin; Nedocromil; Nitisinone; Nitric Oxide; Nitroprusside; Nystatin; Oseltamivir Phosphate; Oxacillin; Oxarnniquine; Oxandrolone; Oxazepam; Oxiconazole Nitrate; Oxymetazoline; Pamidronate; Paricalcitol; Pemoline; Penicillamine; Pentagastrin; Pentazocine; Pentobarbital; Pentosan Polysulfate; Perflutren; Perindopril Erbumine; Pimecrolimus; Piroxicam; Podofilox; Polymyxin B Sulfate; Pralidoxime; Praziquantel; Prednicarbate; Pregabalin; Propofol; Pyrazinamide; Rabeprazole; Ramelteon; Remifentanil; Rifapentine; Rifaximin; Rimantadine; Rimexolone; Rocuronium; Sevelamer; Sotalol; Sparfloxacin; Spectinomycin; Spironolactone; Succimer; Sucralfate; Sulindac; Tazarotene; Telmisartan; Tenofovir; Thalidomide; Thiabendazole; Ticlopidine; Tiludronate; Tinidazole; Tioconazole; Tocainide; Tolazamide; Tolmetin; Trandolapril; TranexamicAcid; Travoprost; Treprostinil; Trifluridine; Trilostane; Trimethobenzamide; Trovafloxacin; Vancomycin; Verteporfin; Zoledronate; Levosimendan; Tetrahydrobiopterin; Lubiprostone; Dornase alfa (Dnase); Alpha-1-proteinase inhibitor; Cyclosporine; Infliximab; Muromonab; Coagulation factor Vila; Daclizumab; Laronidase; Leuprolide; Collagenase; Asparaginase; Oral interferon alfa; Reteplase; Rituximab; Ribavirin and Alfa Interferon (Intron A); Oxytocin; Interferon gamma-lb; Menotropins; Tenecteplase; Thyrotropin Alfa; Oprelvekin; Hyaluronidase; Interferon alfa-n3; Lepirudin; Calcitonin, salmon; Imiglucerase; Digibind; Streptokinase; Antihemophilic Factor; Urokinase; Insulin, porcine; Darbepoetin alfa; Sermorelin; Choriogonadotropinalfa; Sargramostim; Gramicidin D; Alglucerase; Factor IX; Secretin, synthetic; Antithymocyte globulin; Abciximab; Palifermin; Peginterferon alfa-2a; Pegvisomant; Insulin Glargine recombinant; Digoxin Immune Fab; Peginterferon alfa-2b; Adalimumab; Alteplase; Abarelix; Etanercept; Becaplermin; OspA lipoprotein; Alefacept; Lutropin alfa; Glucagon recombinant; Human Serum Albumin; Anakinra; Desmopressin acetate; Interferon alfacon-1; Eptifibatide; Follitropin beta; Insulin Lyspro recombinant; Interferon alfa-2b; Pancrelipase; Drotrecogin alfa; Ibritumomab; Botulinum toxin type B; Cetuximab; Filgrastim; Basiliximab; Efalizumab; Agalsidase beta; Bivalirudin; Gemtuzumab ozogamicin; Interferon beta-I b; Pegaspargase; Capromab; Omalizumab; Aldesleukin; Natalizumab; Denileukin diftitox; Tositumomab; Somatropin recombinant; Bevacizumab; Octreotide acetate; Serum albumin iodonated; Rasburicase; Immune globulin; Botulinum Toxin; Interferon beta-la; Pegfilgrastim; Interferon alfa-2a; Interferon alfa-nl; Palivizumab; Trastuzumab; Follitropin alfa/beta; Pegademase bovine; Serum albumin; Anistreplase; Epoetin alfa; Urofollitropin; Insulin recombinant; Enfuvirtide; Arcitumomab; Satumomab Pendetide; Alemtuzumab; Vasopressin; Daptomycin; Desmopressin; Goserelin; Felypressin; Cetrorelix; fkb-001; tmc114; uic-94017; ca-074; [n-(1-3-trans-propylcarbamoyl-oxirane-2-carbonyl)-1-isoleucyl-1-proline]; 4-[5-[2-(I-phenyl-ethylamino)-pyrimidin-4-yl]-1-methyl-4-(3-trifluoromethylphenyl)-lh-imidazol-2-yl] piperidine; I-(5-chloroindol-3-yl)-3-hydroxy-3-(2htetrazol-5-yl)-propenone; 2'-deoxy-adenosine 3'-monophosphate; 4-(5-bromo-2-oxo-2h-indol-3-ylazo) benzenesulfonamide; didecyl-dimethyl-ammonium; (In)-4-n-butoxyphenylsulfonyl-(2r)-n-hydroxycarboxamido-(4s)methanesulfonylamino-pyrrolidine; 7,8-dihydroxy-lmethoxy-3-methyl-1 O-oxo-4,1 O-dihydro-lh,3h-pyrano[4,3-b] chromene-9-carboxylic acid; mevastatin; 2-(2-oxo-1,2-dihydro-pyridin-3-yl)-1 h-benzoimidazole-5-carboxamidine; 2-(2-hydroxy-phenyl)-3h-benzoimidazole-5-carboxamidine; 2-(2-hydroxy-5-methoxy-phenyl)-1h-benzoimidazole-5-carboxamidine; 2-(2-hydroxy-phenyl)-1h-indole-5-carboxamidine; spiro(2,4,6-trinitrobenzene[I,2a]-2o',3o'-methylene-adenine-tri-phosphate; [2(formyl-hydroxyamino)-ethyl]-phosphonic acid; 12-hydroxydodecanoic acid; 6-chloro-2-(2-hydroxy-biphenyl-3-yl)-1h-indole-5-carboxamidine; 1-(o-carboxy-phenylamino)-1-deoxy-d-ribulose-5-phosphate; n-[5'-o-phosphono-ribofuranosyl]-2-[2-hydroxy-2-[4-[glutamic acid]-n-carbonylphenyl]-3-[2-amino-4-hydroxy-quinazolin-6-yl]-propanylamino]-acetamide; 1,3-dihydroxyacetonephosphate; n-hexadecanoylglycine; 2-amino-3-[5-(amino-carboxy-methyl)-2,3-dihydro-isoxazol-3-ylsulfanyl]-propionic acid; tris-hydroxymethyl-methyl-ammonium; 1-o[o-nitrophenyl]-beta-d-galactopyranose; sd146; 1-o[p-nitrophenyl]-beta-d-galactopyranose; d-galctopyranosyl-1-on; n-(3-(aminomethyl)benzyl)acetamidine; 4,5-dimethyl-1,2-phenylenediamine; (3-carboxy-2-(r)-hydroxy-propyl)-trimethyl-ammonium; (2s)-2-[(2,4-dichloro-benzoyl)-(3-trifluoromethyl-benzyl)-amino]-3-phenyl-propionic acid; (2s)-2-[(5-benzofuran-2-yl-thiophen-2-ylmethyl)-(2,4-dichloro-benzoyl)-amino]-3-phenylpropionic acid; 6-[n-(1-isopropyl-3,4-dihydro-7-isoquinolinyl) carbamyl]-2-naphthalenecarboxamidine; 4-[3-oxo-3-(5,5,8,8-tetramethyl-5,6,7,8-tetrahydro-naphthalen-2-yl)-propenyl]-benzoic acid; n-{3-[4-(3-amino-propyl)piperazin-1-yl]-propyl}-3-nitro-5-(galactopyranosyl)-betabenzamide; 5-[4-(1-carboxymethyl-2-oxopropylcarbamoyl)-benzylsulfamoyl]-2-hydroxy-benzoic acid; pantothenyl-aminoethanol-acetate pivalic acid; 1-(4-tert-butylcarbamoyl-piperazine-1-carbonyl)-3-(3-guanidino-propyl)-4-oxo-azetidine-2-carboxylic acid; cetyl-trimethyl-ammonium; 1,6-diaminohexane; 16g; 2-phenylaminoethanesulfonic acid; 2-amino-5-hydroxy-benzimidazole; benzoylformic acid; 4-chlorobenzoic acid; 3,5-dihydro-5-methylidene-4h-imidazol-4-on; 4-(4-hydroxy-3-isopropylphenylthio)-2-isopropylphenol; bms 1843 94; [1-(I-methyl-4,5-dioxo-pent-2-enylcarbamoyl)-2-phenyl-ethyl]-carbamic acid benzyl ester; propionyl coenzyme a; (2s)-4-(beta-alanylamino)-2-amino butanoic acid; 4-{2-[(3-nitro benzoyl) amino] phenoxylphthalic acid; 4-{2,4-bis [(3-nitrobenzoyl) amino]phenoxylphthalic acid; ru82197; (2r)-n-[4-cyano-3-(trifluoromethyl)phenyl]-3-[(4-fluorophenyl)sulfonyl]-2-hydroxy-2-methylpropanamide; 1-aminocyclopropanecarboxylic acid; diureido-acetate; 2-fluoroaniline; butan-1-ol; I-bromopropane-2-ol; coproporphyrini; 1-deazaadenosine; n-(2-morpholin-4-yl-1-morpholin-4-ylmethyl-ethyl)-3-nitro-5-(3,4,5-trihydroxy-6-hydroxymethyl-tetrahydro-pyran-2-yloxy)-benzamide; 12-phenylheme; 2-deoxy-2-aminogalactose; 6-hydro-1-methyladenosine-5'-monophosphate; 1-methylcytosine; 1-methylimidazole; 1 na; (3r)-1-acetyl-3-methylpiperidine; [(le)-4-phenylbut-1-enyl]benzene; 2-(2-{2-[2-(2-methoxy-ethoxy)-ethoxy]-ethoxy}-ethanol; n'-(pyrrolidino[2,1-b]isoindolin-4-on-8-yl)-n-(pyridin-2-yl)urea; alpharibazole-5'-phosphate derivative; tribenuron methyl; I-amino-6-cyclohex-3-enylmethyloxypurine; 8-amino-1,3-dimethyl-3, 7-dihydropurine-2,6-dione; pas219; bmsc-0013; compound 9; 6-[n-(4-(aminomethyl)phenyl)carbamyl]-2-naphthalenecarboxamidine; (s)-2-amino-3-(6h-selenolo[2, 3-b]-pyrrol-4-yl)-propionic acid; 2,4-difluorobenzyl alcohol 2,4-difluoro-l-(hydroxymethyl)benzene; srl 1254; ru79256; ru78262; zk-800270; 5-chloro-.lh-indole-2-carboxylic acid{ [cyclopentyl-(2-hydroxy-ethyl)-carbamoyl]-methyl}-amide; ru78299; 2-amino-p-cresol; 2-amino-adenosine; 2-aminophenol; I-anilino-8-naphthalene sulfonate; beta-methylaspartic acid; alpha-benzyl-aminobenzyl-phosphonic acid; (1 r,4s)-2-azabornane; benzofuran-2-carboxylic acid {(s)-3-methyl-1-[3-oxo-l-(pyridin-2-ylsulfonyl)azepan-4-ylcarbamoyl] butyl}amide; 2-chlorophenol; 2-chloro-6-methylaniline; 2-carboxypropyl-coenzyme a; 2-deoxy-betadgalactose; 2'3'-dideoxyinosine; 2',3'-dideoxythymidine-5'monophosphate; 2-fluoroadenosine; 2-fluoro-2'deoxyadenosine; 2-fluoro-2-deoxy-beta-d-galactopyranose; 2-phenylheme; 2-fluoro-2-deoxy-beta-d-galactopyranosyl; beta-d-glucopyranose; difluoromethionine; 1,6-fructose diphosphate (linear form); guanosine-2'-monophosphate; dihydroxyacetone; trans-2-hydroxycinnamic acid; o-coumaric acid; dihydrogenphosphate ion; d-myo-inositol-1,4-bisphosphate; 2-oxobutanoic acid; 2-allylphenol; leucine-reduced carbonyl; methacrylyl-coenzyme a; 2-methylleucine; 3,4-dimethylphenol; n3, n4-dimethylarginine; 2,2-dimethylthiazolidine-4-carboxylic acid; (dmt)thiazolidine; 2'-deoxyinosine; 1-2-amino-6-methylene-pimelic acid; 2-oxo-glutaric acid; (2s)-2-hydroxypropanal; 3'-o-n-octanoy 1-a-d-glucopyranosy 1-b-d-fructofuranoside; 2-[(dioxidophosphino)oxy]benzoate; 3,4-dihydro-2h-pyrrolium-5-carboxylate; nonaethylene glycol; 2-phosphoglyceric acid; 2-amino-pentanoic acid; phosphoglycolic acid; adenylosuccinic acid; ru78300; 6-[n-(1-isopropyl-1,2,3,4-tetrahydro-7-isoquinolinyl)carbamyl]-2-naphthalenecarboxamidine; cra_I 7312; 2-[5-hydroxy-3-methyl-1-(2-methyl-4-sulfophenyl)-1 h-pyrazol-4-ylazo]-4-sulfo-benzoic acid; (s)-2-amino-3-(4h-selenolo[3,2-b]-pyrrol-6-yl)-propionic acid; cra_9334; {3-[(3-hydroxy-2-methyl-5-phosphonooxymethyl-pyridin-4-ylmethyl)-amino]-2-methyl-propyl}-phosphonic acid; 5-methoxy-1,2-dimethy 1-3-(phenoxymethyl)indole-4, 7-dione; 3,4-dimethylaniline; (3-chloro-4-propoxyphenyl)-acetic acid; 1-(2,6-dichlorophenyl)-5-(2,4-difluorophenyl)-7-piperidin-4-yl-3,4-dihydroquinolin-2 (lh)-one; guanosine-3',5'-monophosphate; 3,9-dimethyladenine; 3-aza-2,3-dihydrogeranyl diphosphate; 3'-deoxy 3'-amino adenosine-5'-diphosphate; n-omega-propyl-1-arginine; cordycepin triphosphate; s,s'-(1,3-phenylenebis(1,2-ethanediyl))bis-isothiourea; 3-chlorophenol; 2'-deoxyadenosine; 3-deoxyguanosine; gamma-glutamylcysteine; guanosine-3'-monophosphate; (2r)-2,3-dihydroxypropanal; 2-amino-3-hydroxybenzoic acid; 3-hydroxybutyryl-coenzyme a; 3-indolebutyric acid; 3h-indole-5,6-diol; n-[2(s)-cyclopentyl-1 (r)-hydroxy-3(r) methyl]-5-[(2(s)-tertiary-butylamino-carbonyl)-4-(nl-(2)-(n-methylpiperazinyl)-3-chloro-pyrazinyl 1-5-carbonyl)-piperazino]-4(s)-hydroxy-2(r)-phenylmethyl-pentanamide; 3-(benzyloxy) pyridin-2-amine; 3-methoxybenzamide; 3-methylcytosine; 2s,3s-3-methylaspartic acid; 3-o-methylfructose inlinear form; 3-methylpyridine; (3s)-tetrahydrofuran-3-yl(Ir,2s)-3-[4-((Ir)-2-{[(s)-amino(hydroxy)methyl] oxy}-2,3-dihydrolh-inden-1-yl)-2-benzyl-3-oxopyrrolidin-2-yl]-1-benzyl-2-hydroxypropylcarbamate; 3-hydroxypropanoic acid; I-octen-3-ol; (Ir)-4-[(le,3e,5e, 7z,9e,1lz,13e, 15e)-17-hydroxy-3,7,12, 16-tetramethylheptadeca-1,3,5,7, 9,11,13, 15-octaen-1-yl]-3,5,5-trimethylcyclohex-3-en-1-ol; (3s)-3,4-din-hexanoyloxybutyl-1-phosphocholine; 3-phosphoglyceric acid; triphospate; 2-carboxyethylphosphonic acid; 3-hydroxypyruvic acid; 4-o-(4,6-dideoxy-4-{[4,5,6-trihydroxy-3-(hydroxymethyl)cyclohex-2-en-1-yl]amino}-beta-d-lyxohexopyranosyl)-alpha-d-erythro-hexopyranose; (r)-2-hydroxy-3-sulfopropanoic acid; compound 6; n-(allyloxycarbonyl)-4-[n-(carboxy-formyl)-2-(benzoic acid)-amino]-1-phenylalaninyl-amino-butyloxy-(6-hydroxy-benzoic acid methyl ester); bilh 434; 4-(lh-imidazol-4-yl)-3-(5-ethyl-2,4-dihydroxy-phenyl)-lh-pyrazole; [3,5-dibromo-4-(4-hydroxy-3-phenethylcarbamoy 1-phenoxy)phenyl]-acetic acid; dmp450; 3-(5-amino-7-hydroxy-[1,2,3]triazolo [4,5-d]pyrimidin-2-yl)-n-(3,5-dichlorobenzyl)benzamide; naphthyridine inhibitor; ru85493; 6-[n-(4-ethyl-1,2,3,4-tetrahydro-6-isoquinolinyl)carbamyl]-2-naphthalenecarboxamidine; 4-amino-2-deoxy-2,3-dehydron-neuraminic acid; (r)-4-amino-isoxazolidin-3-one; 4-(1,3-benzodioxol-5-yl)-5-(5-ethyl-2,4-dihydroxyphenyl)-2hpyrazole-3-carboxylic acid; s,s'-(1,4-phenylene-bis(1,2-ethanediyl))bis-isothiourea; 4-(hydroxymethyl) benzamidine; 4-hydroxybenzyl coenzyme a; 4-carboxyphenylboronic acid; 4-hydroxyphenacyl coenzyme a; 1-(4-methoxyphenyl)-3,5-dimethyl-lh-pyrazole-4-carboxylic acid ethyl ester; [2-(l-amino-2-hydroxy-propyl)-4-(4-fluoro-lh-indol-3-ylmethyl)-5-hydroxy-imidazol-1-yl]-acetic acid; 4-fluorophenethyl alcohol; 4-fluorotryptophane; 4-hydroxybutan-1-aminium; 4-hydroxy-1-benzopyran-2-one; 4-hydroxycoumarin; 4-hydroperoxy-2-methoxy-phenol; [4-(4-hydroxy-3-iodo-phenoxy)-3,5-diiodo-phenyl]-acetic acid; 2-amino-3-(4-amino-lhindol-3-yl)propanoic acid; inositol-(1,3,4,5) tetrakisphosphate; 4-methyl valeric acid; 4-methylimidazole; 4-nitrocatechol; 4-nitrophenyl phosphate; 4-oxosebacic acid; propyl acetate; n-hydroxy-4-phosphono-butanamide; 4-piperidino-piperidine; (r)-rolipram; (s)-rolipram; 4-(2-thienyl) butyric acid; 4-hydroxy-l-threonine-5-monophosphate; 2,6-dihydroanthra/1,9-cd/ pyrazol-6-one; cd564; cp-166572, 2-hydroxymethyl-4-(4-n, n-dimethylaminosulfonyl-1-piperazino)-pyrimidine; 3-(4-fluorophenyl)-2-(6-methylpyridin-2-yl)-5,6-dihydro-4 h-pyrrolo [I,2-b]pyrazole; 1-709,587; 3,5-difluoroaniline; 5-(aminomethyl)-6-(2,4-dichlorophenyl)-2-(3,5-dimethoxyphenyl)pyrimidin-4-amine; 5'-o-(nethy 1-sulfamoyl)adenosine; 5'-o-(n-(1-cysteinyl)-sulfamoyl) adenosine; 2-amino-3-(cystein-s-yl)-isoxazolidin-5-ylacetic acid; 1-(4-aminophenyl)-3,5-dimethyl-lh-pyrazole-4-carboxylic acid ethyl ester; adenosine-5'-pentaphosphate; 5'-fluoro-5'-deoxyadenosine; guanosine-5'-monophosphate; pyroglutamic acid; 5-hydroxymethyluridine-2'-deoxy-5'monophosphate; 5-iodo-2'-deoxyuridine-5'-monophosphate; 5-methylbenzimidazole; 5-methylcytidine-5'-monophosphate; 5-methyl-2'-deoxypseudouridine; 5-methylpyrrole; 5-methyluridine 5'-monophosphate; 5-nitroindazole; 5-methoxybenzimidazole; n-pyridoxyl-1-aminocyclopropanecarboxylic acid-5-monophosphate; 5-phenylvaleric acid; (r)-mesopram; ribulose-5-phosphate; 5alpha-androstan-3, 17-dione; 5-fluorouridine; (5z)-2-[(1 s,2r)-1-amino-2-hydroxypropyl]-5-[(4-amino-I h-indol-3-yl)methylene]-3-(2-hydroxyethyl)-3,5-dihydro-4h-imidazol-4-one; n-[2-(I-formyl-2-methyl-propyl)-1-(4-piperidin-1-yl-but-2-enoyl)-pyrrolidin-3-yl]- methanesulfonamide; zk-805623; xv638; cra_23653; 4-(2-thienyl)-1-(4-methylbenzyl)-lhimidazole; cra_0655; cra_1 0656; (5r)-6-(4-{[2-(3-iodobenzyl)-3-oxocyclohex-1-en-1-yl]amino}phenyl)-5-methyl-4,5-dihydropyridazin-3(2h)-one; 6-oxo-8,9,1 O,lltetrahydro-7h-cyclohepta[c][1]benzopyran-3-o-sulfamate; 1-(5-carboxypentyl)-5-[(2,6-dichlorobenzyl)oxy]-1 h-indole-2-carboxylic acid; 6-(n-phenylcarbamyl)-2-naphthalenecarboxamidine; cra_9678; i-5; 6-methylamino-5-nitroisocytosine; ono-6818; ru84687; cra_7693; cra_8696; 6-aminobenzoic acid; I-(2-chlorophenyl)-3,5-dimethyl-lhpyrazole-4-carboxylic acid ethyl ester; 6-hydroxy-flavin-adenine dinucleotide; 4-(1-benzy 1-3-carbamoylmethyl 1-2-methyl-I h-indol-5-yloxy)-butyric acid; 6-methylpurine; 6-nitroindazole; 6((s)-3-benzylpiperazin-1-yl)-3-(naphthalen-2-yl)-4-(pyridin-4-yl)pyrazine; 6-phosphogluconic acid; acarbose derived hexasaccharide; cp403700, (s)-1-{2-[(5-chloro-lh-indole-2-carbonyl)-amino]-3-phenyl-propionyl}azetidine-3-carboxylate; 6-[3-(4-morpholinyl)propyl]-2-(3-nitrophenyl)-5-thioxo-5,6,-dihydro-7h-thienol[2',3':4,5] pyrrolo[1,2-c]imidazol-7-one; zk-806711; trans-6-(2-phenylcyclopropyl)-naphthalene-2-carboxamidine; 9-n-phenylmethylamino-tacrine; 3-(oxalyl-amino)-naphthalene-2-carboxylic acid; cra_10762; ru79072; cra_7806; era_9785; ru78783; ru79073; ru78191; compound 5,2-(naphthalen-1-yl-oxalyl-amino)-benzo-icacid; (4r)-7aza-7,8-dihydrolimonene; 9-amino-n-[3-(dimethylamino)propyl] acridine-4-carboxamide; 3,5-dimethyl-1-(3-nitrophenyl)lh-pyrazole-4-carboxylic acid ethyl ester; 7-deazaguanine; 7-hydroxy-pyrazolo[4,3-d]pyrimidine; 7-nitroindazole-2-carboxamidine; 7n-methyl-8-hydroguanosine-5'-monophosphate; 7-nitroindazole; 7-alpha-d-ribofuranosyl-2-aminopurine-5'-phosphate; 7-alpha-d-ribofuranosyl-purine-5'phosphate; cra_1801; cra_1802; zk-806450; ru82129; ru82209; 1,3,4,9-tetrahydro-2-(hydroxybenzoyl)-9-[(4-hydroxyphenyl) methyl]-6-methoxy-2h-pyrido[3,4-b]indole; ru81843; cra_16847; ru85053; (1-tert-butyl-5-hydroxy-lhpyrazol-4-yl)-(6-methanesulfonyl-4'-methoxy-2-methyl-biphenyl-3-yl)-methanone; ru83876; nova nordisk a/s compound; cyclohexyl-{4-[5-(3, 4-dichlorophenyl)-2-piperidin-4-yl-3-propyl-3h-imidazol-4-yl]-pyrimidin-2-yl}amine; 3-(3,5-dibromo-4-hydroxy-benzoyl)-2-ethyl-benzofuran-6-sulfonic acid (4-sulfamoyl-phenyl)-amide; 8-bromoadenosine-5'-monophosphate; 8-hydroxy-2'-deoxyguanosine; 8-iodo-guanine; [3-(I-benzyl-3-carbamoylmethyl-2-methyllh-indol-5-yloxy)-propyl-]-phosphonic acid; 2-[(2e,6e,10e, 14e, 18e,22e,26e)-3, 7, 11, 15, 19,23,27,31-octamethyldotriaconta-2,6, 10, 14, 18,22,26,30-octaenyl]phenol; compound 19; ru90395; cra_9076; 5-methoxy-1,2-dimethyl-3-(4-nitrophenoxymethyl) indole-4,7-dione; compound 15; era_10950; sp7343-sp7964; (3-{3-[[2-chloro-3-(trifluoromethyl) benzyl] (2,2-diphenylethyl)amino]propoxy} phenyl)acetic acid; cra_0972; 2-amino-5-bromo-6-phenylpyrimidin-4-ol; cyclopropyl-{4-[5-(3,4-dichlorophenyl)-2-[(1-methyl)piperidin]-4-yl-3-propyl-3h-imidazol-4-yl]-pyrimidin-2-yl}amine; compound 12, n-acetyl-4-[(carboxycarbonyl)(2-carboxyphenyl)amino]-n-penty 1-1-napthylalaniamide; era_10991; I-[3,3-dimethyl-2-(2-methylaminopropionylamino)-butyryl]-pyrrolidine-2-carboxylic acid(I, 2,3,4-tetrahydro-naphthalen-1-yl)-amide; 9-amino-2-deoxy-2,3-dehydro-n-acetyl-neuraminic acid; 9-aminophenanthrene; 9-hydroxy-8-methoxy-6-nitrophenanthrol[3,4-d][1,3]dioxole-5-carboxylic acid; 9-deazaadenine; 9-deazaguanine; 9-deazainosine; 9-(4-hydroxyphenyl)-2, 7-phenanthroline; 9-deazahypoxanthine; 9-methylguanine; 2,6-diamino-(s)-9-[2-(phosphonomethoxy) propyl]purine; phosphomethylphosphonic acid adenosyl ester; antiproliferative agent a771726; n-acetyl-2-deoxy-2-amino-galactose; adenosine-2'-5'-diphosphate; 2-ammonio but-3-enoate, 2-amino-3-butenoate; 3-acetylpyridine adenine dinucleotide; 2-amino-3-methyl-1-pyrrolidinl-yl-butan-1-one; adenosine-3'-5'-diphosphate; n'-1-seryl-3'amino-(3'-deoxy)-adenosine; 3-(5-amino-7-hydroxy-[I,2,3] triazolo[4,5-d]pyrimidin-2-yl)-benzoic acid; 6-(adenosine tetraphosphate-methyl)-7, 8-dihydropterin; '5'-o-(n-(I-alanyl)-sulfamoyl)adenosine; arabinose-5-phosphate; n-(5,5,8, 8-tetramethyl-5,8-dihydro-naphthalen-2-yl)-terephthalamic acid; a-98881; 4-[4-(I-amino-I-methylethyl)phenyl]-5-chloro-n-[4-(2-morpholin-4-ylethyl)phenyl]pyrimidin-2-amine; acetylamino-acetic acid; 5'-[[2-(aminooxy)ethyl]methylsulfonio]-5'-deoxy-adenosine; [2-(amino-oxy)ethyl]5'deoxyadenosin-5'-yl] (methyl)sulfonium; acetoacetic acid; n-alpha-1-acetyl-arginine; alpha-adenosine monophosphate; arginineamide; s-adenosy 1-1, 8-diamino-3-thiooctane; Ifa703; abt-378, lopinavir; 3-(4-amino-1-tert-butyl-lh-pyrazolo[3,4-d]pyrimidin-3-yl)phenol; alpha-aminobutyric acid; (2s,4(r)-1-acetyl-n-[(1 s)-4-[(aminoiminomethyl)amino]-1-(2-benzothiazolylcarbonyl)butyl]-4-hydroxy-2-pyrrolidinecarboxamide; modified acarbose hexasaccharide; abequose; beta-d-arabinofuranose-5'-phosphate; 2(s)-amino-6-boronohexanoic acid; 5-amidino-benzimidazole; 5-amino-5-deoxycellobiono-1,5-lactam; alpha-methylene adenosine monophosphate; benzylamine; 8-bromoadenosine-5'-diphosphate; gamma(amino)-butyric acid; 5-[1-(acetylamino)-3-methylbutyl]-2,5-anhydro-3,4-dideoxy-4-(methoxycarbonyl)pentonic acid; n-(4-aminobutanoyl)-s-(4-methoxybenzyl)-1l-cysteinylglycine; n44-hydroxymethyl-cyclohexan-6-yl-1,2,3-trioq-4,6-dideoxy-4-aminoglucopyranoside; 9-hyroxyethoxymethylguanine; aicar; aminocaproic acid; arachidonic acid; modified acarbose pentasaccharide; acetylcholine; 6-amino-4-hydroxymethyl-cyclohex-4-ene-1,2,3-triol; acetamide; adenosine-5'-[beta, gamma-methylene] triphosphate; adenosine-5'-[beta, gamma-methylene]tetraphosphate; 1-[(1 s)-carboxy-2-(methylsulfinyl)ethyl]-(3r)-[(5s)-5-amino-5-carboxypentanamido]-(4r)-sulfanylazetidin-2-one; acetate ion; 1-d-(a-aminoadipoy 1)-1-cysteiny 1-d-valine; alpha-cyclodextrin (cyclohexa-amylose); acetic acid; 2-amino-4-(4-amino-cyclohexa-2,5-dienyl)-butyric acid; 3-deazaadenosine; alpha d-galacturonic acid; (1'r, 2's)-9-(2-hydroxy-3'-keto-cyclopenten-1-yl)adenine; 2,6,8-trimethyl-3-amino-9-benzyl-9-methoxynonanoic acid; 1-amino-2,3-dihydroxy-5-hydroxymethyl I cyclohex-5-ene; 3-methyladenine; acetyl dithranol; adamantane; adamantanone; adenosine-5'-diphosphate; adenosine-5'-monophosphate glucopyranosyl-monophosphate ester; adenosine-5'(dithio)phosphate; ampcpr; {[5-(6-amino-purin-9-yl)-3,4-dihydroxy-tetrahydro-furan-2-ylmethoxy]-hydroxyphosphorylmethyl}-phosphonic acid mono-(3,4,5-trihydroxy-tetrahydro-furan-2-ylmethyl) ester; adenosine-5'ditungstate; adenosine-5'-phosphosulfate; 3'-oxo-adenosine; aetiocholanolone; aeruginosin 98-b; threonine-aspartic ester; 1-[4-(octahydro-pyrido[1,2-a]pyrazin-2-yl)-phenyl]-2-phenyl-1,2,3,4-tetrahydro-isoquinolin-6-ol; 2-aminoethanimidic acid; 3-[(1-amino-2-carboxy-ethyl)-hydroxy-phosphinoyl]-2-methyl-propionic acid; 4-deoxy-4-((5-hydroxymethy 1-2,3,4-trihydroxycyclohex-5,6-enyl)amino) fructose; 2-[4-(4-chlorophenyl)cyclohexylidene]-3,4-dihydroxy-I (2h)-naphthalenone; alpha-1-fucose; 4-{2-(4-fluoro-benzyl)-6-methyl-5-[(5-methyl-isoxazole-3-carbonyl)-amino]-4-oxo-heptanoylamino}-5-(2-oxopyrrolidin-3-yl)-pentanoic acid ethyl ester; n-(1-adamantyl)n'-(4-guanidinobenzyl)urea; alpha-d-glucose; 4,6-dideoxy-4-amino-alpha-d-glucose; 2-deoxy-2-amino glucitol-6-phosphate; phosphothiophosphoric acid-adenylate ester; aminoguanidine; (4r,5s, 6s, 7r)-1,3-dibenzyl-4,7-bis(phenoxymethyl)-5,6-dihydroxy-1,3 diazepan-2-one; 6-amino hexanoic acid; beta-hydroxyasparagine; 4-aminohydrocinnamic acid; s-hydroxymethyl glutathione; 2-[4-(hydroxymethoxy-methyl)-benzyl]-7-(4-hydroxymethyl-benzyl)-1,ldioxo-3,6-bis-phenoxymethyl-llambda6-[1,2, 7]thiadiazepane-4,5-diol; 2,5-anhydroglucitol-1,6-biphosphate; descarboxy-nor-n(omega)-hydroxy-l-arginine; alpha-1-arabinofuranose; adenosine diphosphate 5-(betaethyl)-4-methyl-thiazole-2-carboxylic acid; n-benzyl-3-(3,4, 5-trihydroxy-6-hydroxymethyl-tetrahydro-pyran-2-yloxy) benzamide; bmscOOI; 3-benzylaminocarbonylphenyl-alphad-galactoside; bapg; alpha-aminoisobutyric acid; compound 15; compound 18; n-[3-(dimethylamino)propyl]-2-({[4-({[4-(formylamino)-1-methyl-lh-pyrrol-2-yl]carbonyl}amino)-1-methyl-lh-pyrrol-2-yl]carbonyl}amino)-5-isopropyl-1,3-thiazole-4-carboxamide; acetylsalicylic acid, aspmn; 2,6-diamino-8-(lh-imidazol-2-ylsulfanylmethyl)-3hquinazoline-4-one; 5-aminoimidazole ribonucleoside; compound 19; compound 16; 3-(prop-2-ene-1-sulfinyl)-propene-1-thiol; 10-{4-dimethylamino-5-[4-hydroxy-6-methyl-5-(6-methyl-5-oxo-tetrahydro-pyran-2-yloxy)-tetrahydropyrane-2-yloxy]-6-methyl-tetrahydro-pyran-2-yloxy}-8-ethyl-1,8, 11-trihydroxy-7,8,9, 1 O-tetrahydro-naphthacene-5, 12-dione; 2-amino-3-ketobutyric acid; 2-oxyglutaric acid; acrylic acid; 10-(4-dimethyl-amino-5-hydroxy-6-methyl-tetrahydro-pyran-2-yloxy)-8-ethyl-1,8, 11-trihydroxy-7,8,9,1 Otetrahydro-naphthacene-5, 12-dione; al 7182; al 5424; a15300; a14623; a16528; al 7099a; al 7089a; a15927; delta-2-albomycin al; adr adrenaline; tetrafluoroaluminate ion; n"-{3-[(3s,8ar)-1,4-dioxooctahydropyrrolo[I,2-a]pyrazin-3-yl]propyl}guanidine; d-allopyranose; 2-methyl-propionic acid; alrestatin; 2-amino-3-oxo-4-sulfo-butyric acid; 1-2-amino-4-methoxy-cis-but-3-enoic acid; aminomethylcyclohexane; n-acetylmethionine; alpha-methyl-d-galactoside; trans-4-aminomethylcyclohexane-I-carboxylic acid; allosamizoline; amylamine; aspartyl-adenosine-5'-monophosphate; adenosine monophosphate; ampa; 3-mercuri-4-aminobenzenesulfonamide; adenosine monotungstate; aminoanthracene; 3-beta-hydroxy-5-androsten-17-one; adenine; nalpha-(2-naphthylsulfonylglycyl)-3-amidino-d,l-phenylalanine-isopropyl-ester; p-anisic acid; phosphoaminophosphonic acid-adenylate ester; (6e)-6-[(2e,4e,6e)-3,7-dimethylnona-2,4,6, 8-tetraenylidene]-1,5,5-trimethylcyclohexene; (2s,3r)-3-amino-2-hydroxy-5-(ethylsulfanyl)pentanoyl-((s)(−)-(1-naphthyl)ethyl)amide; n'-(2s,3r)-3-amino-4-cyclohexyl-2-hydroxy-butano-n-(4-methylphenyl)hydrazide; (aminooxy) acetic acid; n-butyl-II-[(7r,8r,9s,13s,14s,17s)-3, 17-dihydroxy-13-methyl-7,8,9,11,12,13,14,15,16,17-decahydro-6h-cyclopenta[a]phenanthren-7-yl]-n-methylundecanamide; 5-alpha-androstane-3-beta, 17beta-diol; 5-alpha-androstane-3-beta, 17-alpha-diol; {3-[3-(3,4-dimethoxy-phenyl)-1-(1-{I-[2-(3,4,5-trimethoxy-phenyl)butyryl]-piperidin-2yl}-vinyloxy)-propyl]-phenoxy}-acetic acid; phosphomethylphosphonic acid adenosyl ester; 5,6-cyclic-tetrahydropteridine; bis(adenosine)-5'-pentaphosphate; 2,4-diamino-6-phenyl-5,6,7,8,-tetrahydropteridine; amido phenyl pyruvic acid; m-aminophenylboronic acid; alpha, beta-methyleneadenosine-5'-triphosphate; 3-methylphenylalanine; 2,6-diaminopimelic acid; d-2-amino-3-phosphonopropionic acid; 2,6-diamino-8-propylsulfanylmethyl-3hquinazoline-4-one; adenosine-5-diphosphoriboside; 9-hydroxypropyladenine, s-isomer; pteric acid; adenylyl-3'-5'-phospho-uridine-3'-monophosphate; 2'-monophosphoadenosine-5'-diphosphoribose; 4-aminophthalhydrazide; erlotinib; 2-aminoquinazolin-4(3h)-one;

modified ribosylated glutamyl ester; alpha-1-arabinose; beta-1-arabinose; 3,7,11, 15-tetramethyl-hexadecan-l-ol; 4-o-(4,6-dideoxy-4-{[4-[(4-o-hexopyranosylhexopyranosyl)oxy]-5, 6-dihydroxy-3-(hydroxymethyl)cyclohex-2-en-1-yl] amino}hexopyranosyl) hexopyranose; 9-hydroxypropyladenine, r-isomer; n-(4-(2-((3-chlorophenylmethyl)amino)ethyl)phenyl)-2-thiophecarboxamidine; 5-n-allyl-arginine; n-methyl-n-(10-methylundecanoyl)-d-seryl-l-alanyl-n-1-[(7 s, 1 Os, 13s)-13-carboxy-3, 18-dihydroxy-1 O-methyl-8, 11-dioxo-9, 12-diazatricyclo[13.3.1.1-2,6-] icosa-1 (19),2(20),3,5, 15, 17-hexaen-7-yl]-n-1-methyl-glycinamide; argininosuccinate; aspartate semialdehyde; aspartic acid-4-carboxymethyl ester; ascorbic acid; 4-androstene-3-17-dione; n-acetyl serotonin; 1-iso-aspartate; phosphoaspartate; 4-aminophenylarsonic acid; delta-(1-alpha-aminoadipoyl)-1-cysteinyl-d-vinylglycine; 2-amino-3-(5-tert-butyl-3-(phosphonomethoxy)-4-isoxazolyl)propionic acid; atrazine glutathione conjugate; 16,17-androstene-3-ol; 4-hydroxy-aconitate ion; 3'-azido-3'-deoxythymidine-5'-monophosphate; apstatin; chloroacetone; 2-aminothiazoline; 2'-monophosphoadenosine-5'-diphosphate; gamma-arsono-beta, gammamethyleneadenosine-5'-diphosphate; alsterpaullone; 3'-oacetylthymidine-5'-diphosphate; adenosine-5'-diphosphate-2',3'-vanadate; 2-amino-4-(2-amino-ethoxy)-butyric acid; 2-{I-[2-amino-2-(4-hydroxy-phenyl)-acetylamino]-2-oxoethyl}-5,5-dimethyl-thiazolidine-4-carboxylic acid; 4-acetamido-2,4-didexoy-d-glycero-beta-d-galacto-octopyranosylphosphonic acid (an axial phosphonate); n-acetylalanine; 3-(6-aminopyridin-3-yl)-n-methyl-n-[(1-methyl-lh-indol-2-yl)methyl]acrylamide; azelaic acid; 8-azaxanthine; n-acetyln'-beta-d-glucopyranosy I urea; 3'-azido-3'-deoxythymidine-5'-diphosphate; all-trans axerophthene; 8-azaguanine; 5-acetamido-1,3,4-thiadiazole-2-sulfonamide; aztreonam; cobalamin; balanol analog 1; factor iiim; 2-[(2-oxo-2-piperidin-1-ylethyl)thio]-6-(trifluoromethyl)pyrimidin-4(1h)-one; beta-1,4-galactobioside; 4-dimethylamino-n-(6-hydroxycarbamoyethyl) benzamide-n-hydroxy-7-(4-dimethyla minobenzoyl)amino-heptanamide; 2-[3-(2-hydroxy-I, 1-dihydroxymethy 1-ethylamino)-propylamino]-2-hydroxymethyl-propane-1,3-diol; beta-1,4-galactotrioside; heptylbeta-d-glucopyranoside; balanol analog 8; I-(5-tert-butyl-2-p-tolyl-2h-pyrazol-3-yl)-3-[4-(2-morpholin-4-yl-ethoxy)naphthalen-1-yl]-urea; balanol; bis(adenosine)-5'triphosphate; (tert-butyloxycarbonyl)-alanyl-alany I-amine; bis(5-amidino-benzimidazolyl) methane; bis(5-amidino-2-benzimidazolyl)methane ketone hydrate; hemi-babim; bis(5-amidino-2-benzimidazolyl) methane ketone; beta-alanine; bis(5-amidino-2-benzimidazolyl)methanone; batimastat; bb94; bis(5-amidino-benzimidazolyl)methane zinc; bb-3497; 2-[(formyl-hydroxy-amino)-methyl]-heptanoic acid [1-(2-hydroxymethyl-pyrrolidine-1-carbonyl)-2-methyl-propyl]-amide; 3-(3,5-dibromo-4-hydroxy-benzoyl)-2-ethyl-benzofuran-6-sulfonic acid dimethylamide; bis-benzamidine; I-benzyl-3-(4-methoxy-benzenesulfonyl)-6-oxohexahydro-pyrimidine-4-carboxylic acid hydroxyamide; 5-bromo-n-(2,3-dihydroxypropoxy)-3,4-difluoro-2-[(2-fluoro-4-iodophenyl)amino]benzamide; 2-hydroxy-5-[4-(2-hydroxy-ethyl)-piperidin-1-yl]-5-phenyl-lh-pyrimidine-4, 6-dione; 2'-(4-dimethylaminophenyl)-5-(4-methyl-lpiperazinyl)-2,5'-bi-benzimidazole; 4-hydroxybenzoyl coenzyme a; cyclohepta-amylose; butyrylthiocholine; bacteriochlorophyll a; bicine; 2-bromo-6-chloro-purine; benzylcysteine; beta-3-cysteine; bcx-1812; balanol analog 2; 4,4'-biphenyldiboronic acid; bromo-dodecanol; beta-dfructopyranose; 2-butyl-5,6-dihydro-lh-imidaz[4,5-d] pyridazine-4, 7-dione; brodimoprim-4,6-dicarboxylate; 2,3-bis-benzo[1,3]dioxol-5-ylmethyl-succinic acid; n-bromoacetyl-aminoethyl phosphate; 2-aminobenzoic acid; inhibitor bea403; tricyclazole; inhibitor bea369; inhibitor bea388; inhibitor bea403; inhibitor bea409; inhibitor bea425; inhibitor bea322; inhibitor bea428; 2,3,5,6-tetrafluoro-4-methoxy-benzamide; 2,4-dinitro,5-[bis(2-bromoethyl) amino]-n-(2',3'-dioxopropyl) benzamide; benzamidine; butenoic acid; berberine; bestatin; trimethyl glycine; benzoic acid; aspartate beryllium trifluoride; 2-(1,1'-biphenyl-4-yl) propanoic acid; n-[1-(4-bromophenyl)ethyl]-5-fluoro salicylamide; 3-methyl-5-sulfo-pyrrolidine-2-carboxylic acid; 5-(hydroxy-methyl-amino)-3-methyl-pyrrolidine-2-carboxylic acid; 5-hydroxyamino-3-methyl-pyrrolidine-2-carboxylic acid; beta-d-glucose-6-phosphate; beta-d-glucose; 4-benzoylamino-4-{1-{l-carbamoyl-2-[4-(difluorophosphono-methyl)-phenyl]-ethylcarbamoyl}-2-[4-(difluoro-phosphono-methyl)-phenyl]-ethylcarbamoyl}-butyric acid; b-2-octylglucoside; beta-galactose-6-phosphate; 4-methyl-pyrroline-5-carboxylic acid; 3-({5-benzyl-6-hydroxy-2, 4-bis-(4-hydroxy-benzyl)-3-oxo-[1,2,4]-triazepane-1-sulfonyl)-benzonitrile; (6r, 1'r,2's)-5,6,7,8 tetrahydrobiopterin; 6-[5-(2-oxo-hexahydro-thieno[3,4-d]imidazol-4-yl)-pentanoylamino]-hexanoic acid; 2-hydroxy-4-aminobenzoic acid; 2,6-diamino-8-(2-dimethylaminoethylsulfanylmethyl)-3h-quinazolin-4-one; benzene hexacarboxylic acid; beta-hydroxyaspartic acid; 2-hexyloxy-6-hydroxymethyl-tetrahydro-pyran-3,4,5-triol; n-butyl-n'-hydroxyguanidine; 4-bromo-3-hydroxy-3-methyl butyl diphosphate; benzhydroxamic acid; (s)-5-(4-benzyloxy-phenyl)-4-(7-phenyl 1-heptanoylamino)-pentanoic acid; 6s-5,6, 7,8-tetrahydrobiopterin; rbt205 inhibitor; 3-[1-(3-aminopropyl)-1 h-indol-3-yl]-4-(1-methyl-1 h-indol-3-yl)-1 h-pyrrole-2,5-dione; 3-335; beta-amino isobutyrate; 2,3-dicarboxy-4-(2-chloro-phenyl)l-ethy 1-5-isopropoxycarbonyl-6-methyl-pyridinium; biopterin; 2-benzyl-3-iodopropanoic acid; n-[3-[(1-aminoethyl) (hydroxy)phosphoryl]-2-(1,1-biphenyl-4-ylmethyl) propanoyl] alanine; (s)-bleb bistatin, (3as)-3a-hydroxy-6-methyl-1-phenyl-3,3a-dihydro-lh-pyrrolo[2,3-b]quinolin-4 (2h)-one; 1 (r)-1-acetamido-2-(3-carboxyphenyl)ethyl boronic acid; 2-{n'-[2-(5-amino-1-phenylcarbamoy 1-penty 1-carbamoyl)-hexyl]-hydrazinomethyl}-hexanoic acid(5-amino-1-phenylcarbamoyl-pentyl)-amide; biliverdine ix alpha; bulgecin a; 4-oxo-2-phenylmethanesulfonyl-octahydro-pyrrolo[,2-a]pyrazine-6-carboxylic acid [1-(n-hydroxycarbamimidoyl)-piperidin-4-ylmethyl]-amide; (2r,3r, 4r,5r)-3,4-dihydroxy-n,n'-bis[(1 s,2r)-2-hydroxy-2,3-dihydro-1 h-inden-1-yl]-2,5-bis(2-phenylethyl) hexanediamide; nl-[3-(dimethylsulfonio)-propyl] bleomycinamide; morpholine-4-carboxylic acid [1 s-(2-benzyloxy-lr-cyano-ethylcarbamoyl)-3-methyl-butyl] amide; biliverdin ix gamma chromophore; beta-d-mannose; butyramide; beta-mercaptoethanol; 6-hydroxyuridine-5'phosphate; 1-(5'-phospho-beta-d-ribofuranosyl) barbituric acid; 1-(5-tert-butyl-2-methyl-2h-pyrazol-3-yl)-3-(4-chlorophenyl)-urea; balhimycin; 2-(2-hydroxy-phenyl)-lh-benzoimidazole-5-carboxamidine; n-benzylformamide; b-nonylglucoside; biotinyl p-nitroaniline; benzenesulfonyl; 2-bromo-6-hydroxy-purine; tert-butyloxycarbonyl group; b-octylglucoside; bombykol; bis(5-amidino-benzimidazolyl) methanone zinc; bromopurine; 2'-chloro-biphenyl-2,3-diol; 2',6'-dichloro-biphenyl-2,6-diol; n-(m-trifluoromethylphenyl) phenoxazine-4,6-dicarboxylic acid; 9-(4-hydroxybutyl)-n2-phenylguanine; bipheny 1-2,3-diol; 6-phenyl-4(r)-(7-phenyl-heptanoylamino)-hexanoic acid; para-bromobenzyl alcohol; 12-bromododecanoic acid; l-beta-ribofuranosyl-1, 3-diazepinone; brequinar analog; 6-fluoro-2-(2'-fluoro-1, 1'-biphenyl-4-yl)-3-methylquinoline-4-carboxylic acid; 2-bromoacetyl group; diminazine aceturate; 1,3-tris-(4'amidinophenyl)triazine; 2-bromo-2-propene-l-ol; (2r)-2-{[formyl(hydroxy)amino] methyl}hexanoic acid; 5-bromonicotinamide; 5-bromo-2'deoxyuridine-5'-monophosphate; (3e)-6'-bromo-2,3'biindole-2',3 (1 h,l'h)-dione 3-oxime; 6-(1,1-dimethylallyl)-2-(1-hydroxy-1-methylethyl)-2,3-dihydro-7h-furo[3,2-g] chromen-7-one; n-benzy 1-4-sulfamoy 1-benzamide; beta-3-serine; 2-(biphenyl-4-sulfonyl)-1, 2,3,4-tetrahydro-isoquinoline-3-carboxylic acid; bis-tris buffer; 5-bromothienyldeoxyuridine; [formylmethyl]trimethy 1-annnonium, n,n, n-trimethylammonium acetaldehyde; 2-thiomethyl-3-phenylpropanoic acid; 3-(2-benzothiazolylthio)-1-propanesulfonic acid; 1,4-butanediol; 1,3-butanediol; (r,r)-2, 3-butanediol; butanoic acid; l-butane boronic acid; 2-aminon, 3,3-trimethylbutanamide; 4-hydroxy-2-butanone; butyl group; [3-(4-{3-[3-nitro-5-(galactopyranosyloxy)-benzoylamino]-propyl}-piperazin-1-yl)-propylamino]-2-(3-{4-[3-(3-nitro-5-[galactopyranosyloxy]-benzoylamino)-propyl]piperazin-1-yl}; bv2; bv3; bv4; 5-bromovinyldeoxyuridine; bvdu-mp; bromo-willardiine; 2-benzo[,3]dioxol-5-ylmethy 1-3-benzy 1-succinic acid; benzo [b]thiophene-2-boronic acid; 2-(3'-methoxyphenyl) benzimidazole-4-carboxamide; n-benzoyl-n'-beta-d-glucopyranosyl urea; benzofuran; benzimidazole; benzoic acid phenylmethylester; benzene, benzoyl-; benzophenone (Sci); benzoylbenzene; diphenyl ketone; ketone, diphenyl; methanone, diphenyl-(9ci); phenyl ketone; win: rvr; cytidine-5'-monophosphate; undecyl-phosphinic acid butyl ester; tetradecane; n-dodecyl-n,n-dimethyl-3-ammonio-l-propanesulfonate; morpholine-4-carboxylic acid (1-(3-benzenesulfony 1-1-phenethylallylcarbamoyl)-3-methylbutylyamide; 5-methyl-5,6,7,8-tetrahydrofolic acid; cytidine 5'-diphosphoglycerol; 3-chloroalaninate; cytidine-2'-monophosphate; cytidine-3'-monophosphate; cholesterolsulfate; nl-(1-dimethylcarbamoy 1-2-pheny 1-ethyl)-2-oxon4-(2-pyridin-2-yl-ethyl)-succinamide; morpholine-4-carboxylic acid [1-(2-benzylsulfanyl-1-formykethylcarbamoyl)-2-pheny 1-ethyl]-amide; (hydroxyethyloxy)tri(ethyloxy)octane; coa-s-trimethyleneacetyl-tryptamine; coa-s-acetyl 5-bromotryptamine; acetoacetyl-coenzyme a; 4-carboxy-4-aminobutanal; cacodylate ion; hydroxydimethylarsine oxide; camphane; cystein-s-yl cacodylate; 5-exo-hydroxycamphor; camphor; canaline; oxidized coenzyme a; 1,2-dihydroxybenzene; cytosine arabinose-5'-phosphate; s-(dimethylarsenic)cysteine; dodecane-trimethylamine; (2s,4s)-alpha-campholinic acid; carboxymethylenecysteine; acylated ceftazidime; cbl 954; phosphoric acidmono-[5-(4-amino-5-bromo-2-oxo-2h-pyrimidin-1-yl)-3,4-dihydroxy-tetrahydro-furan-2-ylmethyl]; 10-propargyl-5,8-dideazafolic acid; pinacol[[2-amino-alpha-(l-carboxy-1-methylethoxyimino)-4-thiazoleacetyl]amino]methaneboronate; cibacron blue; c-(1-hydrogyl-beta-d-glucopyranosyl) formamide; s-(dcarboxybutyl)-1-homocysteine; cellobiose; clorobiocin; carbenoxolone; 2-{4-[4-(4-chloro-phenoxy)-benzenesulfonyl]-tetrahydro-pyran-4-yl}-n-hydroxy-acetamide; [{(5-chloro-2-pyridinyl)amino}O methylene)-1,1-bisphosphonate; di(n-acetyl-d-glucosamine); n,n-bis(4-chlorobenzyl) lh-1,2,3,4-tetraazol-5-amine; (4-{2-acetylamino-2-[l-(3-carbamoy 1-4-cyclohexylmethoxy-phenyl)-ethylcarbamoylyethyl}-2-phosphono-phenoxy)-acetic acid; {4-[2-acetylamino-2-(3-carbamoyl-2-cyclohexylmethoxy-6,7,8,9-tetrahydro-5h-benzocyclohepten-5ylcarbamoyl) ethyl]-2-phosphono-phenyl}-phosphonic acid; n-cyclopentyl-n-cyclo butylformamide; carbamyl-choline; clorocruoro hem; carboxymethylthio-3-(chlorophenyl)-1,2,4-oxadiazol; butylphosphonate; o5'-(4-(3-{2-[2-((r)-3-hydroxy-4-

(trimethylammonio)-1-oxo-butyl)sulfanyl-ethylcarbamoyl] ethylcarbamoyl}4)-3-hydroxy-2,2-dimethyl-propyl)-1-hydroxy-3-oxido-I,3-dioxo-2,4-dioxa-I,3-diphosphabut-lyl) 3'-phospho-adenosine; crc200 (chiron-behring); carboxymethylated cysteine; 6-(dihydroxy-isobutyl)-thymme; [2-cytidylate-o'-phosphonyloxyl]-ethyl-trimethyl-ammonium; cytidine-5'-diphosphate; methyl 4,6-o-[(Ir)-1-carboxyethylidene]-beta-d-galactopyranoside; d-(1-aaminoadipoyl)-1-cysteiny 1-d-isodehydrovaline; 2c-methyl-derythritol 2,4-cyclodiphosphate; 4-diphosphocytidyl-2-cmethyl-d-erythritol; cardiolipin; 2,3-dideoxyfucose; n-carbamy 1-d-methionine; n-cyclohexyl-n'-decylurea; n-carbamyl-d-valine; icrf-187; 2-chlorodideoxyadenosine; (s)atpa, (s)-2-amino-3-(3-hydroxy-5-tert-butyl-isoxazol-4-yl) propionic acid; cysteine sulfenic acid; degraded cephaloridine; cefotaxime group; 4,6-o-(1-carboxyethylidene)-beta-d-glucose; cephalosporin analog; coelenteramide; hydrolyzed cephalothin; cephalothin group; ethyl-trimethyl-silane; chloro diiron-oxo moiety; 6-chloro-2-fluoropurine; cefoxitin; cytidyl-2'-5'-phospho-guanosine; c-(1-azido-alpha-d-glucopyranosyl) formamide; 5-oxo-pyrrolidine-2-carbaldehyde; 2'-deoxycytidine-2'-deoxyguanosine-3',5'-monophosphate; gamma-carboxy-glutamic acid; chromophore (met-tyr-gly); I-hydroxy-2-amino-3-cyclohexylpropane; cholic acid; 5-chloro-lh-indole-2-carboxylic acid [1-(4-fluorobenzyl)-2-(4-hydroxypiperidinlyl)-2-oxoethyl]amide; chlorophyll b; glycochenodeoxycholic acid; 3-chloro-4-hydroxyphenylglycine; (3s,8ar)-3-(lh-imidazol-5-ylmethyl)hexahydropyrrolo [1,2-a]pyrazine-1,4-dione, ncs-chromophore; cyclohexane; chymostatin; 2-amino-6-chloropyrazine; cilastatin; 4-carboxycinnamic acid; cis-4-cyano-4-[3-(cyclopentyloxy)-4-methoxyphenyl]cyclohexanecarboxylic acid; citric acid; n-cyclohexy 1-n'-(4-iodophenyl)urea; 4-(2,5-dichloro-thiophen-3-yl)-pyrimidin-2-ylamine; 4-(2,4-dimethyl-thiazol-5-yl)-pyrimidin-2-ylamine; n-[4-(2,4-dimethyl-1,3-thiazol-5-yl)pyrimidin-2-yl]-n'-hydroxyimidoformamide; 4-(2,4-dimethyl-thiazol-5-yl)-pyrimidin-2-yl]-(4-trifluoromethyl-phenyl)-amine; 3-[4-(2,4-dimethyl-thiazol-5-yl)-pyrimidin-2-ylamino]-phenol; 4-[4-(4-methyl-2-methylaminothiazol-5-yl)-pyrimidin-2-ylamino]-phenol; [4-(2-amino-4-methyl-thiazol-5-yl)-pyrimidin-2-yl]-(3-nitro-phenyl)-amine; n-(2-aminoethyl)-5-chloroisoquinoline-8-sulfonamide; alpha chlorophyll a; n-methyl-n-[3-(6-phenyl [1,2,4]triazolo[4,3-b]pyridazin-3-yl)phenyl]acetamide; n-{3-[5-(6-amino-purin-9-yl)-3,4-dihydroxy-tetrahydrofuran-2-yl]-allyl}-2,3-dihydroxy-5-nitro-benzamide; chlorophyll a; d-para-chlorophenyl-1-acetamidoboronic acid alanine; n-acetyl-p-nitrophenylserinol; d-para-chlorophenyl-1-acteamidoboronic acid alanine; mdl-29951; alpha-ndichloroacetyl-p-aminophenylserinol; cholesteryllinoleate; chloramphenicol; cholesterol; 3-acetoxymethyl-8-oxo-7-(2-thiophen-2-yl-acetylamino)-5-thia-1-aza-bicyclo[4.2.0]oct-2-ene-2-carboxylic acid; gamma-phenyl-butyric acid; trichloro-acetaldehyde; 5-chloryl-2,4,6-quinazolinetriamine; carboxymycobactin s; carboxymycobactin t; n2-(carboxyethyl)-l-arginine; s,s-(2-hydroxyethyl)thiocysteine; 6-o-cyclohexylmethyl guanine; s-(methylmercury)-1-cysteine; cmp-2-keto-3-deoxy-octulosonic acid; cyclic amp; camp; 5-chloro-6-[(2-iminopyrrolidin-1-yl)methyl]pyrimidine-2,4 (Ih,3h)-dione; carba-nicotinamide-adenine-dinucleotide; co-cyanoco balamin; 5-beta-d-ribofuranosylnicotinamide adenine dinucleotide; acetone cyanohydrin; 1,8-cineole; cyanamide; 2-propenyl-n-acetyl-neuramic acid; 2-(4-chlorophenyl)-5-quinoxalinecarboxamide; hexadecyl octanoate; 2,4-diamino-5-methyl-6-[(3,4,5-trimethoxy-n-methylanilino) methyl]pyrido[2,3-d]pyrimidine; octanoyl-coenzyme a; co-methylcobalamin; dephospho coenzyme a; furo[2,3-d] pyrimidine antifolate; trifluoroacetonyl coenzyme a; 2,4-diamino-6-[n-(2',5'-dimethoxybenzyl)-n-methylamino]quinazoline; protoporphyrin ix contmmng co; 2-oxo-4-methylpentanoic acid; hydrogenobyrinic acid; 2-(oxalylamino)-4, 7-dihydro-5h-thieno[2,3-c]thiopyran-3-carboxylic acid; 2,4-diamino-6-[n-(3',5'-dimethoxybenzyl)-n-methylamino]pyrido[2,3-d]pyrimidine; coenzyme a persulfide; coa-s-acetyl tryptamine; coenzyme a; 1,2-dichloropropane; coproporphyrin iii; cp-526423; 1,2-bis(2-(5-chloroindole-2-carbonylamino)ethoxy)ethane; (2z)-3-{[oxido(oxo)phosphino]oxy}-2-phenylacrylate; cp-271485; (6r)-4-benzyl-6-(1-methyl-2,2-dioxido-1,3-dihydro-2,-benzisothiazol-5-yl) morpholin-3-one; 2'-deoxycytidine-2'-deoxyadenosine-3',5'monophosphate; flavopiridol; I-cyclopropyl-6-fluoro-4-oxo-7-piperazin-1-yl-1,4-dihydroquinoline-3-carboxylic acid; palmitoyl-linoleoyl phosphatidylcholine; coprogen; 2-cyclopropylmethylenepropanal; deoxy-bigchap; 6-chloropurine riboside, 5'-monophosphate; n-cyclohexyl-n'-(propyl) phenyl urea; (s)-2-amino-3-(1,3,5,7-pentahydro-2,4-dioxocyclopenta[e]pyrimidin-1-yl) proional acid; 4-(4-chlorophenyl)imidazole; 1-(2-ethanone)-2-hydroxy-2-(lamino-2-methyl-2-ethanol)-4-(2-dimethyl)ethaneimidazoline-5-one; chromophore (thr-leu-gly); I-deoxy-1-methoxycarbamido-beta-d-glucopyranose; [2-(methyleneamine)-4-(4-hydroxy-benzylidine)-5-oxo-4,5-dihydro-imidazol-1-yl]-acetaldehyde; cra_0433; era_1144; (2r)-2-(aminomethyl)-2,4-dihydroxy-5-oxo-3-(2-oxoethyl)-2,5-dihydro-I h-imidazol-3-ium; I-deoxy-lacetylamino-beta-d-gluco-2-heptulopyranosonamide; era_11092; I-deoxy-I-methoxycarbamido-beta-d-gluco-2-heptulopyranosonamide; carbaphosphonate; capric acid; crotonaldehyde; [2-(l-amino-2-hydroxy-propy 1)-4-(lh-indol-3-ylmethylene)-5-oxo-4,5-dihydro-imidazol-1-yl]-acetaldehyde; 4-{(z)-[2-[3-(methylsulfanyl)propanoyl]-5-oxo-1-(2-oxoethyl)-1, 5-dihydro-4 h-imidazol-4-ylidene] methyl}benzenolate; carboxyethyllumazine; chromophore (gly-tyr-gly); m-cresol; glycerol; carbazole butanoic acid; 3-thiaoctanoyl-coenzyme a; s-acetonylcysteine; cephalosporin c; 3-sulfinoalanine; selenocysteine; n,4-dihydroxyn-oxo-3-(sulfooxy)benzenaminium; s-hydroxycysteine; s-phosphocysteine; s-arsonocysteine; s-mercaptocysteine; cysteine-s-sulfonic acid; double oxidized cysteine; s-oxy cysteine; [4-(4-hydroxy-benzyl)-2-(2-hydroxy-1-methyl-ethyl)-5-oxo-imidazolidin-1-yl] acetic acid; s-selanyl cysteine; (5-chloropyrazolo[I,5-a]pyrimidin-7-yl)-(4-methanesulfonylphenyl)amine; 4-[5-(trans-4-aminocyclohexylamino)-3-isopropylpyrazolo[1,5-a]pyrimidin-7-ylamino]-n,n-dimethylbenzenesulfonamide; cyclotheonamide a; n-2-thiophen-2-yl-acetamide boronic acid; 7-chlorotetracycline; 3-deazacytidine; cytidine; chitotriose; cytidine-5'-triphosphate; cellotriose; (1 s,6s,7r,8r,8ar)-1,6,7,8-tetrahydroxyindolizidine; cellotetraose; 8-benzyl-2-hydroxy-2-(4-hydroxybenzyl)-6-(4-hydroxy-phenyl)-2h-imidazo[1,2-a]pyrazin-3-one; (mu-4-sulfido)-tetranuclear copper ion; 4-(carboxyvin-2-yl)phenylboronic acid; crystal violet; phenylalanine-nsulfonamide; pentaethylene glycol monodecyl ether; cyclohexylformamide; cyclohexanol; n-carboxymethionine; [3-(o-chlorophenyl)-5-methyl-4-isoxazolyl]penicillin; cyclohexane propionic acid; 3-cyclohexyl-1-propylsulfonic acid; carboxyatractyloside; cytidine-5'-diphospho-beta-dxylose; 2-amino-3-mercaptopropionamide; s-butyryl-cystein; cyclohexanone; s-methyl phosphocysteine; calyculin a; (3-formyl-but-3-enyl)-phosphonic acid; 3-bicyclo[2.2.1] hept-5-en-2-yl-6-chloro-3,4-dihydro-2h-1,2,4-benzothiadiazine-7-sulfonamide 1, 1 dioxide; thiarsa dihydroxy cysteine; br-coeleneterazine; 8-benzyl-2-hydroperoxy-2-(4-hydroxy-benzyl)-6-(4-hydroxy-phenyl)-2h-imidazo[1,2-a]pyrazin-3-one; i-coeleneterazine; n-coeleneterazine; cp-coeleneterazine; thiarsahydroxy-cysteine; decane; dodecane; zd 1694; (4s,5s)-I,2-dithiane-4,5-diol; 2-[4-(2,4-dichlorophenoxyl) phenoxy] propanoic acid; (2r)-amino(3,5-dihydroxyphenyl) acetic acid; 2',3'-dehydro-2',3'-deoxy-thymidine 5'-diphosphate; (2s)-amino(4-hydroxyphenyl)acetic acid; 2',3'dehydro-2',3'-deoxy-thymidine 5'-triphosphate; 2-deoxyglucose-6-phosphate; 2-deoxy-d-glucitol 6-(e)vinylhomophosphonate; adma; 2,4-diaminobutyric acid; 2-decenoyl n-acetyl cysteamine; 2',3'-dideoxyadenosine-5'triphosphate; 1,4-deoxy-4-((5-hydroxymethyl-2,3,4-trihydroxycyclohex-5-enyl) amino)fructose; 4,6-dideoxy-4-amino-beta-d-glucopyranoside; 3,4-dihydroxyphenylalanine; 4-(n,n-dimethylamino) cinnamoyld-alanine; n-methyl-alpha-beta-dehydroalanine; 2-deoxy-2, 3-dehydro-n-acetyl-neuraminic acid; lauric acid; d-arginine; d-aspartic acid; 2deoxy-thymidine-5'-diphospho-alpha-dglucose; delta-amino valeric acid; 5-bromo-n[2-(dimethylamino)ethyl]-9-aminoacridine-4-carboxamide; trencam-3, 2-hopo; 7-(1,1-dioxo-lh-benzo[d]isothiazol-3-yloxymethyl)-2-(oxalyl-amino)-4, 7-dihydro-5h-thieno[2,3-c]pyran-3-carboxylic acid; dibenzofuran-4,6-dicarboxylic acid; 2,3-dihydroxy-benzoic acid; deglucobalhimycin; 9-(6-deoxy-beta-d-allofuranosyl)-6-methylpurine; debromohymenialdisine; adamantane-1-carboxylic acid-5-dimethyl-amino-naphthalene-1-sulfonylamino-butyl-amide; 2,3, dihydroxybenzoylserine; z-dehydrobutyrine; 3-(benzoylamino)-1-alanine; desulfo-coenzyme a; 2',4'-dinitrophenyl-2deoxy-2-fluro-b-d-cellobioside; dodecyl-coa; diethylcarbamodithioic acid; ethylene dichloride; 2'-deoxycytidine-5'-monophosphate; diclosan; 3,3-dichloro-2-phosphonomethyl-acrylic acid; 2'-deoxycytidine-5'-triphosphate, d-pyridoxyl-n,o-cycloserylamide-5-monophosphate; d-cysteine; 2'-deoxycytidine; 5,4'-dideoxyflavanone; diphthamide; 2-(3-carboxyamido-3-(trimethylammonio)propyl) histidine; 5,10-dideazatetrahydrofolic acid; diacetyldeuteroheme; 1,5-dideoxy-1,5-imino-d-mannitol; ((2r,3s,5r)-3-hydroxy-5-(4-hydroxy-2-oxo-3,4-dihydropyrimidin-1 (2h)yl)-tetrahydrofuran-2-yl)methyldihydrogen phosphate; 6-hydroxy-d-norleucine; 2,4-diamino-4,6-dihydroxypyrimidine; decylamine-n,n-dimethyl-n-oxide; n,o-didansyl-1-tyrosine; 2'-5'dideoxyuridine; d-eritadenine; 6-deoxyerythronolide b; 2-dimethylamino-ethyl-diphosphate; 3,5-dimethyl-1 h-pyrazole-4-carboxylic acid ethyl ester; desferal; 4-deoxylactose; decyloxy-methanol; indene; 2-[2-(1,3-dioxo-I,3-dihydro-2h-isoindol-2-yl)ethyl]-4-(4'ethoxy-I, 1'-biphenyl-4-yl)-4-oxobutanoic acid; diethyiphosphono group; dequadin; d-4-phosphoerythronic acid; diethylstilbestrol; co(iii)-(deuteroporphyrin ix); 4-phosphod-erythronate; diphenylacetic acid; 2,3-difluorobenzyl alcohol; 4'-hydroxyflavanone; 3-[3-(2,3-dihydroxy-propylamino)-phenyl]-4-(5-fluoro-1-methyl-1 h-indol-3-yl)pyrrole-2,5-dione; diisopropylphosphono group; 5-deoxyflavanone; 2-deoxy-glucitol-6-phosphate; d-glucuronic acid; digalactosyl diacylglycerol (dgdg); I-[glycerolylphosphonyl]-2-[8-(2-hexyl-cyclopropyl)-octanal-1-yl]-3-[hexadecanal-1-yl]-glycerol; (2r)-amino(4-hydroxyphenyl) acetic acid; 2'-deoxyguanosine-5'-diphosphate; d-glutamic acid; d-glutamine; 2'-deoxyguanosine-5'-monophosphate; 3,6-anhydro-d-galactose-2-sulfate; 2'-deoxyguanosine-5'triphosphate; (2s, 3s)-trans-dihydroquercetin; 2,3-didehydroalanine; 3,4-dihydroxybenzoic acid; 3,4-dihydroxycinnamic acid; heme d; dihydrofolic acid; 3-dehydroshikimate; 2,6-dimethyl-7-octen-2-ol; 5-hydroxy norvaline; deoxycholic acid; 3-decyl-2,5-dioxo-4-hydroxy-3-pyrroline; 3,4-dihydro-5-methy 1-isoquinolinone; (2s)-hydroxy(4-hydroxyphenyl)ethanenitrile; 3-amino-4,5-dihydroxy-cyclohex-1-enecarboxylate; dihydrotestosterone; 2-(3,4-dihydroxyphenyl)acetic acid; 1,8-diaminooctane; octamethylenediamine; 1,8-octanediamine; 3,4-dichioroisocoumarin; 4,4'[1,6-hexanediylbis (oxy)]bisbenzenecarboximidamide; 2,5-dideoxy-2,5-imino-d-glucitol; 4'-deaza-l'aza-2'-deoxy-l'-(9-methylene)-immucillin-h, (3r,4r)-n-[9-deazahypoxanthin-9-yl)methyl]-4-hydroxymethylpyrrolidin-3-ol; methylphosphonic acid diisopropyl ester; 1,4-diethylene dioxide; dinor-n(omega)-hydroxy-1-arginine; disordered solvent; d-isovaline; dcka, 5,7-dichlorokynurenic acid; decanoic acid; 4-[2-(3-benzyloxycarbonylamino-4-cyclohexyl-1-hydroxy-2-oxo-butylamino)-5-guanidino-pentanoylamino]-4-(1-carboxy-2-cyclohexy 1-ethylcarbamoyl)butyric acid; d-lactic acid; d-leucine; 2-hexyloxy-6-hydroxymethyl-tetrahydro-pyran-3,5-diol; di-linoleoyl-3-sn-phosphatidylcholine; d-lysine; dimethylallyl diphosphate; 5,6-dimethylbenzimidazole; dimethylformamide; dimethylglycine; 2,3-dimethylimidazolium ion; 1-deoxymannojirimycin; terminal dimethyl; alpha-difluoromethylornithine; dmp450 (inhibitor of dupont merck); dimethyl sulfoxide; 2,3-dihydroxy-valerianic acid; 3,5-dinitrocatechol; deamidonad+; 2,4-dinitrophenol; 1-deoxy-nojirimycin; 7,8-diaminononanoic acid; 3-amino-alanine; dnqx; 2-amino-6-oxo-hexanoic acid; 2,4-dihydroxybenzoic acid; 2',3'dideoxycytidine-5'-monophosphate; 4-(3, 12, 14-trihydroxy-10, 13-dimethy 1-hexadecahydro-cyclopenta[a]phenanthren-17-yl)-5h-furan-2-one; beta-hydroxy aspartic acid; dalfopristin; 2'-deoxymaltose; domoic acid; dihydroorotic acid; delta-bis(2,2'-bipyridine)imidazole osmium (ii); 1-n (omega)-nitroarginine-2,4-1-diaminobutyric amide; n-{(4s)-4-amino-5-[(2-aminoethyl)amino]pentyl}-n'-nitroguanidine; 1-n(omega)-nitroarginine-(4r)-amino-l-proline amide; dpb-t; dipyrromethane cofactor; d-phenylalanine; diphosphate; d-proline; 3-(lh-indol-3-yl)-2-[4-(4-phenyl-piperidin-1-yl)-benzenesulfonylamino]-propionic acid; 4, 7-dimethyl[1,1 O]phenanthroline; mixed carbamic phosphoric acid anhydride of 7,8-diaminononanic acid; 3,5-diaminophthalhydrazide; 3-dehydroquinic acid; duroquinone; 1-(2,6-dichlorophenyl)-5-(2,4-difluorophenyl)-7-piperazin-1-y 1-3, 4-dihydroquinazolin-2(1h)-one; 2,6-diaminoquinazolin-4 (3h)-one; 11-deoxy-beta-rhodomycin; delta-bis(2,2'bipyridine)-(5-methyl-2-2'-bipyridine)-c9-adamantane ruthenium (ii); 5,6-dihydro-benzo[h] cinnolin-3-ylamine; delta-bis(2,2'-bipyridine)imidazole ruthenium (ii); 4,7-dioxosebacic acid; 7-(carboxyamino)-8-amino-nonanoic acid; d-asparagine; d-serine; adamantane-1-carboxylic acid-5-dimethylamino-naphthalene-1-sulfonylamino-octyl-amide; methyl methylsulfinylmethyl sulfide; dimethylallyl s-thiolodiphosphate; d-dethiobiotin; bishydroxy[2h-1-benzopyran-2-one,1,2-benzopyrone]; dithiane dial; 4-[(10s,14s,18s)-18-(2-amino-2-oxoethyl)-14-(1-naphthylmethyl)-8, 17,20-trioxo-7,16, 19-triazaspiro [5.14]icos-I 1-en-10-yl]benzylphosphonic acid; d-threonine; d-treitol; 2,4-diamino-6-[n-(3',4', 5'-trimethoxybenzyl)-n-methylamino]pyrido [2,3-d]pyrimidine; 2'-deoxyadenosine 5'-triphosphate; 4-[3-hydroxyanilino]-6, 7-dimethoxyquinazoline; d-tryptophan; 1,4-dithiothreitol; (2r,3s)-1,4-dimercaptobutane-2,3-diol; (2s,3s)-1,4-dimercaptobutane-2, 3-diol; 4-(3,14-dihydroxy-10, 13-dimethy 1-hexadecahydro-cyclopenta[a]phenanthren-17-yl)-5h-furan-2-one; d-tyrosine; 3,4-dihydrouracil; deoxyuridine-5'-diphosphate; 2,4(1h,3h)-pyrimidinedione,l-[2-deoxy-5-o-[hydroxy(phosphonoamino)phosphinyl]-beta-derythropentofuranosyl]-; 2'-deoxyuridine 5'-alpha,betaimidotriphosphate; 2'-deoxyuridine; deoxyuridine-5'triphosphate; d-valinexvigaxaxvxwxwxwxwx; 3-(4-carbamoyl-1-carboxy-2-methylsulfonyl-buta-1,3-dienylamino)-indolizine-2-carboxylic acid; desvancosaminyl vancomycin; 1,2- hydro-1-oxy-3,4-hydro-3-(l-methoxy-2-oxy-3,4-dihydroxypentyl)-8,9-dihydroxy-7-(sec-butyl)-anthracene; 1,2-dimethoxyethane; 4-deoxyglucarate; I-deoxy-d-xylulose-5-phosphate; methylmalonic acid; 4-(1,3,2-dioxaborolan-2-yloxy)butan-l-aminium; 4',7-dihydroxyisoflavone; 7-o-b-d-glucopyranoside; 3-hydroxymethyl-5-aziridinyl-lmethyl-2-[Ih-indole-4, 7-dione]propanol; ethyl oxo(piperidin-1-yl)acetate; prostaglandin b2; compound 4-d; erythose-4-phosphate; n-[n-[1-hydroxycarboxyethy 1-carbonyl]leucylamino-butyl]-guanidine; n[1-hydroxycarboxyethy 1-carbonyl]leucylamino-2-methyl-butane; 1,n6-ethenoadenine; 2-amino-vinyl-phosphate; 5-{2-[I-(6-ethyl-6-hydroxy-1-methyl-octa-2,4-dienyl)-7a-methyl-octahydro-inden-4-ylidene]-ethylidene}-4-methylene-cyclohexane-1,3-diol; 22-24-diene-24a,26a,27a,trihomo-I alpha, 25-dihydroxyvitamin d3; 3,4-epoxybutyl-alpha-dglucopyranoside; diethyl 4-methylbenzylphosphonate; ethylene glycol; {[-(bis-carboxymethyl-amino)-ethyl]-carboxymethyl-amino}-acetic acid; ethyl dihydrogen phosphate; amino di(ethyloxy)ethylaminocarbonylbenzenesulfonamide; ethylene glycol; epigallocatechin; n-(I-benzyl-3-{[3-(1,3-dioxo-1,3-dihydro-isoindol-2-yl)-propionyl]-[2-(hexahydro-benzo[I,3]dioxol-5-yl)-ethyl]-amino}-2-hydroxy-propyl)-4-benzyloxy-3,5-dimethoxy-benzamide; 3-hydroxyphenylalanine; 4-hydroxy-3-methyl butyl diphosphate; 1,3-di(n-propyloxy-a-mannopyranosy 1)-carbomyl 5-methyazido-benzene; elaidoylamide; methyl-carbamic acid ethyl ester; 5-[1-(3,4-dimethoxy-benzoyl)-1,2,3,4-tetrahydro-quinolin-6-yl]-6-methy 1-3, 6-dihydro-[1,3,4]thiadiazin-2-one; emodin; n-aminoethylmorpholine; 2-(ethyl-mercuri-thio)-benzoic acid; etheno-nad; ethyl isocyanide; hpp; etheno-nadp; epothilone b; epothilone d; 1-alpha-phosphatidyl-beta-oleoyl-gamma-palmitoyl-phosphatidyletha-nolamine; heptanyl-p-phenol; I-hydroxy-2-s-glutathionyl-3-para-nitrophenoxy-propane; equilin; equilenin; ergosterol; 4-methoxy-e-rhodomycin t; ethanesulfonic acid; 4-iodo-benzo[b]thiophene-2-carboxamidine; 1,3,5(1 O0)-estratriene-3, 16, 17-triol; 2-methoxyestradiol; thieno[2,3-b]pyridine-2-carboxamidine; benzo[b]thiophene-2-carboxamidine; ethanolamine; 2-{2-[2-2-(methoxy-ethoxy)-ethoxy]-ethoxy}-ethanol; trifluoroethanol; 2-(trimethylammonium) ethyl thiol; methylethylamine; 3-(4-benzenesulfonylthiophene-2-sulfonylamino)-phenyl-boronic acid; n-ethyl retinamide; (4s-trans)-4-(ethylamino)-5,6-dihydro-6-methyl-4h-thieno(2,3-b)thiopyran-2-sulfonamide-7, 7-dioxide; 2-ethoxyethanol; 2-methoxy-4-vinyl-phenol; nonan-1-ol; tricosanoic acid; 1,6-di-o-phosphono-d-allitol; coenzyme f420; n-(2,6-diflouro-benzyl)-4-sulfamoyl-benzamide; fructose-6-phosphate; fructose-6-phosphate; 2,3-anhydro-quinic acid; 5-(6-amino-9h-purin-9-yl)-4-hydroxytetrahydrofuran-3-yl dihydrogen phosphate; 2-anhydro-3-fluoro-quinic acid; 3-hydroxyimino quinic acid; flavin-adenine dinucleotide-n5-isobutyl ketone; hexafluoroacetone hydrate; flavin-adenine dinucleotide; flavin-n7 protonated-adenine dinucleotide; 1-hexyldecanoic acid; 4-fluorobenzylamine; fructose-1,6-diphosphate; 4-flourobenzenesulfonamide; 2,6-difluorobenzenesulfonamide; 3,5-difluoro benzenesulfonamide; thiocoumarin; alpha-d-fucose; beta-d-fucose; 5-(2-chlorophenyl) furan-2-carboxylic acid; ferricrocin-iron; 1,2-epoxypropylphosphonic acid; alpha, alpha,alpha-trifluoro-pcresol; deoxy-2-fluoro-b-d-cellotrioside; alpha-fluorocarboxymethyldethia coenzyme a complex; free cysteine; n-alpha-(2-naphthylsulfonyl)-n-(3-amidino-l-phenylaninyl)-d-pipecolinic acid; n-alpha-(2-naphthylsulfonyl)-n(3-amidino-l-phenylalaninyl)isopipecolinic acid methyl ester; n-alpha-(2-naphthylsulfonyl)-n(3-amidino-l-phenylalaninyl)-4-acetyl-piperazine; phosphoric acid mono-[3-fluoro-5-(5-methyl-2,4-dioxo-3,4-dihydro-2h-pyrimidin-1-yl)-tetrahyro-furan-2-ylmethyl] ester; d-gluco-2,5-anhydro-ldeoxy-l-phosphonohexitol-6-phosphate; 7-(1-methyl-1,2,3-triazol-4-yl)-6-formyl-2, 7-dihydro-[1,4]thiazepine-3-carboxylic acid, br142715, c6-(nl-methyl-1,2,3-triazolylmethylene)penem; monoazido-mu-oxo-diiron; n-(2-ferrocenylethyl)maleimide; n-(4-hydroxyphenyl)all-trans retinamide; [(4-{4-[4-(difluoro-phosphono-methyl)-phenyl]-butyl}-phenyl)-difluoro-methyl]-phosphonic acid; fexaramine; n-(2,3,4,5,6-pentaflouro-benzyl)-4-sulfamoyl-benzamide; trifluorofumesyl diphosphate; 5-formyl-6-hydrofolic acid; n-[4-(2-{2-[3-(2-bromo-acetylamino)propionylamino]-3-hydroxy-propionylamino}-ethyl)phenyl]-oxalamic acid; 2-aminopropanedioic acid; 2-amino-3-hydroxy-3-phosphonooxy-propionic acid; (e)-2-fluoro-phydroxycinnamate; fidarestat; filaminast; fidarestat (stereoisomer); fidarestat (stereoisomer); k506; flurbiprofen methyl ester; 6,4'-dihydroxy-3-methyl-3',5'-dibromoflavone; trifluoroalanine; furoyl-leucine; flufenamic acid; fluoresceinylthioureido; methanal, oxomethane, oxymethylene, methylene oxide,formic aldehyde, methyl aldehyde; 3-fluoro-2-methylaniline; fluorescein; 2,5,7-trihydroxynaphthoquinone; n-[(furan-2-yl)carbonyl]-(s)-leucyl-(r)-[1-amino-2(1 h-indol-3-yl) ethyl]-phosphonic acid; n7-methyl-formycina; 6-methyl-formycina; formycin b; formycin; 4-((3r,4s,5r)-4-amino-3, 5-dihydroxy-hex-1-ynyl)-5-fluoro-3-[1-(3-methoxy-lh-pyrrol-2-yl)-meth-(z)-ylidene]-1,3-dihydro-indol-2-one; n-formylmethionine; 2-deoxy-2-fluoro-alpha-d-mannosyl fluoride; n-{3-chloro-4-[(3-fluorobenzyl)oxy]phenyl}-6-[5-({[2-(methylsulfonyl)ethyl] amino}methyl)-2-furyl]-4-quinazolinamine; riboflavin monophosphate; formycin-5'-monophosphate; fumarate; formic acid; 5-aminocarbonyl-3-nitrophenyl-alpha-d-galactopyranose; {[7-(difluoro-phosphono-methyl)-naphthalen-2-yl]-difluoro-methyl}-phosphonic acid; n-sulfo-flavin mononucleotide; fucitol; farnesol; forskolin; fosmidomycin; 5-formyl-5,6,7,8-tetra-hydrofolate; f-loop of vitamin b12; [[n(benzyloxycarbonyl)amino]methyl]phosphate; d-fructose-6-phosphate (open form); 3-fluoro-2-(phosphonooxy)propanoic acid; 3-(4-fluorophenyl)-1-hydroxy-2-(pyridin-4-yl)-lh-pyrrolo[3,2-b]pyridine; n-formylpiperidine; fluorophosphite ion; 5-fluoro-4-(s)-hydroxy-3,4-dihydropyrimidine; frl 17016; 2-[4-[[(s)-1-[[(s)-2-[[(rs)-3,3, 3-trifluoro-1-isopropy 1-2-oxopropyl] aminocarbonyl] pyrrolidin-1-yl-]carbonyl]-2-methylpropyl] aminocarbonyl]benzoylamino]acetic acid; fr221647; fr230513; fr233623; fr239087; fr236913; sp2456; feruloyl coenzyme a; (r)-n-[2-[1-(aminoiminomethyl)-3-piperidinyl]-1-oxoethyl]-4-(phenylethynyl)-1-phenylalanine methylester; 5-[2,3-dichloro-4-(5-{I-[2-(2-guanidino-4-methyl-pentanoylamino)-acetyl]piperidin-4-yl}-1-methyl-lh-pyrazol-3-yl)phenoxymethyl]-furan-2-carboxylic acid; sp4160; 3-(3,5-dibromo-4-hydroxy-benzoyl)-2-ethyl-benzofuran-6-sulfonic acid [4-(thiazol-2-ylsulfamoyl)-phenyl]-amide; 2-{3-[4-(4-fluorophenyl)-3,6-dihydro-I (2h)-pyridinyl]propyl}-8-methyl-4(3h)-quinazolinone; fructose; n-(2-flourobenzyl)-4-sulfamoyl-benzamide; fusicoccin; 3-fluorosialic acid; [1-(4-fluorobenzyl)cyclobutyl]methyl (1 s)-1-[oxo(lhpyrazol-5-ylamino)acetyl]pentylcarbamate; 3-(4-phenylamino-phenylamino)-2-(1 h-tetrazol-5-yl)-acrylonitrile; 1-(2-fluorobenzyl)-3-butyl-8-(n-acetyl-4-amino-benzyl)xanthine; trifluoro-thiamin phosphate; fluorotryptophane; 3-hydroxy-myristic acid; fusidic acid; fucose; fumagillin; 6-deoxy-beta-1-galactose; fumaric acid; fudp; fluoro-willardiine; flea; n-1-methylheptylformamide; 4-[5-pyridin-4-yl-1 h-[1,2,4]triazol-3-yl]-pyridine-2-carbonitrile; alpha-d-glucose 1,6-bisphosphate; alpha-d-glucose-1-phosphate; 4-acetyl-4-guanidino-6-methyl(propyl)carboxamide-4,5-dihydro-2h-pyran-2-carboxylic acid; gc-24; 5-n-acetyl-4-amino-6-diethylcarboxamide-4, 5-dihydro-2h-pyran-2-carboxylic acid; 2-deoxy-2fluoro-glucose; glycerol-2-phosphate; phosphomethylphosphonic acid guanylate ester; 5-n-acetyl-3-(1-ethylpropyl)-1-cyclohexene-l-carboxylic acid; guanosine-3'-monophosphate-5'-diphosphate; glyceraldehyde-3-phosphate; 3-phosphoglycerol; 8-oxo-2'-deoxyguanosine-5'-monophosphate; 4-deoxy-alpha-d-glucose; guanosine-5',3'-tetraphosphate; d-galactose-4-sulfate group; 6-deoxy-alpha-d-glucose; alpha-d-glucose-6-phosphate; glucose-6-phosphate; n7-methyl-guanosine-5'-monophosphate; 9-(1,3-dihydroxy-propoxymethane)guanine; metanitrophenyl-alpha-d-galactoside; gabaculine; dihydro-acarbose; 2,6-anhydro-3-deoxy-d-erythro-hex-2-enonic acid; 3-hydroxyisoxazole-4-carboxylic acid; guanidine; glycinamide ribonucleotide; p-aminophenyl-alpha-d-galactopyranoside; 4-hydroxy-1,2,5-thiadiazole-3-carboxylic acid; s-(3-iodo benzyl)glutathione; s-(n-hydroxy-nbromophenylcarbamoyl)glutathione; 4-guanidinobenzoic acid; 4-deoxy-d-glucuronic acid; I-guanidinium-7-aminoheptane; 4,5-dehydro-d-glucuronic acid; trypanothione; n-cholylglycine; 3-deoxy-d-glucosamine; gluconic acid; gallichrome; 2-amino-2-deoxy-d-glucose; 4,5-dihydroxy-tetrahydro-pyran-2-carboxylic acid; 4-o-methyl-alpha-d-glucuronic acid; 4-o-methyl-beta-d-glucuronic acid; 4-deoxy-4-amino-beta-d-glucose; 1-(s-glutathionyl)-2,4-dinitrobenzene; 2-acetamido-2-deoxy-d-glucono-1,5-lactone; geldanamycin; glutathione s-(2,4 dinitrobenzene); guanosine-5'-diphosphate; guanosine-5'-diphosphate-rhamnose; oxidized glutathione disulfide; udp-d-galactopyranose; guano sine 5'-(trihydrogen diphosphate), p'-d-mannopyranosyl ester; ge2270a; (4e)-4-aminohex-4-enoic acid; I-o-octyl-2-heptylphosphonyl-sn-glycero-3-phosphoethanolamine; 2-guanidinoethylthio)succinic acid; guanidinoethylmercaptosuccinic acid; gemsa; 5, 7-dihydroxy-3-(4-hydroxyphenyl)-4h-1-benzopyran-4-one; 4',5, 7-trihydroxyisoflavone; prunetol; genisteol; genz-10850; geran-8-yl geran; g418; 1-2-amino-4-(guanidinooxy)butyric acid; 1-menaphthyl glutathione conjugate; beta-i 1,2,3,4,6-penta-o-galloyl-d-glucopyranose; ghavamiol; 4-hydroxyphenylglycine; (8ar)hexahydropyrrolo[1,2-a]pyrazine-1,4-dione; s-(n-hydroxyn-iodophenylcarbamoyl)glutathione; glucarate; alpha-dgalactose-1-phosphate; 3-amino-8,9, 10-trihydroxy-7-hydroxymethyl-6-oxa-1,3-diaza-spiro[4.5] decane-2,4-dione; 8,9, 10-trihydroxy-7-hydroxymethyl-2-thioxo-6-oxa-1,3-diaza-spiro[4.5]decan-4-one; 3,8,9, 1 O-tetrahydroxy-7-hydroxymethyl-6-oxa-1,3-diaza-spiro [4.5]decane-2,4-dione; (3,4,5-trihydroxy-6-hydroxymethyl-tetrahydropyran-2-yl)-phosphoramidic acid dimethyl ester; 8,9,10-trihydroxy-7-hydroxymethyl-3-methyl-6-oxa-1,3-diazaspiro[4.5]decane-2,4-dione; (4ar,6s,8ar)-II-[8-(1,3-dioxo-I, 3-dihydro-2h-isoindol-2-yl)octyl]-6-hydroxy-3-methoxy-5, 6,9, 1 O-tetrahydro-4ah-[1]benzofuro[3a,3,2-ef] [2] benzazepin-11-ium; n-(8,9,1 O-trihydroxy-7-hydroxymethyl-2,4-dioxo-6-oxa-I,3-diaza-spiro[4.5]dec-3-yl-acetamide; glucose; 4,6-dideoxyglucose; alpha-d-glucopyranosyl-2-carboxylic acid amide; skf 107457; glycoluril; d-glucose inlinear form; glucosamine 6-phosphate; 2,3-dihydroxy-5-oxohexanedioate; beta-d-glucopyranose spirohydantoin; glyoxalate, glyoxylate; 6-deoxyglucose; glycinamid; gm6001; 4-amido-4-carbamoyl-butyric acid; 1-glycero-dmanno-heptopyranose; gallamine; guanosine; 2,4-deoxy-4-guanidino-5-n-acetyl-neuraminic acid; s-p-nitrobenzyloxycarbonylglutathione; aminophosphonic acid guanylate ester; 2-(3,4-dihydro-3-oxo-2h-benzo[b] [1,4]thiazin-2-yl)-n-hydroxyacetamide; (−)-galanthamine; hydroxyacetic acid; hydroxyethanoic acid; d-gluconhydroximo-1,5-lactam; glucosamine I-phosphate; phosphomethylphosphonic acid guanosyl ester; diguanosine-5'-triphosphate; glucosamine 4-phosphate; 1-(4-amidinophenyl)-3-(4-chlorophenyl)urea; 1-(2-amidinophenyl)-3-(phenoxyphenyl)urea; 1-alpha-glycerophosphorylethanolamine; gpi-1046; glyphosate; geranyl diphosphate; (9r, 1 Or)-9-(s-glutathionyl)-1O-hydroxy-9,10-dihydrophenanthrene; (9s, 1 Os)-9-(s-glutathionyl)-1 O-hydroxy-9, 10-dihydrophenanthrene; guano sine 5'-diphosphate 2':3'-cyclic monophosphate; 1-thio-beta-d-glucopyranose; 4-thio-beta-d-glucopyranose; o4-sulfonyl-galactose; s-benzyl-glutathione; 4-thio-d-glucose; 1-alpha-glycerophosphorylserine; gluthathione; 5'-guanosine-diphosphate-monothiophosphate; 7-methyl-gpppa; s-(p-nitrobenzyl)glutathione; mrna cap analog n7-methyl gpppg; d-galactohydroximo-1,5-lactam; ol-methyl-4-deoxy-4-thio-beta-d-glucose; phosphoaminophosphonic acid guanylate ester; phosphomethylphosphonic acid-guanylate ester; guanosine-5'-triphosphate; galacturonic acid; glutathione sulfonic acid; s-hexylglutathione; s-octylglutathione; (Sr, 6s, 7s, 8s)-5-hydroxymethyl-6,7,8-trihydroxy-tetrazolo[1,5-a] piperidine; 2-amino-7-[2-(2-hydroxy-1-hydroxymethyl-ethylamino)-ethyl]-I, 7-dihydro-purin-6-one; glutaric acid; glucose-uridine-cl,5'diphosphate; 5-fluoro-beta-1-gulosyl fluoride; 4-methylumbelliferyl chitobiose; guanine; heparin disaccharide i-s; (6r, 7r)-3-[(acetyloxy)methyl]-7-{[(6s)-6-(glycylamino)-7-oxido-7-oxoheptanoyl] amino}-8-oxo-5-thia-I-azabicyclo[4.2.0]octane-2-carboxylate; quinonoid 7,8-tetrahydrobiopterin; heptulose-2-phosphate; heparin disaccharide iii-s; 5, 10-dimethylene tetrahydromethanopterin; I-deoxy-6-o-phosphono-I-[(phosphonomethyl) amino]-1-threo-hexitol; hydantocidin-5'-phosphate; 9-(5,5-difluoro-5-phosphonopentyl)guanine; beta-cyclohexylalanine; (carboxyhydroxyamino)ethanoic acid; acetohydroxamic acid; gshna; cyclohexylammonium ion; histidyl-adenosine monophosphate; n-omega-hydroxy-1-arginine; hydroxyaminovaline; p-hydroxybenzaldehyde; n-[2-hydroxy-2-(8-isopropyl-6,9-dioxo-2-oxa-7, 1 O-diazabicyclo [ll.2.2]heptadeca-I (16),13(17), 14-trien-11-yl)ethyl]-n-(3-methyl-butyl)-benzenesulfonamide,inhibitor 3; 2-(11-{2-[benzenesulfonyl-(3-methyl-butyl)-amino]-1-hydroxy-ethyl}-6,9-dioxo-2-oxa-7,10-diaza-bicyclo[ll.2.2] heptadeca-I (16),13(17), 14-trien-8-yl)-acetamide, inhibitor 2; 7,8-dihydrobiopterin; 7,8-dihydro-l-biopterin; I-histidine beta naphthylamide; 2,4-dihydroxy-7-(methyloxy)-2h-1,4-benzoxazin-3(4h)-one; r,3-hydroxybutan-2-one; s,3-hydroxybutan-2-one; 4-[hydroxy[methyl-phosphinoyl]]-3-oxo-butanoic acid; para-coumaric acid; 2',4,4'-trihydroxychalcone; 3pp; 3-phenylpropionic acid; 2-acetyl-protoporphyrin ix; 2-amino-4-mercapto-butyric acid; hadacidin; 3r-hydroxydecanoyl-coa; heme; dimethyl propionate ester heme; methylhydrazine; 1-hexadecanosulfonic acid; 4-[(4-imidazo[1,2-a] pyridin-3-ylpyrimidin-2-yl) amino]benzenesulfonamide; n-[4-(2-methylimidazo[I,2-a] pyridin-3-yl)-2-pyrimidinyl] acetamide; 2-{(9as)-9a-[(1 s)-1-hydroxyethyl]-2,7-dimethyl-9a, 1 O0-dihydro-5h-pyrimido[4,5-d] [1,3]thiazolo[3,2-a]pyrimidin-8-yl}ethyl trihydrogen di phosphate; 6, 7-dicarboxyl-1, 2,3,4,5,8-hexamethylhemin; hybrid between b and c type hemes (protoporphyrin ixcontaining fe); heme c; 2-hydroxyethyl disulfide; n-hexylphosphonate ethyl ester; (2s,5r,6r)-6-{[(6r)-6-(glycylamino)-7-oxido-7-oxoheptanoyl]amino}-3, 3-dimethyl-7-oxo-4-thia-1-azabicyclo [3.2.O]heptane-2-carboxylate; heme; 2-[(3-hydroxy-2-methyl-5-phosphonooxymethyl-pyridin-4-ylmethyl)-imino]-5-phosphonopent-3-enoic acid; zinc substituted heme c; 1,3-dedimethyl- 1,3-divinyl heme; hexane; hexane-1,6-diol; alpha-hydroxy-beta-phenyl-propionic acid; 5-(3,3-dihydroxypropeny)-3-methoxy-benzene-1,2-diol; 2-fanny 1-protoporphryn ix; hg9a-9, nonanoyl-n-hydroxyethylglucamide; glutamine hydroxamate; 4-(hydroxymercury)benzoic acid; methyl mercury ion; mercury diiodide; n-hydroxyguanidine; [pterin-6-ylmethanyl]-phosphonophosphate; (2s,3s)-trans-2,3-dihydro-3-hydroxyanthranilic acid; I-monohexanoyl-2-hydroxy-sn-glycero-3-phosphate; (2s)-2, 8-diaminooctanoic acid; 6-hydroxymethy 1-7, 8-dihydropterin; 6-hydroxymethylpterin; 4-methyl-histidine; fe-mesopone; (8,12-diethyl-3,8, 13, 17-tetramethyl-7-oxo-porphyrinato-2, 18-dipropionic acid)iron(iii); 2-methyl-3-(2-aminothiazolo)propanal; n-hydroxy-n-isopropyloxamic acid; ndl-phosphonohistidine; 2-bromo-2-chloro-I, 1, 1-trifluoroethane; beta-hydroxyleucine; 5-hydroxymethyl-chonduritol; hymenialdisine; (s)hmg-coa; 4-amino-5-hydroxymethyl-2-methylpyrimidine; isoformononetin; I-hydroxyamine-2-isobutylmalonic acid; 1,8-di-hydroxy-4-nitro-anthraquinone; hydantocidin-5'monophosphate; 2,3-propandiol; hypoxanthine; 2-hydroxy-3-amino-4-phenyl butane; open form of 2'-deoxy-ribofuranose-5'-phosphate; n-(I-carboxy-3-phenylpropyl) phenylalanyl-alpha-asparagine; n-heptylformamide; heptanamide; hydroxyphenyl propionic acid; 6-hydroxy-7, 8-dihydro purine nucleoside; phenyiphosphate; 6-hydroxy-propyithymine; 4-hydroxy-3,4-dihydro-I h-pyrimidin-2-one; 5-methy 1-5-(4-phenoxy-phenyl)-pyrimidine-2,4,6-trione; 1-homoarginine; 5-hydroxy-1-tryptophan; phosphoric acid mono-[2-amino-3-(3h-imidazol-4-yl)-propyl-]ester; 1-homoserine; 1-hexadecylsulfonyl fluoride; homoserinelactone; histamine; histidinol; 4-carboxy-5-(1-pentyl)hexylsulfany 1-1,2,3-triazole; heptyl 1-thiohexopyranoside; (4s)-4-{[(2s)-2-amino-3-oxopropyl]sulfanyl}-1-homoserinate; 2-acetyl-3-[(4-amino-2-methyl-5-pyrimidinyl)methyl]-4-methyl-5-(4, 6,6-trihydroxy-3, 5-dioxa-4,6-diphosphahex-1-yl)thiazolium inner salt p,p'-dioxide; heptane-1,2,3-triol; hydroxy-phenylacetic acid 8-methyl-8-aza-bicyclo[3.2.1]oct-3-yl ester; betahydroxytryptophane; huperzine b; huperaine a; 3-chloro-9-ethyl-6,7,8,9,10,11-hexahydro-7,II-methanocycloocta[b] quinolin-12-amine; willardiine; docosa-4,7,10,13, 16,19-hexaenoic acid; hexanoyl-coenzyme a; 3,6-dihydroxyxanthene-9-propionic acid; phenylacetaldehyde; em-17 45; hyperforin; 2-phenethyl-2,3-dihydro-phthalazine-1,4-dione; l-[2-(3-biphenyl)-4-methylvaleryl)] amino-2-(2-pyridylsulfonyl)amino-2-propanone; 2-[trans-(4-aminocyclohexyl) amino]-6-(benzyl-amino)-9-cyclopentylpurine; d-myoinositol-2,4,5-trisphosphate; 1-benzyl-5-methoxy-2-methyl-1 h-indol-3-yl)-acetic acid; d-myo-inositol-1,4,5-triphosphate; (1 s,3s,4s)-1,3,4-triphospho-myo-inositol; isobutylbenzene; (1 s,3r,4r,6s)-1,3,4,6-tetrapkisphosphate; sc-74020; 4r-fluoro-n6-ethanimidoyl-1-lysine; dpi59; inositol-(1,3,4,5,6)-pentakisphosphate; inhibitor idd 384; 4,6-dideoxy-4-{[4, 5, 6-trihydroxy-3-(hydroxymethyl)cyclohex-2-en-1-yl] amino}-alpha-d-lyxo-hexopyranosyl-(1→4) alpha-d-threo-hexopyranosyl-(1→6)-alpha-1-threohexopyranose; 4-[(isopropylamino)methyl] phenylalanine; 4-iodo-acetamido phenylboronic acid; beta-aspartyl residue; isoaspartyl group; ado-p-ch2-p-ps-ado; 2-amino-3-(3-hydroxy-7, 8-dihydro-6h-cyclohepta[d]-4-isoxazolyl)propionic acid; gamma-glutamyl[s-(2-iodo benzyl)cysteinyl] glycine; l-alpha-glycerophospho-d-myo-inositol-4,5-bis-phosphate; 2-iodobenzylthio group; ic261; isocitrate calcium complex; 4-imino-5-methidy 1-2-methylpyrimidine; isocltnc acid; 5-iododeoxyuridine; idd552; imidazole-derived cellobiose; gluco-phenylimidazole; (5s)-5-iododihydro-2,4(1h,3h)-pyrimidinedione; 7-iodo-1,2,3,4-tetrahydro-isoquinoline; indole naphthyridinone; 1-iduronic acid; o2-sulfo-glucuronic acid; 4,5-dehydro-l-iduronic acid; 1,4-dideoxy-o2-sulfo-glucuronic acid; (2r,3r,4s,5r)-2-acetamido-3,4-dihydroxy-5-hydroxymethyl-piperidinium; (3r, 4r,5r)-5-(hydroxymethyl)piperidine-3,4-diol; 4-imino-5-methidyl-2-trifluoromethylpyrimidine; alpha-amino-2-indanacetic acid; indole-3-glycerol phosphate; n-(r-carboxy-ethyl)-alpha-(s)(2-phenylethyl); 3,5-dichloro-4-[(4-hydroxy-3-isopropylphenoxy) phenylacetic acid; n-isopropyl-n'-hydroxyguanidine; d-myo-inositol-hexasulphate; 4-imidazolmethylene-5-imidazolone chromophore; allo-isoleucine; 4'-deoxy-4'acetylamino-pyridoxal-5'-phosphate; 3-(1-aminoethyl) nonanedioic acid; n-[isoleucinyl]-n'-[adenosyl]diaminosufone; glutamyl group; n5-imino-ethyl-l-ornithine; n-[o-phosphono-pyridoxyl]-isoleucine; [4-({[5-benzyloxy-1-(3-carbamimidoyl-benzyl)-1 h-indole-2-carbonyl]amino} methyl)-phenyl]-trimethyl-ammonium; imidazole; tetra(imidazole)diaquacopper (ii); tetra(imidazole)diaquacopper (i); immucillin-g; 1,4-dideoxy-4-aza-l-(s)-(9-deazahypoxanthin-9-yl)-d-ribitol; 2-iminobiotin; 2-(beta-d-glucopyranosyl)-5-methyl-1,2,3-benzimidazole; 6-ophosphoryl inosine monophosphate; inosmlc acid; 2-hydroxymethyl-pyrrolidine-3,4-diol; phosphoric acid mono-[5-(2-amino-4-oxo-4,5-dihydro-3h-pyrrolo[3,2-d]pyrimidin-7-yl)-3,4-dihydroxy-pyrrolidin-2-ylmethyl]; cis-[4, 5-bis-(4-chlorophenyl)-2-(2-isopropoxy-4-methoxyphenyl)-4,5-dihyd roimidazol-1-yl]-piperazin-1-yl-methanone; cis [4,5-bis-(4-bromophenyl)-2-(2-ethoxy-4-methoxyphenyl)-4,5-dihydroimidazol-1-yl]-[4-(2-hydroxyethyl)piperazin-1-yl]methanone; {1-[(3-hydroxy-methyl-5-phosphonooxymethylpyridin-4-ylmethyl)-amino]-ethyl}-phosphonic acid; 1,5-bis(n-benzyloxycarbonyl-1-leucinyl) carbohydrazide; 1-octadecyl-2-acetamido-2-deoxy-sn-glycerol-3-phosphoethylmethyl sulfide; indole; 3-bromo-7-nitroindazole; d-[(nhydroxyamino)carbonyl]phenylalanine; d-[(amino)carbonyl]phenylalanine; n-(r-carboxy-ethyl)-alpha-(s)-(2-phenylethyl)glycyl-l-arginine-n-phenylamide; 5-nitro-6-ribityl-amino-2,4(1 h,3h)-pyrimidinedione; 5-(6-dribitylamino-2,4-dihydroxypyrimidin-5-yl)-1-penty 1-phosphonic acid; al-6629, [2h-thieno[3,2-e]-1,2-thiazine-6-sulfonamide,2-(3-methoxyphenyl)-3-(4-morpholinyl)-, 1,1dioxide]; al-6619, [2h-thieno[3,2-e]-1,2-thiazine-6-sulfonamide,2-(3-hydroxyphenyl)-3-(4-morpholinyl)-, 1,1dioxide]; indirubin-5-sulphonate; myo-inositol; tl-3-093; n-(3-cyclopropyl(5,6, 7,8,9, 1 O0-hexahydro-2-oxo-2h-cycloocta[b]pyran-3-yl)methyl)phenylbenzensulfonamide; 4-(aminosulfonyl)-n-[(4-fluorophenyl)methyl]-benzamide; 4-(aminosulfonyl)-n-[(2,4-difluorophenyl)methyl]-benzamide; 2-(carboxymethoxy)-5-[(2s)-2-({(2s)-2-[(3-carboxy-propanoyl) amino]-3-phenylpropanoyl}amino)-3-oxo-3-(pentylamino)propyl]benzoic acid; carpropamide; 2-{4-[(2s)-2-[({[(1 s)-1-carboxy-2-phenylethyl]amino}carbonyl) amino]-3-oxo-3-(pentylamino)propyl]phenoxy} malonic acid; 4-(aminosulfonyl)-n-[(2,5-difluorophenyl)methyl]benzamide; 3-iodo-benzyl alcohol; 4-(aminosulfonyl)-n-[(2, 3,4-trifluorophenyl)methyl]-benzamide; 4-(aminosulfonyl) n-[(2,4,6-trifluorophenyl)methyl]-benzamide; 4-(aminosulfonyl)-n-[(3,4,5-trifluorophenyl)methyl]-benzamide; 2-propanol, isopropanol; 4-iodophenol; (diaminomethyl-methyl-amino)-acetic acid; indolylpropionic acid; isopenicillin n; 1-hydroxy-3-methylbutane; l-methyl-2-oxy-5,5-dimethyl pyrrolidine; isopropyl alcohol; 5-methyl-2-(1-methylethyl)phenol; 3-[isopropyl(4-methylbenzoyl)amino]-5-phenylthiophene-2-carboxylic acid; d-myo-inositol-1-phosphate; phenol; indole-3-propanol phosphate; 3-isopropylmalic acid; para-iodo-d-phenylalanine hydroxamic acid; (p-iodophenylacetylamino)methylphosphinic acid; isopentyl pyrophosphate; 1-(isopropylthio)-beta-galactopyranside; s-isopropy 1-isothiourea; 2-methoxy-3-isopropylpyrazine; (5-oxo-5,6-dihydro-indolo [I,2-a]quinazolin-7-yl)-acetic acid; (7as, 12ar,12bs)-1,2,3,4, 7a, 12,12a, 12boctahydroindolo[2,3-a]quinolizin-7 (6h)-one; (1 s)-1 (9-deazahypoxanthin-9yl) 1,4-dideoxy-1,4-imino-d-ribitol-5-phosphate; iso24; pd150606; isobutyric acid; isochorismic acid; p-(2'-iodo-5'-thenoyl)hydrotropic acid; isatin; para-isopropylaniline; phosphorylisopropane; isoquinoline; se-ethylisoselenourea; isoniazid; tubazid; rimitsid; isonicotinylhydrazine; lanizid; nydrazid; inositol 1,3-bisphosphate; iminotryptophan; inositol 1,3,4,5-tetrakisphosphate; ethylisothiourea; iso-ursodeoxycholic acid; 5-iodouracil; isovaleric acid; iodo-willardiine; indirubin-3'-monoxime; n-alpha-acetyl-3,5-diiodotyrosylglycine; 3-iodo-tyrosine; threonine derivative; n-{3-[4-(3-amino-propyl)-piperazin-1-yl]-propyl}-3-(2-thiophen-2-y 1-acetylamino)-5-(3,4,5-trihydroxy-6-hydroxymethyl-tetrahydropyran-2-yloxy)-benzamide; n-{3-[4-(3-amino-propyl)-piperazin-1-yl]-propyl}-3-nitro-5-(galactopyranosyl)-alpha-benzamide; jaspisamide a; je-2147, agl 776, kni-764; 3-[(2, 4-dichlorobenzoyl)(isopropyl) amino]-5-phenylthiophene-2-carboxylic acid; k201; kabiramide c; n-pyridoxyl-7-keto-8-aminopelargonic acid-5'-monophosphate; kanamycin a; 7-keto-8-aminopelargonic acid; 3"-(beta-chloroethyl)-2",4"-dioxo-3,5"-spiro-oxazolidino-4-deacetoxy-vinblastine; hydrolyzed cephalothin; lysine nz-carboxylic acid; 2-keto-3-deoxygluconate; 3-deoxy-d-manno-oct-2-ulosonic acid; 10-cf3c(oh)2-ddacthf, hydrolyzed form of 1 O-trifluoro-acetyl-5, 10-dideazaacyclic-5,6, 7,8-tetrahydrofolic acid; 1 alpha,25-dihydroxyl-20-epi-22-oxa-24,26,27-trihomovitamin d3; ara-alpha(1,3)xyl; 4-nitrophenyl-ara; kifunensine; alpha-ketoisovaleric acid; ketovaline; 2-amino-6-aminomethyl-8-phenylsulfanylmethyl-3h-quinazolin-4-one; kaempherol; 4-(methylsulfanyl)-2-oxo butanoic acid; 5-hydroxy-2-(hydroxymethyl)-4 hpyran-4-one; 17-dmag; (2-[2-ketopropylthio] ethanesulfonate; 2-dehydropantoate; (s)-2-amino-4-[(2s,3r)-2,3,5-trihydroxy-4-oxo-pentyl]mercaptobutyric acid; k-252a; bis-napthyl beta-ketophosphonic acid; 1-2-amino-4-[2-aminophenyl]-4-oxobutanoic acid; I-acetyl-4-(4-{4-[(2-ethoxyphenyl)thio]-3-nitrophenyl} pyridin-2-yl)piperazine; n-[(3z)-5-tert-butyl-2-phenyl-1,2-dihydro-3h-pyrazol-3-ylidene]-n'-(4-chlorophenyl)urea; inhibitor of p38 kinase; 1,2-di-1-(3, 7, 11, 15-tetramethyl-hexadecane)-sn-glycero-3-phosphate; ly249543; 1,2-di-1-(3,7,11,15-tetramethyl-hexadecane)-sn-glycerol; ly374571; 2,3-di-o-phytanly-3-snglycero-l-phosphoryl-3'-sn-glycerol-l'-phosphate; 3-[(5s)-1-acety 1-3-(2-chlorophenyl)-4,5-dihydro-1 h-pyrazol-5-yl] phenol; 1-756,423; lactic acid; 5-fluorolevulinic acid; maltosyl-alpha (1,4)-d-gluconhydroximo-1,5-lactam; allolactose; n,n-dimethyl-1-alanine; 4'-nitrophenyl-3i-thiolaminaritrioside; lanosterol; 1-alfa-lysophosphatidylcholine,lauroyl; 4-(17-hydroxy-5, 12-dimethyl-3-oxo-2, 16-dioxabicyclo[13.3.1]nonadeca-4,8, 1 O-trien-17-yl)-2-thiazolidinone; lactose; dodecanoic acid; perchlorate ion; I-pyridoxyl-n,o-cycloserylamide-5-monophosphate; (5r)-5-amino-6-hydroxyhexylcarbamic acid; lauryl dimethylaminen-oxide; [3-(dodecanoylamino)propyl] (hydroxy)dimethylammonium; 6-hydroxy-1-norleucine; levulinic acid; (4s)-5-fluoro-1-leucine; d-limonene 1,2-epoxide; 6-[1-(3,5,5,8,8-pentamethyl-5,6,7,8-tetrahydronaphthalen-2-yl) cyclopropyl]pyridine-3-carboxylic acid; 1-guluronic acid 6-phosphate; gluconolactone; 1-glucuronic acid; 1,2-dipalmitoyl-phosphatidyl-glycerole; 1-[(n-hydroxyamino)carbonyl] phenylalanine; lipid fragment; 3,4-dihydroxy-1-methylquinolin-2(1h)-one; (3e)-3-[(4-hydroxyphenyl)imino]-lhindol-2(3h)-one; 3-pyridin-4-yl-2,4-dihydro-indeno[1,2-c] pyrazole; sri-9439; sri-9662; 2-tridecanoyloxypentadecanoic acid; 3-oxo-pentadecanoic acid; 3a-oxobutyric acid; I-myo-inositol-1-phosphate; 3-oxiran-2ylalanine; 5-thio-a/b-d-mannopyranosylamine; 4-amino-I-[(1 s,3r,4r, 7s)-7-hydroxy-I-(hydroxymethyl)-2, 5-dioxabicyclo[2.2.1]hept-3-yl]-5-methylpyrimidin-2(1 h)one; n'-pyridoxyl-lysine-5'-monophosphate; nz(dicarboxymethyl)lysine; (3r)-3-methyl-l-glutamic acid; [(2r,3 s,4r, Sr)-5-(6-amino-9h-purin-9-yl)-3,4-dihydroxytetrahydro-2-furanyl]methyl sulfamate; dodecyl-alpha-d-maltoside; 5-nitroso-6-ribityl-amino-2,4(lh,3h)-pyrimidinedione; pentane; 1-leucyl-hydroxylamine; 3-amino-4-{3-[2-(2-propoxy-ethoxy)-ethoxy]-propylamino}-cyclobut-3-ene-1, 2-dione; noradrenaline; [[4-(aminomethyl)phenyl]amino] oxo-acetic acid; 7-(2-amino-2-phenyl-acetylamino)-3-chloro-8-oxo-1-aza-bicyclo [4.2.OJ oct-2-ene-2-carboxylic acid; lambda-bis(2,2'-bipyridine)imidazole osmium (ii); xylose-derivedlactam oxime; Ipc-ether; 2-amino-but-3-ynoic acid; lysophosphotidylserine; lambda-bis(2,2'-bipyridine)-(5-methyl-2-2'-bipyridine)-c9-adamantane ruthenium (ii); lambda-bis(2,2'-bipyridine)imidazole ruthenium (ii); 6-hydroxy-6-methyl-heptan-3-one; 1-tryptophanamide; 1-tryptophan; 7,8-dimethylalloxazine; 6,7-dimethylalloxazine; (3r,5r)-7-((1 r,2r,6s,8r,8as)-2,6-dimethyl-8-{[(2r)-2-methylbutanoyl]oxy}-1,2,6, 7,8,Sa-hexahydronaphthalen-1-yl)-3,5-dihydroxyheptanoic acid; (2s)-2-amino-3-butenoic acid, (2s)-2-amino but-3-enoicacid; 1-xylulose 5-phosphate; 1-xylose (cyclic form); 1-xylitol 5-phosphate; 8,9-dichloro-2, 3,4,5-tetrahydro-lh-benzo[c]azepine; 2-(4-morpholinyl)-8-phenyl-4h-1-benzopyran-4-one; ly341770; ly231514; ly231514 tetra glu; 2-allyl-6-methyl-phenol; 2,6-diaminohexanoic acid amide; butylamine; I-amino-1-carbonyl pentane; 6-amino-1-methylpurine; (3s)-3-amino-I-(cyclopropylamino)heptane-2,2-diol; d-mannose I-phosphate; (2s)-2-amino-4-(methylsulfanyl)-1-pyridin-2-ylbutane-1, 1-diol; I-methoxy-2-(2-methoxyethoxyl)ethane; n-trimethyllysine; alpha-d-mannose-6-phosphate; 6'-methy 1-thiamin diphosphate; 7n-methyl-8-hydroguanosine-5'-diphosphate; d-glycero-d-mannopyranose-7-phosphate; 1,4-dithio-alpha-d-mannose; 4-methylthio-alpha-d-mannose; ol-methyl-4-deoxy-4-thio-alpha-d-glucose; cyclohexyl-hexyl-beta-dmaltoside; mannobiose; mercury acetate ion; maleic acid; 2-deoxy-2-fluoro-alpha-d-mannose; alpha-methyl-n-acetyld-glucosamine; 3-hydroxy-3-methyl-glutaric acid; alpha-ketomalonic acid; maltose; 1-o-methyl-alpha-d-mannose; alpha-d-mannose; 2-amino-8-methylquinazolin-4(3h)-one; aurodox; 1-methylmocimycin; antibiotic x-5108; goldinodox; goldinomycin; d-mannuronic acid; 4-deoxy-d-mannuronic acid; artigenin congener; dibenzylbutyrolactonelignanolide; mafp; 3-methyl-benzene-1,2-diol; 2-deoxy-2-fluoro-beta-d-mannose; methyl-beta-galactose; toluene; mercuribenzoic acid; I-[(2-amino-6,9-dihydro-lh-purin-6-yl)oxy]-3-methyl-2-butanol; 2-hydroxy-5-({1-[(4-methylphenoxy)methyl]-3-oxoprop-1-enyl}amino)-l-tyrosine; tribromomethane; r-2-{[4'-methoxy-(1,1'-biphenyl)-4-yl]sulfonyl}-amino-6-methoxyhex-4-ynoic acid; mesobiliverdin iv alpha; methicillin acylserine; (ls,5z,7z,17alpha,22e)-24-cyclopropyl-9, 10-secochola-5,7,10,22-tetraene-1,3,24-triol; I-alpha,24s-(oh)2-22-ene-26,27-dehydrovitamin d3; methylmalonyl-coenzyme a; 4-(1-amino-1-carboxy-ethyl)benzoic acid; mercaptocarboxylate inhibitor; nz-(1-carboxyethyl)-lysine; pterin cytosine dinucleotide; 1-(3-mercapto-2-methyl-propionyl)-pyrrolidine-2-carboxylic acid; 4-methyl-1,2-benzenediol; n-[2-(l-maleimidyl)ethyl]-7-diethylaminocoumarin-3-carboxamide; malonaldehyde; 5-mercaptoethanol-2-decenoy 1-coenzyme a; 7 n-methyl-8- hydroguanosine-5'-diphosphate; n-methyldehydrobutyrine; methyl-03-(alpha-d-mannose)-alpha-d-mannose; 4-methylidene-5-one; 9-(2-deoxy-beta-d-ribofuranosyl)-6-methylpurine; I-ethoxy-2-(2-methoxyethoxyl)ethane; ethyl-carbamic acid methyl ester; d-methionine; 2s,3r-2-amino-3-methyl-pentanedioic acid; n5-methylglutamine; meropenem; merrem; meronem; 2-(n-morpholino)-ethanesulfonic acid; (r)-mevalonate; mf268; trifluoromethionine; alpha-l-1-methyl-fucose; beta-1-methyl-fucose; (2s,3s,8s,9s)-3-amino-9-methoxy-2, 6, 8-trimethyl-10-phenyldeca-4, 6-dienoic acid; alpha-1-methyl-fucose; 7-methylguanosine; beta-methyl-dgalactoside; ol-methyl-glucose; 7-methyl-guanosine-5'triphosphate; malachite green; 7n-methyl-8-hydroguanosine-5'-triphosphate; n-(2-acetamido)iminodiacetic acid; 3-mercapto-1-(1,3,4, 9-tetrahydro-b-carbolin-2-yl)-propan-1-one; mesoheme; s-oxymethionine; alpha-methylisocitric acid; [cyclohexylethyl]-[[[[4-[2-methyl-1-imidazolyl-butyl]phenyl] acetyl]-seryl]-lysinyl]-amine; monoisopropyl ester phosphonic acid group; monoisopropylphosphorylserine; dicarboxylic acid c3; propanediolic acid; metahnedicarboxylic acid; malonyl-coenzyme a; n-methylleucine; n-methyl-npropargyl-3-(2,4-dichlorophenoxyl)propylamine;

malonate ion; 3-amino-3-oxopropanoic acid; (s)-2-(phosphonoxy)caproyl-1-leucyl-p-nitroanilide; 1-aminocyclopropylphosphonate; amylotriose; malate ion; n-dimethyl-lysine; n-methyllysine; cu-cyclam; cu-bicyclam; n-hydroxy-4-[(4-methoxylphenyl)sulfonyl]-2,2-dimethyl-hexahydro-1, 4-thiazepine-3(s)-carboxamide; ol-methyl-mannose; mmi-175; n-acetylmannosaminitol; n-methylmesoporphyrin; mercaptomethyl phosphonate; l-carboxyethylaminomethyl-4-aminomethylbenzene; 5-mercapto-2-nitro-benzoic acid; methyl isocyanide; dansylamide; mant-adp; 1,8-di-hydroxy-4-nitro-xanthen-9-one; 5,8-di-amino-1,4-dihydroxy-anthra-quinone; heptamolybdate; 6-(1,3-dihydro-7-hydroxy-5-methoxy-4-methyl-1-oxoiso benzofuran-6-yl)-4-methyl-4-hexanoic acid; mometasone furoate; 8-methyl-9-oxoguanine; 4-(2-{[4-{[3-(4-chlorophenyl)propyl] sulfanyl}-6-(I-piperazinyl)-1,3,5-triazin-2-yl]amino}ethyl) phenol; dioxothiomolybdenum(vi) ion; moxalactam derivative; n-methylmesoporphyrin containing copper; 2-methyl-2,4-pentanediol; (lh-indol-3-yl)-(2-mercaptoethoxyimino)-acetic acid; 1-monooleoyl-rac-glycerol; methionine phosphonate; methionine phosphinate; n-methylpyridoxal-5'-phosphate; 3[n-morpholino]propane sulfonic acid; 3-(3, 4-dimethoxyphenyl)propionic acid; methylphosphinic acid; cyanocinnoline; 5-(4-methoxyphenoxy)-2,4-quinazolinediamine; 2-methylpentane-1,2,4-triol; (4r)-2-methylpentane-2,4-diol; meso-erythritol; beta-dadf, msa, multisubstrate adduct inhibitor; 2,2-dichloro-1-methanesulfinyl-3-methy 1-cyclopropanecarboxylic acid [1-(4-bromo-phenyl)-ethyl]-amide; inhibitor msa367; I-methyloxy-4-sulfone-benzene; [methylseleno]acetate; selenomethionine selenoxide; 5'-o-[(l-methionyl)-sulphamoyl] adenosine; 4-[3-methylsulfanylanilino]-6,7-dimethoxyquinazoline; 5'-deoxy-5'-methyl-thioadenosine; [methyltelluro]acetate; [methylthio]acetate; 5'-deoxy-5'-(methylthio)tubercidin; (1 s)-1-(O-deazahypoxanthin-9-yl)-1,4-dideoxy-1,4-imino-5-methylthio-d-ribitol, mt-immucillin-h, mt-immh; d-mannitol; (1 s)-l-(9-deazaadenin-9-yl)-1,4,5-trideoxy-1,4-imino-5-methylthio-d-ribitol; 9-beta-d-ribofuranosy 1-6-methylthiopurine; (molybdopterin-s,s)-dioxothio-molybdenum(v); (5-methyl-6-oxo-l,6-dihydro-pyridin-3-yl)-1,2-dideoxy-ribofuranose-5-monophosphate; (4strans)-4-(methylamino)-5, 6-dihydro-6-methyl-4h-thieno(2, 3-b)thiopyran-2-sulfonamide-7, 7-dioxide; maltotetraose; meta-tyrosine; 9-methyl uric acid; 4-methylumbelliferyl-alpha-d-glucose; methylumbelliferyl sialic acid; 6-(2,5-dimethoxy-benzyl)-5-methyl-pyrido[2,3-d]pyrimidine-2,4-diamine; 2-methoxyethanol; 7-((carboxy (4-hydroxyphenyl) acetyl)amino)-7-methoxy-(3-((I-methyl-1 h-tetrazol-5-yl) thio)methyl)-8-oxo-5-oxa-I-azabicyclo[4.2.0]oct-2-ene-2-carboxylic acid; 2-o-methyl fucose; 6-deoxy-2-o-methylalpha-l-galactopyranose; myristoyl-coa; 2-(3,4,5-trihydroxyphenyl)-3,5, 7-trihydroxy-4h-1-benzopyran-4-one; 3,3',4',5,5', 7-hexahydroxyflavone; myricetin; cannabiscetin; {[5-(6-amino-purin-7-yl)-3,4-dihydroxy-tetrahydro-furan-2-ylmethoxy]-hydroxy-phosphorylmethyl}-phosphonic acid; n2-({[(4-bromophenyl) methyl] oxy}carbonyl)-nl-[(1 s)-1-formylpentyl]-l-leucinamide; glucosaminyl-(alpha-6)-d-myo-inositol; 4-morpholin-4-ylpiperidine-1-carboxylic acid [1-(3-benzenesulfony 1-1-propyl-allylcarbamoy 1)-2-phenylethyl]-amide; pentadecane; metyrapone; 4-carbamoyl-1-beta-d-ribofuranosyl-imidazolium-5-olate-5'-phosphate; 1-deazothiamin diphosphate; ethylbenzene; pentane-1,5-diamine; 3'-deazo-thiamin diphosphate; n-butylbenzene; n-(5-cyclo-propyl-lh-pyrazol-3-yl)benzamide; n-acetylproline; 2-(acetylamino)-2-deoxy-6-o-methyl-alpha-d-allopyranose; n-acetyl-d-allosamine; 3-acetyl pyridine adenine dinucleotide; nicotinamide adenine dinucleotide acetone adduct; m-(n,n,n-trimethylammonio)-2,2,2-trifluoro-I, 1-dihydroxy-ethylbenzene; nicotinamideadenine-dinucleotide; nicotinamide-adenine-dinucleotide (acidic form); 2-iminiopropanoate; beta-(2-naphthyl)-alanine; 5-n-acetyl-alpha-d-neuraminic acid; 2'-monophosphoadenosine 5'-diphosphoribose; nicotinamide adenine dinucleotide 3-pentanone adduct; naringenin; monastrol; n-butyl-benzenesulfonamide; s-4-nitrobutyryl-coa; [(2-ethoxy-1-naphthoyl)amino]methylboronic acid; 1-n-acetylbeta-d-glucosamine; n2-[(benzyloxy)carbonyl]-nl-[(3s)-1-cyanopyrrolidin-3-yl]-l-leucinamide; n-butyl isocyanide; nicotinamide 8-bromo-adenine dinucleotide phosphate; 2-hydroxy-5-({1-[(2-naphthyloxy)methyl]-3-oxoprop-1-enyl}amino)tyrosine; n6-benzyl adenosine-5'-diphosphate; nitrocefin acyl-serine; nicotinamide; n-carbamoyl-alanine; cytidine-5'-monophosphate-5-n-acetylneuraminic acid; n-carbamoyl-1-aspartate; norcamphor; nanm; cobalt hexammine ion; 2-nitro-p-cresol; (s)-(−)-nicotine, 3-[(2s)-1-methyl-2-pyrrolidinyl]pyridine; 3-aminomethy 1-pyridiniumadenine-dinucleotide; nicotinamide adenine dinucleotide cyclohexanone; 2-(acetylamino)-2-deoxy-a-d-glucopyranose; 7,9-dimethylguanine; nadph dihydro-nicotinamide-adenine-dinucleotidephosphate; ethyl dimethyl ammonia propane sulfonate; n-ethyl-5'-carboxamido adenosine; I-ethylpyrrolidine-2,5-dione; neopterin; n-ethylmaleimide; 2-(2-hydroxy-I, 1-dihydroxymethyl-ethylamino)-ethanesulfonic acid; phenylalanine amide; 2,4-dinitrophenyl 2-deoxy-2-fluoro-beta-d-allopyranoside; 2-[(3-trifluoromethyl)phenyl] amino-3-pyridine-carboxylic acid; 3-amino-5-phenylpentane; n-acetyl-d-galactosamine 6-sulfate; 2-(acetylamino)-2-deoxy-4-o-sulfo-alpha-d-galactopyranose; acetylgalactosamine-4-sulfate; 3ar,5r,6s, 7r, 7ar-5-hydroxymethyl-2-methyl-5,6, 7, 7 a-tetrahydro-3ah-pyrano[3,2-d]thiazole-6, 7-diol; nogalaviketone; 3-(4-amino-2-tert-butyl-5-methy 1-phenylsulfanyl)-6-cyclopentyl-4-hydroxy-6-[2-(4-hydroxy-phenyl)-ethyl]-5,6-dihydro-pyran-2-one; n-hydroxy-4-(methyl {[5-(2-pyridinyl)-2-thienyl] sulfonyl}amino)benzamide; n-cyclohexyltaurine; ches; s-(2-oxo)pentadecylcoa; nicotinamide-adenine-dinucleotide-5-hydroxy-4-oxonorvaline; (1 Or)-1O-formyl-5,8,10-trideazafolic acid; 1 O-formyl-5,8, 10-trideazafolic acid; 4-nitro-inden-1-one; dinitrophenylene; meta-nitro-tyrosine; naphthalen-1-yl-acetic acid; 2-(acetylamino)-2-deoxy-4-obeta-d-galactopyranosy 1-alpha-d-glucopyranose; norleucine; n-acetyl-1-glutamate; norleucine phosphonate; n-acetyl-1-glutamine;

n-methylnaloxonium; aha047; n-pyridoxyl-2-methylalanine-5-phosphate; n-naphthalen-1-ylmethyl-2'-[3, 5-dimethoxybenzamido]-2'-deoxy-adenosine; methylamine; n-[amino(imino)methyl]glycine; (r)-n-(1-methyl-hexyl)-formamide; nicotinamide mononucleotide; 2-[2-(2-cyclohexyl-2-guanidino-acetylamino)-acetylamino]-n(3-mercapto-propyl)-propionamide; nitromethyldethia coenzyme a; nor-n-omega-hydroxy-1-arginine; nitrosoethane; 1-deoxynojirimycin; nanaomycin d; methyl nonanoate (ester); pyridoxal-5'-phosphate-n-oxide; inosine; 3-nitrophenylboronic acid; n-succinyl phenylglycine; cysteine-methylene-carbamoyl-1, 10-phenanthroline; 2-aminopimelic acid; n-propyl isocyanide; p-nitrophenol; 7,8-dihydroneopterin; nna; n,n'-bis(4-amino-2-methylquinolin-6-yl)urea; 5-(aminomethyl)-2-methylpyrimidin-4-amine; nitrilotriacetic acid; quinolinic acid; heparin pentasaccharide; naphthalene trisulfonate; nl,nl 4-bis((s-methyl)isothioureido)tetradecane; nojirimycine tetrazole; nu1025; norvaline; dica; (5z)-5-(lhindol-3-ylmethylene)-4h-imidazol-4-one; n-allylaniline; phosphoric acid mono-[3-amino-5-(5-methyl-2,4-dioxo-3,4-dihydro-2h-pyrimidin-1-yl)-tetra hydro-furan-2-ylmethyl] ester; tetrazolyl histidine; 5,6-dihydroxy-nadp; 2-(2f-benzothiazolyl)-5-styryl-3-(4 f-phthalhydrazidyl)tetrazolium chloride; oxaloacetate ion; trans-a-hydroxy-alpha-methyl cinnamate; 2'-o-acetyl adenosine-5-diphosphoribose; 6-(oxalyl-amino)-lh-indole-5-carboxylic acid; oxidized acetyl dithranol; o-acetylserine; 2-(oxalyl-amino)-benzoic acid; octanoic acid (caprylic acid); 3-carboxy-n,n,n-trimethyl-2-(octanoyloxy)propan-1-aminium; cysteinesulfonic acid; n-octane; hydroxyethylcysteine; 4-oxonicotinamide-adenine dinucleotide phosphate; 4-methylpiperazin-1-yl carbonyl group; n-octyl-2-hydroxyethyl sulfoxide; o-trifluoromethylphenyl anthranilic acid; 2-[3-({methyl[l-(2-naphthoyl) piperidin-4-yl] amino}carbonyl)-2-naphthyl]-1-(1-naphthyl)-2-oxoethylphosphonic acid; 4-hydroxytamoxifen; octahydroindole-2-carboxylic acid; atropine; n-(3-phenyl-2-sulfanylpropanoyl)phenylalanylalanine; 9, 1 O-deepithio-9, 1 O-didehydroacanthifolicin; oleic acid; n-acetyl-1-citrulline; olomoucine; 4-bromo-3-(5'-carboxy-4'-chloro-2'-fluorophenyl)-1-methyl-5-trifluoromethyl-pyrazol; mo(vi)(=o)(oh)2 cluster; orotidine-5'-monophosphate; s-dioxymethionine; 5-oxo-1-norleucine; 2-(oxalyl-amino)-4, 7-dihydro-5h-thieno [2,3-c]pyran-3-carboxylic acid; oxyphenbutazone; 9r, 13ropda; calamine phosphoric acid; oxiranpseudoglucose; o 1-pentyl-mannose;-[pyrrol-1-yl-2,5-dione-methoxymethyl]-pyrrole-2,5-dione; orotic acid; o-succinylbenzoate; o-sulfo-1-serine; 6-(hydroxyethyldithio)-8-(aminomethylthio)octanoic acid; n-octanoyl-b-d-fructofuranosyl-a-dglucopyranoside, sucrose monocaprylate; 2-(oxalylamino)-4,5,6, 7-tetrahydro-thieno[2,3-c] pyridine-3-carboxylic acid; carbamic acid; ovalicin; 2-(beta-dglucopyranosyl)-5-methyl-1,3,4-oxadiazole; oxonic acid; oxalic acid; ortho-xylene; oxalate ion; oxamic acid; 2-oxo-3-pentenoic acid; 4-hydroxy-1,2,5-oxadiazole-3-carboxylic acid; 4-oxoretinol; 2-oxalosuccinic acid; tetrahydrooxazine; [1-(3-hydroxy-2-oxo-I-phenethy 1-propylcarbamoyl)2-phenyl-ethyl]-carbamic acid pyridin-4-ylmethyl ester; pdl 73955; deacetoxycephalosporin-c; ethyl dihydrogen diphosphate; propyl trihydrogen diphosphate; pentyl trihydrogen diphosphate; {[2-(lh-1,2,3-benzotriazol-1-yl)-2-(3, 4-difluorophenyl)propane-1,3-diyl]bis [4, 1-phenylene(difluoromethylene)]}bis(phosphonic acid); 3',5'-dinitro-nacetyl-1-thyronine; phosphoric acid mono-[3,4-dihydroxy-5-(5-hydroxy-benzoimidazol-1-yl)tetrahydro-furan-2-ylmethyl] ester; (2s)-pyrrolidin-2-ylmethylamine; heptaethylene glycol, peg330; 3,6,9, 12,15-pentaoxaheptadecane; 1-3 sugar ring of pentamannosyl 6-phosphate; tetraphenylphosphonium; '5'-o-(n-(1-prolyl)-sulfamoyl)adenosine; purine riboside-5'-monophosphate; {4-[(2s,4e)-2-(1,3-benzothiazol-2-yl)-2-(Ih-1,2,3-benzotriazol-1-yl)-5-phenylpent-4-enyl]phenyl}(difluoro)methylphosphonic acid; 5-phospho-arabinonic acid; 4-aminobenzoic acid; cpad; phosphonoacetic acid; 2,4-dihydroxy-3,3-dimethyl-butyrate; 2-phospho-d-glyceric acid; phosphonoacetohydroxamic acid; {[(2,2-dihydroxy-ethyl)-(2,3,4,5-tetrahydroxy-6-phosphonooxy-hexyl)-amino]-methyl}-phosphonic acid; pantoyl adenylate; n-(phosphonacetyl)-1-aspartic acid; palmitoleic acid; 5-phospho-d-arabinohydroxamic acid; n-(phosphonoacetyl)-1-omithine; 3'-phosphate-adenosine-5'diphosphate; 2-oxy-4-hydroxy-5-(2-hydrazinopyridine) phenylalanine; phosphorylated aspartate; n-[(2r)-2,4-dihydroxy-3,3-dimethylbutanoyl]-beta-alanine; (2r,4s)-2-methyl-2,3,3, 4-tetrahydroxytetrahydrofuran; 3-(2-aminoethyl)-4-(aminomethyl)heptanedioic acid; phenylethane boronic acid; phenyl boronic acid; praline betaine; 2-aminomethylpyrrol-3-acetic acid 4-propionic acid; porphobilinogen; 5-(aminomethyl)-4-(carboxymethyl)-1 h-pyrrole-3-propanoic acid; [2-aminomethyl-5-oxo-4-(4-oxo-cyclohexa-2, 5-dienylmethyl)-4, 5-dihydro-imidazol-1-yl]-acetaldehyde; 4-phenylbutylamine; pentabromophenol; di-stearoyl-3-sn-phosphatidylcholine; coproporphyrin i containing co(iii); 1,2-di-npentanoyl-sn-glycero-3-dithiophosphocholine; molybdenum cofactor; moco; cyclic guanosine monophosphate; I-[n[(phenylmethoxy)carbonyl]-l-leucyl-4-[[n/n[(phenylmethoxy)carbonyl]-/nl-leucyl]amino]-3-pyrrolidinone/n; 2-{I-[2-(2-aminothiazol-4-yl)-2-methoxyiminoacetylamino]-2-oxoethyl}-5, 5-dimethyl-thiazolidine-4-carboxylic acid; pantothenoylaminoethenethiol; carboxylic prpp; cprpp; 3,5,3',5'-tetrachloro-biphenyl-4,4'-diol; p-cresol; (z,z)-4-hydroxy-n,n,n-trimethyl-10-oxo-7-[(1-oxo-9-octadecenyl)oxy]-3,5,9-trioxa-4-phosphaheptacos-I 8-enl-aminium-4-oxide; deoxyguanidinoproclavaminic acid; phosphorylated dihydropteroate; pyridoxyl-alanine-5-phosphate; dipicolinic acid; n-(5'-phosphopyridoxyl)-d-alanine; n-(5'-phosphopyridoxyl)-l-alanine; 1,3-propandiol; 2,3-dio-sulfo-alpha-d-glucopyranose; 9-(4-hydroxy-3-(hydroxymethyl) but-1-yl)guanine; 2-(2-{2-[2-(2-{2-[2-(2-ethoxy-ethoxy)-ethoxy]-ethoxy}-ethoxy)-ethoxy]-ethoxy)ethoxy}-ethanol, polyethyleneglycol peg400; l-deoxy-1-thio-heptaethylene glycol; 3,6,9,12,15,18,21-heptaoxatricosane-1,23-diol; 2-phenylethylamine; 3-[aminoethylphosphoryl]-[1,2-dipalmitoyl] sn-glycerol; di-stearoyl-3-sn-phosphatidylethanolamine; n-valeric acid; 2-phenyl-ethanol; phosphoenolpyruvate; 1-phospholactate; 2-(phosphonooxy)butanoic acid; pf-00356231; 3-phenyl-3-({[4-(4-pyridin-4-ylphenyl)thien-2-yl]carbonyl}amino)propanoic acid; 2-[4-(4-hydroxy-3-isopropyl-phenoxy)-3,5-dimethyl-phenyl]-2h-[1,2, 4]triazine-3,5-dione; 2,3,4,5,6-pentafluorobenzyl alcohol; phenylferricrocin-iron; {4-[3-(6, 7-diethoxy-quinazolin-4-ylamino)-phenyl]-thiazol-2-yl}methanol; 2,6-diisopropylphenol; propofol; platelet activating factor; I-(n-imidazolyl)-2-hydroxy-2-(2,3-dichlorophenyl) octane; penicillin g acyl-serine; (5e,13e)-9,15-dihydroxy-I 1-oxoprosta-5, 13-dien-1-oicacid; guanidine-3-propanol; tetraethylene glycol; I-methoxy-2-[2-(2-methoxyethoxy)-ethane; 1-(2-methoxy-ethoxy)-2-{2-[2-(2-methoxyethoxy)-ethoxy}-ethane; 2-phosphoglycolic acid; o-phosphoglycolohydroxamate; phosphoglycolohydroxamic acid; lysophosphatidylglycerol; 1,2-propanediol; s-1,2-propanediol; r-1,2-propanediol; 2-deazo-6-thiophosphate guanosine-5'-monophosphate; pyridoxyl-glutamic acid-5'monophosphate; prostaglandin g2; n-(chlorophenyl)- n'-hydroxyguanidine; (2z)-2-(benzoylamino)-3-[4-(2-bromophenoxyl) phenyl]-2-propenoic acid; p-hydroxybenzoic acid; n-methyl-n-(methylbenzyl)formamide; aspartyl phosphate; phenylmercury; 4,5,6, 7-tetrachloro-3h-isobenzofuran-1-one; iodo-phenylalanine; n-[(aminooxy)carbonyl] aniline; 3-amino-I-chloro-4-phenyl-butanol-2-yl; 1-phenylalaninol; phenylalanylmethane; 1,10-phenanthroline; formic acid benzyl ester; phthalic acid; peridinin; 1,2-diacyl-sn-glycero-3-phosphoinositol; 2-[2-(2-hydroxy-ethoxy)-ethoxy]-ethanol; iodopheny I; piclamilast; 4-pheny 1-lh-imidazole; thiopyrophosphate; carbobenzoxy-pro-lys-phe-y(po2)-ala-pro-ome; diundecyl phosphatidyl choline; n-pyridoxyl-glycine-5-monophosphate; palmitic acid; pregnenolone; leucine phosphonic acid; palmitoyl; [2-amino-6-(2,6-difluoro-benzoyl)imidazo[I,2-a]pyridin-3-yl]-phenyl-methanone; pyromellitic acid; para-mercury-benzenesulfonic acid; 3-(phosphonomethyl)pyridine-2-carboxylic acid; pmp-hydroxyisoxazole, pyridoxamine-5-phosphate-hydroxyisoxazole; pimelic acid; pterin-6-ylmethyl-monophosphate; phosporic acid mono-[3,4-dihydroxy-5-(5-methoxy-benzoimidazol-1-yl)-tetrahydro-furan-2-ylmethyl]ester; pyridoxamine-5'-phosphate; benzylsulfonic acid; 4'-phosphopantetheine; 1,3-bis(4-amidinophenoxy)pentane; 1-benzyl(r)-propylamine; hypophosphite; phosphonoacetaldehyde; phosphocholine; 1-propanol; pyrophosphate 2-; porphyrin fe(iii); I-ter-butyl-3-p-tolyl-lh-pyrazolo[3,4-d]pyrimidin-4-ylamine; l-tert-butyl-3-(4-chloro-phenyl)-lh-pyrazolo[3,4-d]pyrimidin-4-ylamine; pyridoxyl-alanine-5-phosphate; vitamin b6 complexed with alanine; protoporphyrin ix; 5-phosphoribosyl-1-(beta-methylene) pyrophosphate; pyridoxyl-glutamic acid-5'-monophosphate; phosphonoformic acid; 4-(2-amino-ethoxy)-2-[(3-hydroxy-2-methyl-5-phosphonooxymethyl-pyridin-4-ylmethyl)-amino]-but-3-enoic acid; propanoic acid; (diphosphono)aminophosphonic acid; 3h-pyrazolo[4,3-d] pyrimidin-7-ol; 3-phenyl-1,2-propandiol; 2-amino-4-(hydroxymethyl-phosphinyl)butanoic acid; phosphonopyruvate; 3'-phosphate-adenosine-5'-phosphate sulfate; 3-(p-tolyl)propionic acid; 3-phenylpyruvic acid; 2-(pyrido[1,2-e] purin-4-yl)amino-ethanol; 7-deaza-7-cyano-guanine; pyrroloquinoline quinone; rpr131247; s,spropyithiocysteine; 3-phenylpropylamine; 13-acetylphorbol; n-[4-methyl-3-[[4-(3-pyridinyl)-2-pyrimidinyl]amino]phenyl]-3-pyridinecarboxamide; n6-(2,5-dimethoxy-benzyl)n6-methyl-pyrido[2,3-d]pyrimidine-2,4,6-triamine; 7-deaza-7-aminomethyl-guanine; 6-hydroxy-1,6-dihydro purine nucleoside; propidium; alpha-phosphoribosylpyrophosphoric acid; thioproline; phosphoribosyl atp; adenosine-5'-propylphosphate; 2-propyl-aniline; 2-isobutyl-3-methoxypyrazine; pentasulfide-sulfur; 3-(5-amino-7-hydroxy-[1, 2,3]triazolo[4,5-d]pyrimidin-2-yl)-n-[2-(2-(hydroxymethy 1-phenylsulfanyl)-benzyl]-benzamide; o-phosphoethanolamine; pasbn; ndelta-(n'-sulphodiaminophosphinyl)-1-ornithine; thiobutyric acid s-{2-[3-(2-hydroxy-3,3-dimethyl-4-phosphonooxy-butyry-lamino)-propionylamino]-ethyl}; ethylaminobenzylmethylcarbonyl group; pseudouridine-5'-monophosphate; pteroic acid; n-propyl-tartramic acid; 2-prolyl-5-tert-butyl-[1,3,4] Oxadiazole; pentanedial; tungstopterin cofactor; 2-phenyl-l-[4-(2-piperidin-1-yl-ethoxy)-phenyl]-1,2,3,4-tetrahydro-isoquinolin-6-ol; pentanal; pseudotropine; phosphonotyrosine; tungstopterin; s-ethyl-n-phenyl-isothiourea; phosphatidylethanolamine; 9-butyl-8-(2,5-dimethoxy-benzyl)-2-fluoro-9h-purin-6-ylamine; 8-(2-chloro-3,4,5-trimethoxy-benzyl)-2-fluoro-9-pent-4-ylnyl-9h-purin-6-ylamine; 8-(2,5-dimethoxy-benzyl)-2-fluoro-9h-purin-6-ylamine; 9-butyl-8-(3,4, 5-trimethoxybenzyl)-9h-purin-6-amine; 9-buty 1-8-(4-methoxybenzyl)-9h-purin-6-amine; 9-butyl-8-(3-methoxybenzyl)-9h-purin-6-amine; 9-butyl-8-(2,5-dimethoxy-benzyl)-9h-purin-6-ylamine; 9-butyl-8-(2-chloro-3,4,5-trimethoxy-benzyl)-9h-purin-6-ylamine; 8-(2-chloro-3,4,5-trimethoxy-benzyl)-9-pent-4-ylnyl-9h-purin-6-ylamine; u-pi-a-pi; purine riboside; putrescine; 8-benzo[I,3]dioxol-,5-ylmethyl-9-butyl-2-fluoro-9h-purin-6-ylamine; 8-(2,5-dimethoxy-benzyl)-2-fluoro-9-pent-9h-purin-6-ylamine; purvalanol; pyoverdine-chromophore; pyruvoyl group; pyridoxamine; pyridoxine-5'-phosphate; para-xylene; 4-(3-pyridin-2-yl-lh-pyrazol-4-yl)quinoline; 3-(mercaptomethylene)pyridine; vitamin b6 complexed with 2-amino-pentanoic acid; vitamin b6 complexed with 2-amino-hexanoic acid; 3-(1,1 O-phenanthrol-2-yl)-1-alanine; pyrrole-2-carboxylate; tetrahydropyran; pyridin-3-ylmethanol; pyruvamide; 1,2,5,6-tetrahydro-4h-pyrrolo(3,2,1-ij)quinolin-4-one; 2-pyridinethiol; 2-aminoprop-2-enamide; 4-iodopyrazole; pyrazole; praziquantel; {(1 s)-1-benzyl-4-[3-carbamoyl-1-(1-carbamoy 1-2-pheny 1-ethylcarbamoyl)-(s)-propylcarbamoyl]-2-oxo-5-phenyl-pentyl}-carbamic acid tert-butyl ester; quinaldic acid; 8-hydroxy-4-(1-hydroxyethyl)quinoline-2-carboxylic acid; 3,5,7,3',4'-pentahydroxyflavone; n-{(Is)-4-[bis(2-chloroethyl)amino]-1-methylbutyl}-n-(6-chloro-2-methoxy-9-acridinyl)amine; quisqualate; (4'-{[allyl(methyl) amino]methyl}-1,1'-biphenyl-4-yl)(4-bromophenyl) methanone; allyl-{6-[3-(4-bromo-phenyl)-1-methyl-1 h-indazol-6-yl]oxy} hexyl)-n-methylamine; (2e)-n-allyl-4-{[3-(4-bromophenyl)-5-fluoro-1-methyl-lh-indazol-6-yl] oxy}-n-methyl-2-buten-1-amine; 4-{[1-methyl-5-(2-methyl-benzoimidazol-1-ylmethyl)-lh-benzoimidazol-2-ylmethyl]-amino}-benzamidine; allyl-{4-[3-(4-bromophenyl)-benzofuran-6-yloxy]-but-2-enyl}-methyl-amine; methyltrienolone; 17beta-hydroxy-1 7methyl-19norandrosta-4,9,11-trien-3-one; r1881; allyl-{6-[3-(4-bromo-phenyl)-benzofuran-6-yloxy]-hexyl-}-methyl-amin; ribose-1-phosphate; methyl-[4-(4-piperidine-1-ylmethyl-phenyl)cyclohexyl]-carbaminic acid-(4-chlorophenyl)-ester; 4-amino-n-{4-[2-(2,6-dimethyl-phenoxy}-acetylamino]-3-hydroxy-1-isobutyl-5-phenyl-pentyl)-benzamide; 3-aminon-{4-[2-(2,6-dimethyl-phenoxy)-acetylamino]-3-hydroxyl-isobutyl-5-phenyl-pentyl}-benzamide; ribose-5-phosphate; (1-methyl-lh-imidazol-2-yl)-(3-methyl-4-{3-[(pyridin-3-ylmethyl)-amino]-propoxy}-benzofuran-2-yl)methanone; r048-8071; n-(6-{[3-(4-bromophenyl)-1,2-benzisothiazol-6-yl]oxy} hexyl)-n-methylprop-2-en-1-amine; wrr-99; 1-[4-carboxy-2-(3-pentylamino)phenyl]-5, 5'-di(hydroxymethyl)pyrrolidin-2-one; 9-beta-darabinofuranosyl-adenine; argifin; rhamnose; rapamycin immunosuppressant drug; rasagiline; (4r)-7-azabisabolene; r-azabisabolene; riboflavin; vitamin b2; alpha-ribazole-5'phosphate; ricinoleic acid; radicicol; phosphoramidon; 6,7-dioxo-5h-8-ribitylaminolumazine; glycyl-1-a-aminopimelyle-(d-2-aminoethyl)phosphonate, dihydrolipoic acid; (1,10 phenanthroline)-(tri-carbon monoxide) rhenium (i); 4-phospho-d-erythronohydroxamic acid; glycyl-1-alpha-amino-epsilon-pimelyl-d-alanyl-d-alanine; glycyl-1-alpha-amino-epsilon-pimelyl-d-alanine; delta-bis (2,2'-bipyridine)-(5-methyl-2-2'-bipyridine)-c2-adamantane ruthenium (ii); 8-demethyl-8-dimethylamino-flavin-adenine-dinucleotide; rifampicin; 2,5-diaziridin-1-yl-3-(hydroxymethyl)-6-methylcyclohexa-2,5-diene-I,4-dione; 5-(3-amino-4,4-dihyroxybutylsulfanylmethyl)-tetrahydro-furan-2,3,4-triol; tmr; 5-hydroxy-n-propargyl-1 (r)-aminoindan; rhodamine 6g; ribose; rifamycin cgp 4832; argadin; 5-amino-2-aminomethyl-6-[4, 6-diamino-2-(3,4-dihydroxy-5-hydroxymethyl-tetrahydrofuran-2-yloxy)-3-hydroxy-cyclohexyloxy]-tetrahydro-pyran-3,4-diol; ribose(pyranose form); I-hydroxy-2-(3-pyridinyl)ethylidene bis-phosphonic acid; wrr-112; 3-(7-hydroxy-8-ribityllumazine-6-yl) propionic acid; n-methyl-npropargyl-1 (r)-aminoindan; mono-[3,4-dihydroxy-5-(5-methyl-benzoimidazol-1-yl)-tetrahydorfuran-2-ylmethyl] ester; (r)-mandelic acid; 1-rhannose; 1-rhamnitol; I-deoxyribofuranose-5'-phosphate; roflumilast; 7,8-dihydro-7, 7-dimethy 1-6-hydroxypterin; 4-[3-(cyclopentyloxy)-4-methoxyphenyl]-2-pyrrolidinone; c-1027 aromatized chromophore; propionamide; [(2r,3s,4s,5r)-3,4,5-trihydroxytetrahydrofuran-2-yl]methyl dihydrogen phosphate; (c8-r)hydantocidin 5'-phosphate; (c8-s)-hydantocidin 5'-phosphate; (r)-1-para-nitro-phenyl-2-azido-ethanol; 2-ribofuranosyl-3-iodo-2,3-dihydro-I h-pyrazolo [3,4-d]pyrimidin-4-ylamine; rpr128515; reactive red 1 dye; azo-dye hapten; 3-{[(Ir)-1-benzyl-2-sulfanylethyl]amino}-3-oxopropanoic acid; n-propargyl-l(s)-aminoindan; d-2-keto-3-deoxygalactonate; r-styrene oxide; ribavirin triphosphate; 2-(3,4-dihydroxyphenyl)-5, 7-dihydroxy-4-oxo-4 hchromen-3-yl 6-o-(6-deoxy-alpha-l-mannopyranosyl)-betad-glucopyranoside; ribavirin monophosphate; rwj-51084; 1-benzyloxycarbonylamino-2-pheny 1-ethyl){-[I-carbamoyl-2-(lh-indol-3-yl)-ethylcarbamoyl]-5-phenyl-pentyl}-phosphinic acid; (2e,3s)-3-hydroxy-5'-[(4-hydroxypiperidinl-yl)sulfonyl]-3-methyl-1,3-dihydro-2,3'-biindol-2'(1'h)one; soraphen a; l-hexadecanosulfonyl-o-1-serine; s-2-(boronoethyl)-I-cysteine; shikimate-3-phosphate; 1-phenylsulfonamide-3-trifluoromethy 1-5-parabromophenylpyrazole; 1-o-phosphono-d-glucitol, d-glucitol-6-phosphate; a disubstituted succinyl caprolactam hydroxymate mmp3inhibitor; 5'-[n-[(3s)-3-amino-3-carboxypropyl]-nmethylamino]-5'-deoxyadenosine; (s)-2-hydroxy-2-phenylpropionic acid; (s)-alpha-methylmandelic acid; 4-sulfonamide-[1-(4-aminobutane)]benzamide; n-acetyl-serine; selenazole-4-carboxyamide-adenine dinucleotide; 3-[(1 s)-1-(dimethylamino)ethyl]phenol; s-adenosyl-1-homocysteine; s-adenosyl-1-homoselenocysteine; salicylic acid; adenosine-5'-diphosphate monothiophosphate; (4s)-7-azabisabolene; s-azabisabolene; sb220025; 4-(fluorophenyl)-1-cyclopropylmethyl-5-(2-amino-4-pyrimidinyl)imidazole; n-[2-(lh-indol-5-yl)-butyl]-4-sulfamoyl-benzamide; d-naphthyl-1-acetamido boronic acid alanine; 1,3,2-dioxaborolan-2-ol; (s)-4-bromo-3-hydroxy-3-methylbutyl diphosphate; I-naphthyl-1-acetamido boronic acid alanine; trihydroxyantimonite(iii); [3-(1,3,2-dioxaborolan-2-yloxy)propyl]guanidine; (r)-n-(3-indol-1-yl-2-methyl-propyl)-4-sulfamoyl-benzamide; (s)-n(3-indol-1-yl-2-methyl-propyl)-4-sulfamoyl-benzamide; 2-butanol; [4-(1,3,2-dioxaborolan-2-yloxy)methyl]benzamidine; succinyl-coenzyme a; s-methyl thiocysteine group; 1-thiocitrulline; acetic acid salicyloyl-amino-ester; succinamide-coa; pyridoxyl-n,o-cycloserylamide-5-monophosphate; sucrose octasulfate; (south)-methanocarba-thymidine; s-acetylcysteine; n-(sulfanylacetyl) tyrosylprolylmethioninamide; s-{2-[amino(dihydroxy)-lambda-4-sulfanyl]ethyl}d-cysteine; 2-amino-3-(diethoxyphosphoryloxy)-propionic acid; dodecyl sulfate; o-benzylsulfonyl-serine; hydroxyalanine; mdl 101,146; 3-amino-4-oxybenzyl-2-butanone; 2-sulfhydryl-ethanol; phosphonoserine; 2-amino-4-butyl-5-propylselenazole; s-ethylisothiourea; (3s,6s,9r, 1 0r, 11 s, 12s, 13e, 15e, 18s,21 s)-18-{(1 e,3e, 7s,8s)-9-[(2s,3r,4s,5s,6r,9s, 11s)-9-ethyl-4-hydroxy-3,5,11-trimethyl-8-oxo-I-oxa-7-azaspiro[5.5]undec-2-yl]-8-hydroxy-I, 7-dimethylnona-1,3-dienyl}-10, 12-dihydroxy-3-(3-hydroxybenzyl)-6-isopropylll-methyl-9-(3-oxobutyl)-19-oxa-I,4, 7,25-tetraazabicyclo [19.3.1]pentacosa-13, 15-diene-2,5,8,20-tetrone; adenosylomithine; 5, 10, 15,20-tetrakis(4-sulpfonatophenyl)-21h,23hporphine; 3-nitro-4-(2-oxo-pyrrolidin-1-yl)benzenesulfonamide; l-methyl-3-oxo-1,3-dihydro-benzo[c] isothiazole-5-sulfonic acid amide; o3-sulfonylgalactose; 4-deoxy-4-thio-beta-d-glucopyranose; I-hydroxy-1-thioglycerol; monothioglycerol; n,06-disulfo-glucosamine; guanosine-2',3'-cyclophosphorothioate; salicylhydroxamic acid; laevulinic acid; saha; (s)-des-me-ampa; 6-(2-oxo-hexahydrothieno[3,4-d]imidazol-4-yl)-hexanoic acid; (4-hydroxymaltosephenyl) glycine; n-(5-amino-5-carboxypentyl)glutamic acid; heptanoic acid; o-sialic acid (chair conformation); o-sialic acid; 3-trimethylsilylsuccinic acid; 1,2,3,4-tetrahydro-isoquinoline-7-sulfonic acid amide; 5-(1-carboxy-Iphosphonooxy-ethoxyl)-shikimate-3-phosphate; beta-sialic acid; 2-(thiomethylene)-4-methylpentanoic acid; lactose sialic acid; alpha(2,3) sialyllactose; 2-methylbutanoic acid; s-methylcysteine; methyl-2-s-(alpha-d-mannopyranosyl)-2-thio-alpha-d-mannopyranoside; methionine sulfoxide; n-succinyl methionine; (s)-mandelic acid; sulfamic acid 2,3-o-(1-methylethylidene)-4,5-o-sulfonyl-beta-fructopyranose ester; 2,4-dihydroxy-trans cinnamic acid; 5-[bis-2(chloroethyl)-amino]-2, 4-dintro-benzamide; n-{1-[5-(l-carbamoyl-2-mercapto-ethylcarbamoyl)-pentylcarbamoyl]-2-[4-(difluoro-phosphono-methyl)-phenyl]-ethyl}-3-{2-[4-(difluorophosphono-methyl)-phenyl]-acetylamino}-succinamic acid; thionicotinamide-adenine-dinucleotide; selenoinosine; 3-aminosuccinimide; 1-(isopropylamino)-3-(1-naphthyloxy)-2-propanol; 4-(2-oxo-hexahydro-thieno[3, 4-d]imidazol-4-yl)-butyricacid; isatoic anhydride; dioxyselenocysteine; methyl phosphinic acid; adenosine phosphonoacetic acid; d-sorbitol; sp-adenosine-3',5'-cyclic-monophosphorothioate; n-hydroxyln(4-methoxyphenyl) sulfonyl-4-(z,en-methoxyimino)pyrrolidine-2r-carboxamide; n-(2-aminopropyl)-1,4-diaminobutane; pa(34); sinapoyl coenzyme a; 2-deamino-6-deoxy-6thiophosphite-5'-phosphate guano sine; sphingosine; n-hydroxy-1-(4-methoxyphenyl)sulfonyl-4-benzyloxycarbonyl-piperazine-2-carboxamide; spermine (fully protonated form); sparsomycin; sulfopyruvate; (4e,8e,12z,16z)-n,n,4,8,13,17,21-heptamethyldocosa-4,8, 12,16,20-pentaen-1-amine; lipid fragment; sr12813; siroheme; 5'-o-(n-(1-seryl)-sulfamoyl)adenosine; 3-butylthiolane I-oxide; (2s,5s)-5-carboxymethylproline; 1,4-deoxy-1,4-dithio-beta-d-glucopyranose; d-2-keto-3-deoxygluconate; 4-(acetylamino)-3-amino benzoic acid; 4-(acetylamino)-3-guanidinobenzoic acid; 4-(acetylamino)-3-[(hydroxyacetyl)amino]benzoic acid; 4-(acetylamino)-3-[(aminoacetyl)amino]benzoic acid; 4-sulfonamide-[4-(thiomethylaminobutane)] benzamide; stearic acid; 2-amino-4h-1,3-benzoxathiin-4-ol; sti-571; resveratrol; 2-{[fannyl(hydroxy)amino]methyl)-4-methylpentanoic acid; staurosporine; staurosporine; su4984; su9516; 16923; (3r)-4-(p-toluenesulfonyl)-1,4-thiazane-3-carboxylicacid-1-phenyl-alanine ethyl ester; sucrose; 4-diphosphocytidyl-2-c-methyl-d-erythritol 2-phosphate; n-2-succinylarginine; 2-[3,4-dihydroxy-2-hydroxymethyl-5-(2-hydroxy-nonyl) tetrahydro-furan-2-yloxy]-6-hydroxymethyl-tetra hydropyran-3,4,5-triol; n-2-succinylornithine; serine vanadate; swainsonine; 4-hydroxy-3-[(1 s)-3-oxo-I-phenyl-butyl]-2hchromen-2-one; 2s,4r-4-methylglutamate; thymidine-5'monophosphate; [I-(I-benzyl-3-hydroxy-2-oxopropylcarbamoyl)-2-phenyl-ethyl]-carbamic acid benzyl ester; 3-{2,6, 8-trioxo-9-[(2r,3 s,4 r)-2,3,4,5-tetrahydroxypentyl]-1,2,3,6,8, 9-hexahydro-7h-purin-7-yl}propyl dihydrogen phosphate; 2'-o-methyl-3'-methyl-3'-deoxy-arabinofuranosyl-thymine-5'-phosphate; 3-{2,6,8-trioxo-9-[(2s,3r,4r)-2,3,4,5-tetrahydroxypentyl]-1,2,3,6,8,9-hexahydro-7h-purin-7-yl}propyl dihydrogen phosphate; 3,5,3',5'-tetraiodo-l-thyronine; 3,3',5, 5'-tetraiodothyroacetic acid; 3-{2,6,8-trioxo-9-[(2r,3r,4r)-2, 3,4,5-tetrahydroxypentyl]-1,2,3,6,8,9-hexahydro-7h-purin-7-yl}propyl dihydrogen phosphate; pl- (5'-adenosyl)p5-(5'thymidyl)pentaphosphate; 3-{2, 6, 8-trioxo-9-[(2s,3s,4 r)-2,3, 4,5-tetrahydroxypentyl]-1,2,3,6,8,9-hexahydro-7h-purin-7-yl}propyl dihydrogen phosphate; trehalose-6-phosphate; [(1-{2[(4-carbamimidoyl-phenylamino)-methyl]-1-methyl-lhbenzoimidazol-5-yl}-cyclopropyl)-pyridin-2-ylmethyleneaminooxy]-acetic acid ethyl ester; (s)-2-[4-(aminomethyl)-lh-1,2,3-triazol-1-yl]-4-methylpentanoic acid; acetic acid n-[2-chloro-5-[6-ethyl-2,4-diamino-pyrimid-5-yl]-phenyl]-[benzyl-triazen-3-yl]ethyl; 9-(6-deoxyalpha-l-talofuranosyl)-6-methylpurine; tris(hydroxyethyl) aminomethane; tatp; 2,4,6-triaminoquinazoline; d(−)-tartaric acid; trihydroxyarsenite(iii); adenosine-5'-rp-alpha-thiotriphosphate; 2-aminoethanesulfonic acid; (s)-2-{methyl-[2-(naphthalene-2-sulfonylamino)-5-(naphthalene-2-sulfonyloxy)-benzoyl]-amino}-succinicacid; tazobactam; tetrabutylammonium 10n; tazobactam intermediate; pnul 77836; tazobactam trans-enamine intermediate; 7-deazaadenosine; 2,4,6-tribromophenol; hexatantalum dodecabromide; tetrabromo-2-benzotriazole; 2-methyl-2-propanol; thiocellobiose; taurocholic acid; triclosan; thiocamphor; ter-tbuty 1(1 s)-1-cyclohexyl-2-oxoethylcarbamate; 1,3,5-trichloro-benzene; n-tridecanoic acid; (e)-(2r,3r,4s,5r)-3,4,5-trihydroxy-2-methoxy-8,8-dimethyl-non-6-enoic acid ((3s,6r)-6-hydroxy-2-oxo-azepan-3-yl)-amide; thiodigalactoside; thiamin diphosphate; thymine; l-azepanl-yl-2-phenyl-2-(4-thioxo-1,4-dihydro-pyrazolo[3,4-d]pyrimidin-5-yl) ethanone adduct; thymidine-5'-diphospho-betad-xylose; 2-thioethenamine; 2-(3-cyano-4-iso butoxyphenyl)-4-methyl-5-thiazole-carboxylic acid; triethyl phosphate; malatelike intermediate; tetrahydrofuran-2-carboxylic acid; 2-[5-methanesulfonylamino-2-(4-aminophenyl)-6-oxo-1,6-dihydro-I-pyrimidinyl]-n-(3,3,3-trifluoro-I-isopropy 1-2-oxopropyl)acetamide; s-ethy 1-n-[4-(trifluoromethyl)phenyl]isothiourea; triglu-5-formyltetrahydrofolate; 2-(beta-d-glucopyranosyl)-5-methyl-1,3,4-benzothiazole; 5-hydroxymethylene-6-hydrofolic acid; (6s)-5,6, 7,8-tetrahydrofolate; deoxythymidine; 2'-deoxythymidine; reduced threonine; thymidine-3',5'diphosphate; thymidine-5'-(dithio) phosphate; c 16-fattyacyl-substrate-mimic; tetrahydrodeoxyuridine; [2(r,s)-2-sulfanylheptanoyl]-phe-ala; (2-sulfany 1-3-p henylpropanoyl)phe-tyr; rb106; beta(2-thienyl)alanine; 4-hydroxy-3,5-dimethyl-5-(2-methyl-buta-1,3-dienyl)-5h-thiophen-2-one; n-pyridoxyl-threonine-5-monophosphate; thio-maltopentaose; thio-maltohexaose; tetramethylammonium ion; 5,10-methylene-6-hydrofolic acid; tris(hydroxymethyl)aminomethane; thymidine-5'-phosphate; n-(4-methoxybenzyl)n'-(5-nitro-1,3-thiazol-2-yl)urea; n-1,2,3,4-tetrahydronaphth-1-yl-2'-[3,5-dimethoxybenzamido]-2'deoxy-adenosine; tropinone; 2,4,6-trinitrophenol; tnt; 3,5,6, 8-tetramethyl-n-methyl phenanthrolinium; o-(2-acetamido-2-deoxy-alpha-d-galactopyranosyl)-I-serine; tolrestat; n-[tosyl-d-prolinyl]aminoethanethiol; sp-722; sp-876; trans-2-phenylcyclopropylamine; n-(2-thienylmethyl)-2,5-thiophenedisulfonamide; 4-carbamoyl-4-{[6-(difluorophosphono-methyl)-naphthalene-2-carbonyl]-amino}-butyric acid; 2-amino-3-(lh-indol-3-yl)-propan-I-ol; phosphonothreonine; thiamine diphosphate; 5-(2-carboxy-2-aminoethyl)-4-hydroxy-I,2-benzoquinone; 2,4,5-trihydroxyphenylalanine quinone; topa quinone; tosyl-d-proline; thiamin phosphate; 2,2': 6',2"-terpyridine platinum(ii); tipranavir; 5-phenylsulfanyl-2,4-quinazolinediamine; 5-[(4-methylphenyl)sulfanyl]-2,4-quinazolinediamine; 5-[4-tert-butylphenylsulfanyl]-2,4-quinazolinediamine; 5-(4-morpholin-4-ylphenylsulfanyl)-2, 4-quinazolinediamine; 6-(octahydro-lhindol-1-ylmethyl) decahydroquinazoline-2,4-diamine; aconitate ion; tricarballylic acid; lipid fragment; 2'-deoxythymidine-beta- 1-rham nose; 1,2,4-triazole; Ih-benoximidazole-2-carboxylic acid; nz2-tryptophan; 2-hydroxy-tryptophan; 2,4-diamino-5-(3,4,5-trimethoxy-benzyl)pyrimidin-1-ium; 1-{2-[2-(2-methoxyethoxyl)ethoxy] ethoxy}-4-(1,1,3,3-tetramethylbutyl)benzene; 4-{2,6,8-trioxo-9-[(2s,3r,4r)-2,3, 4, 5-tetrahydroxypentyl]-1,2,3, 6, 8, 9-hexahydro-7h-purin-7-yl}butyl dihydrogen phosphate; 4-{2, 6,8-trioxo-9-[(2r,3 s,4r)-2,3,4,5-tetrahydroxypentyl]-1,2,3,6, 8,9-hexahydro-7h-purin-7-yl}butyl dihydrogen phosphate; glutathionylspermidine disulfide; glutathionylspermidine; 5'-o-(n-(1-threonyl)-sulfamoyl)adenosine; (2s,3r)-1-amino-2-methylbutane-2,3-diol; 7-[4-(dimethylamino)phenyl]-nhydroxy-4,6-dimethyl-7-oxo-2,4-heptadienamide; (3r)-4-(p-toluenesulfonyl)-1,4-thiazane-3-carboxylicacid-I-leucine; para-toluene sulfonate; I-allyl-3-butyl-8-(n-acetyl-4-aminobenzyl)-xanthine; tetraphenyl-arsonium; ttnpb; tartronate; (3,4-dihydroxy-phenyl)-triphenyl-arsonium; thymidine-5'triphosphate; tu-514; 1-threonohydroxamate 4-phosphate; tyrosinal; 1-tyrosinamide; thymidine-5'-diphosphate; 3,5-diiodotyrosine; tryptophanyl-5'amp; (3s, 8ar)-3-(4-hydroxybenzyl) hexahydropyrrolo[1,2-a]pyrazine-1,4-dione; 3-amino-6-hydroxy-tyrosine; 2-amino-3-[4-hydroxy-6-oxo-3-(2-pheny 1-cyclopropylimino)-cyclohexa-1,4-dienyl]-propionic acid; tyvelose; 3-(4-hydroxy-3-imino-6-oxo-cyclohexa-1,4-dienyl)-alanine; para acetamido benzoic acid; 3,8-diamino-6-phenyl-5-[6-[1-[2-[(1,2,3,4-tetrahydro-9-acridinyl)amino]ethyl]lh-1,2,3-triazol-4-yl] hexyl]phenanthridinium; 3,8-diamino-6-phenyl-5-[6-[1-[2-[(1,2,3, 4-tetrahydro-9-acridinyl)amino]-ethyl]-Ih-1,2,3-triazol-5-yl]hexyl]-phenanthridinium; (4s)-2-[(1 e)-1-aminoprop-1-enyl]-4,5-dihydro-I,3-thiazole-4-carboxylic acid; 1,2,4-triazole-carboxamidine; 4-methyl-5-hydroxyethylthiazole; 2-(sec-butyl)thiazole; 1,3-thiazole-4-carboxylic acid; 4-methyl-5-hydroxyethylthiazole phosphate; uridine-5'-monophosphate; uridine-5'-diphosphate-2-deoxy-2-fluoro-alphad-galactose; phosphoric acid-2'-[2'-deoxy-uridine]ester-5'guanosine ester; phosphoric acid mono-[2-(2,4-dioxo-3,4-dihydro-2h-pyrimidin-1-yl)-4-hydroxy-5-hydroxymethyltetrahydro-furan-3-yl]; 3'-uridinemonophosphate; 4-[(6-amino-4-pyrimidinyl) amino]benzenesulfonamide; I-(3-ophosphono-beta-I-arabinofuranosyl)pyrimidine-2,4(1 h,3h)dione; 6-carboxymethyluracil; uridine-5'-diphosphate-nacetylmuramoyl-1-alanine-d-glutamate; 1,4-dideoxy-5-dehydro-o2-sulfoglucuronic acid; 7-hydroxystaurosporine; uridine-diphosphate-n-acetylglucosamine; uridine-diphosphate-n-acetylgalactosamine; 3'-1-carboxy-I-phosphonooxy-ethoxy-uridine-diphosphate-n-acetylglucosamine; 6-aminohexy 1-uridine-c 1,5'-diphosphate; uridine-5'-diphosphate; udp-alpha-d-xylopyranose; uridine-5'-diphosphate-4-deoxy-4-fluoro-alpha-d-galactose; uridine-5'-diphosphatemannose; 5-fluoro-2'-deoxyuridine-5'-monophosphate; udpglucuronic acid; 6-[(z)-amino(imino)methyl]-n-[4-(aminomethyl)phenyl]-4-(pyrimidin-2-ylamino)-2-naphthamide; 8-(pyrimidin-2-ylamino)naphthalene-2-carboximidamide; 7-methoxy-8-[1-(methylsulfonyl)-1 h-pyrazol-4-yl]naphthalene-2-carboximidamide; [2,4,6-triisopropyl-phenylsulfonyl-I-[3-amidino-phenylalanine]]-piperazine-n'-beta-alanine; ulapualide a; 2'-deoxyuridine 3'-monophosphate; uridine-5'-diphosphate-n-acetylmuramoyl-1-alanine; I-(2-deoxy-2-fluoro-3-o-phosphono-betal-ribofuranosyl)pyrimidine-2,4(lh,3h)-dione; methylumbelliferyl chitotriose; dump; undecyl-beta-d-maltopyranoside; 5-{[(2-amino-9h-purin-6-yl)oxy]methyl}-2-pyrrolidinone; undecanal; 5-amino 6-nitro uracil; lipid fragment; (6,7-difluoro-quinazolin-4-yl)-(1-methyl-2,2-diphenyl-ethyl)amine; p 1-(adenosine-5'-p5-(uridine-5)pentaphosphate; 6-aza-ump; uridylyl-2'-5'-phospho-adenosine; uridine-5'monophosphate 2-deoxy-2-fluoro-galactopyranosy 1-monophosphate ester; uridine-5'-monophosphate glucopyranosylmonophosphateester; phenyl-uridine-5'-diphosphate; 4-[3-carboxymethy 1-3-(4-phosphonooxy-benzyl)-ureido]-4-[(3-cyclohexyl-propyl)-methyl-carbamoyl] butyric acid; uracil; 7,9-dihydro-lh-purine-2,6,8(3h)-trione; urea; 5-flourouracil; uridine; 5,6-diaminouracil; (2e)-3-(Ih-imidazol-4-yl)acrylic acid; n-phenylthiourea; sulfoquinovose-uridine-c 1,6-diphosphate; uridine 5'-triphosphate; uridine-2',3'-vanadate; acetylphosphate; cyclotetrametavanadate; meta vanadate; trivanadate; vancomycin; 4-epi-vancosaminyl derivative of vancomycin; alpha-d-glucose-l-phosphate-6-vanadate; thiamin, vitamin b 1; 4-amino hexanoic acid; n5-(I-imino-3-butenyl)-I-omithine; virginiamycin ml; (2r)-2,5,7,8-tetramethyl-2-[(4 r,Sr)-4,8, 12-trimethyltridecyl]chroman-6-ol; 4-hydroxy-3-methoxybenzoate; 1-valinol; valpromide; 3-[n [benzyloxycarbonyl]-phenylalaninyl-amino]-5-phenyl-pentane-1-sulfonylmethylbenzene; 3-[n-[benzyloxycarbonyl]phenylalaninyl-amino]-5-phenyl-pentane-1-sulfonic acid 4-nitro-phenyl ester; 3-[[4-methyl-piperazinyl]carbonyl]phenylalaninyl-amino]-5-phenyl-pentane-1-sulfonic acid benzyloxy-amide; wrr-204; vinylsulphonic acid; methylphosphonic acid ester group; n-{3-[(7 ar, 12as, 12bs)-7-oxo-1,3,4,6, 7, 7 a, 12a, 12b-octahydroindolo[2,3-a]quinolizin-12 (2h)-yl] propyl}propane-2-sulfonamide; 4-{2-[4-(2-aminoethyl)piperazin-1-yl]pyridin-4-yl}-n-(3-chloro-4-methylphenyl) pyrimidin-2-amine; way-151693; 5-aminolh-pyrimidine-2, 4-dione; methyl(6s)-1-thio-l-mannohexodialdo-6,2-pyranoside; bromo-wr9921 O; (s)-wiskostatin; n-(6-aminohexyl)-5-chloro-Inaphthalenesulfonamide; (6, 7-dihydro-5h-cyclopenta[d] imidazo[2, 1-b]thiazol-2-yl]-4, 7-dihydro[1,4]thiazepine-3,6-dicarboxylic acid; 5-amino-3-methyl-pyrrolidine-2-carboxylic acid; (1 s,2s)-1-amino-I-(1, 3-thiazol-2-yl) propan-2-ol; xanthine; violaxanthin; (3s)-2, 3,4,5-tetrahydropyridin-3-amine; dextrofloxacine; 3-hydroxy-4-(3,4,5-trihydroxy-tetrahydro-pyran-2-yloxy)-piperidin-2-one; xylose-derived imidazole; 5-monophosphate-9-beta-dribofuranosyl xanthine; analogue of indinavir drug; decaethylene glycol; d-xylulose; 9-beta-d-xylofuranosyl-adenine; 2,5-xylidine; 5(r)-5-fluoro-beta-d-xylopyranosyl-enzyme intermediate; xylarohydroxamate; d-xylitol; xylopyranose; cysteine-s-acetamide; 2,5-dimethylpyrimidin-4-amine; 5-{[ethyl(methyl)amino]methyl}-2-methyl-5, 6-dihydropyrimidin-4-amine; 7,10,13-tri(carboxymethyl)-5, 15-dioxo-4, 7, 10, 13, 16-pentaaza-l, 19-dithianonadecane; 3-fluorotyrosine; (s)-3-(4-(2-carbazol-9-yl-ethoxy)-phenyl)-2-ethoxy-propionic acid; tyrosyladenylate; y-700; 7-hydroxy-2-oxo-chromene-3-carboxylic acid ethyl ester; zebularine; pl-(5'-adenosyl)p5-(5'-(3'azido-3'-deoxythymidyl)) pentaphosphate; z-ala prolinal; 3-[(acetyl-methyl-amino) methyl]-4-amino-n-methyl-n-(1-methyl-lh-indol-2-ylm-ethyl)-benzamide; 6-(4-difluoromethoxy-3-methoxyphenyl)-2h-pyridazin-3-one; zn(ii)-(20-oxo-protoporphyrin ix); [4-(6-chloro-naphthalene-2-sulfonyl)-piperazin-1-yl](3,4,5, 6-tetrahydro-2h-[1,4']bipyridinyl-4-yl)-methanone; [3-(4-bromo-2-fluoro-benzyl)-7-chloro-2,4-dioxo-3,4-dihydro-2h-quinazolin-1-yl]-acetic acid; (3r)-3-{[(benzyloxy) carbonyl] amino}-2-oxo-4-phenylbutane-1-diazonium; zinc trihydroxide; 9alpha-fluorocortisol; protoporphyrin ix containing zn; z-pro-prolinal; benzoyl-arginine-alanine-methyl ketone; arecoline; dazoxiben; enalkiren; eniluracil; fotemustine; hexobarbital; hirulog; methoxyamphetamine; nalorphine; peldesine; phenacetin; phencyclidine; piretanide; sorbinil; terlipressin; thiorphan; vanoxerine; Vitamin C; Vitamin B6 (Pyridoxine); Calcitriol; Vitamin B 12; Vitamin D2 (Ergocalciferol); Calcidiol; Vitamin A; Vitamin D3 (Cholecalciferol); Vitamin BI (Thiamine); Vitamin B2 (Riboflavin); Adenosine monophosphate; Adenine; 1-Alanine; I-Arginine; I-Asparagine; I-Aspartic Acid; Adenosine triphosphate; Cysteine; Biotin; Choline; Citrulline; Creatine; l-Cystine; Icosapent; Folic Acid; l-Glutamine; l-Glutamic Acid; Glycine; Glutathione; l-Histidine; l-Isoleucine; g-Homolinolenic acid; l-Leucine; a-Linolenic acid; lipoic Acid; Xanthophyll; l-Lysine; I-Methionine; N-Acetyl-Dglucosamine; NADH; Nicotinic acid; l-Omithine; l-Phenylalanine; Pyridoxal P; Aspartame; l-Proline; Phosphatidylserine; Pyridoxal; Pyruvic acid; Retinoic acid; S-Adenosylmethionine; l-Serine; Succinic acid; Spermine; Tetrahydrofolic acid; l-Threonine; l-Tryptophan; I-Tyrosine; l-Valine; Vitamin E; and Vitamin K3.

In various embodiments, the first solution further comprises a modulator that modulates the interaction between the soluble target and the insoluble material. In some embodiments, the identity of the modulator is known. For example, the modulator may be a chelator for an inorganic ion. In some embodiments, the modulator is a compound being tested for the ability to modulate binding. For example, the modulator may be a drug compound. In some embodiments, the modulator is not required to comprise an element measurable by XRF.

In various embodiments, the method comprises measuring the binding activity of the soluble target to an insoluble material. In some embodiments, the insoluble material comprises a solid format. In various embodiments, the insoluble material comprises a solid format which is a particle, such as a bead. In some embodiments, the insoluble material comprises a particle having an average diameter of between about 1 µm to about 500 µm, or between about 50 µm to about 500 µm, or between about 100 µm to about 500 µm, or between about 200 µm to about 500 µm, or between about 300 µm to about 500 µm, or between about 400 µm to about 500 µm. For example, the insoluble material may have a particle having an average diameter of about 1 µm, about 5 µm, about 10 µm, about 20 µm, about 30 µm, about 40 µm, about 50 µm, about 60 µm, about 70 µm, about 80 µm, about 90 µm, about 100 µm, about 150 µm, about 200 µm, about 250 µm, about 300 µm, about 350 µm, about 400 µm, about 450 µm, or about 500 µm.

In some embodiments, the insoluble material is a nanoparticle or a microparticle. In some embodiments, the insoluble material is a bead, such as a nanobead or a microbead. Non-limiting examples of particles that can be used in the present invention are DYNABEADs™ (THERMOFISHER), MACS™ beads (MILTENYI BIOTEC), TURBOBEADS™ (TURBOBEADS), and GOLD NANOPARTICLES™ (SIGMAALDRICH).

In some embodiments, the microparticles (e.g. microbeads) are about 0.5 micrometers to about 500 micrometers in diameter (e.g. about 0.5 micrometers, or about 1 micrometer, or about 10 micrometers, or about 50 micrometers or about 100 micrometers or about 150 micrometers or about 200 micrometers or about 250 micrometers or about 300 micrometers or about 350 micrometers or about 400 micrometers or about 450 micrometers or about 500 micrometers).

In some embodiments, the nanoparticles (e.g. nanobeads) are smaller than 1 micrometer in diameter (e.g. about 5 to about 500 nanometers, about 50 to about 500 nanometers, about 100 to about 500 nanometers, about 150 to about 500 nanometers, about 200 to about 500 nanometers, about 250 to about 500 nanometers, about 300 to about 500 nanometers, about 350 to about 500 nanometers, about 400 to about 500 nanometers, about 450 to about 500 nanometers, e.g. about 5 nanometers, or about 10 nanometers, or about 50 nanometers, or about 100 nanometers, or about 150 nanometers, or about 200 nanometers, or about 250 nanometers, or about 300 nanometers, or about 350 nanometers, or about 400 nanometers, or about 450 nanometers, or about 500 nanometers). In some embodiments, the nanoparticles (e.g. nanobeads) have a mean particle diameter of 25-500 nm+/−5 nm, 25-500 nm+/−10 nm, 25-500 nm+/−15 nm, 25-500 nm+/−20 nm, 25-500 nm+/−25 nm, 25-500 nm+/−30 nm, 25-500 nm+/−35 nm, 25-500 nm+/−40 nm, 25-500 nm+/−45 nm, or 25-500 nm+/−50 nm. In some embodiments, the nanoparticles (e.g. nanobeads) have a mean particle diameter of about 20 to about 200 nm.

In some embodiments, the insoluble material is glass or polymer surface. In various embodiments, the insoluble material is a resin. In various embodiments, the resin (or "RESIN" as used herein) is one or more materials described immediately below, e.g. as components of particles. The particles can be made using inorganic materials (e.g., silicates, aluminosilicates and siloxanes), organic materials (e.g., polystyrene) or combinations of these. Some particles include polystyrene (PS) resin with some (e.g., 1-2% divinylbenzene) cross linking, also known as Merrifield resin. Other particles include combinations of polyethylene glycol (PEG) and PS such as PEG grafted on a core of PS, for example, TENTAGEL (Bayer Healthcare, Whippany, N.J.) and HYPOGEL (Rapp Polymere GmbH, Tuebingen, Germany), ARGOGEL (Argonaut Technologies Inc., Redwood City, Calif.), and CHAMPION I and II (Biosearch Technologies Inc., Petaluma, Calif.). Another particle is beaded Poly[acryloyl-bis(aminopropyl)polyethylene glycol] commonly known as PEGA resins. Other illustrative particles include polystyrene cross linked with tetra(ethylene glycol) diacrylate (TTEGDA), cross liked ethoxylated acrylate resin such as CLEAR (Peptides International Inc., Louisville, Ky.), polyethylene glycol based resins such as CHEMMATRIX (PCAS BioMatrix Inc., Quebec, Canada).

In various embodiments, the RESIN is $PEG_n$-polystyrene, where n is 1-10, e.g. 1, 2, 3, 4, 5, 6, 7, 8, 9, and 10 (e.g. a TENTAGEL resin).

In some embodiments, the chelator molecule is a peptide, small molecule, or cationic or anionic polymer that is able to bind to a soluble target, such as an inorganic ion or inorganic compound, an organic ion or organic compound, salts, metal ions, or a biological molecule such as a protein, cofactor, nucleotide, or nucleic acid.

In various embodiments, the chelator molecule is a peptide-based ligand. For instance, the peptide may be associated with, e.g. bound to, an insoluble material, e.g. resin, as described herein.

In various embodiments, the peptide has a general formula of:

$F_1CZ_1Z_2CZ_3Z_4Z_5CF_2$, wherein, $F_1$ and $F_2$ are each independently a phenylalanine derivative at position four, as follows:

where X is any element. In some embodiments, X is a halogen. In some embodiments, X is one or more of F, Cl, Br, I and At. In some embodiments, the phenylalanine derivative is 4-bromophenylalanine (F4Br) or 4-iodophenylalanine (F4I), and $Z_1, Z_2, Z_3, Z_4$, and $Z_5$ are each independently an amino acid, optionally selected from D, 1, P, N, H, Q, R, E, W, S, A, G, F, T, L, V, or modifications thereof.

In some embodiments, the peptide is selected from F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), F4ICDICPNHC (SEQ ID NO: 6), F4ICQRCERWC (SEQ ID NO: 7), F4ICHTCFQTC (SEQ ID NO: 8), YBrCR(T/Q)SC (SEQ ID NO: 9) (e.g. YBrCRTSC (SEQ ID NO: 10), YBrCRQSC (SEQ ID NO: 11)), and YmICR(T/Q)SC (SEQ ID NO: 12) (e.g. YmICRTSC (SEQ ID NO: 13), YmICRQSC (SEQ ID NO: 14)) or variants thereof. As used herein, "F4Br" is 4-bromophenylalanine, "F4I" is 4-iodophenylalanine, "YBr" is 3,5-dibromotyrosine, and "YmI" is mono-iodo tyrosine.

In various embodiments, the peptide has a general formula of $Y_1CRX_1SC$ wherein: $X_1$ is Q or T and $Y_1$ is a tyrosine derivative at the three and five positions of the structure:

Y and Z are a halogen or one or Y and Z is a halogen and one of Y and Z is hydrogen.

In various embodiments, $Y_1$ is 3,5-dibromotyrosine or mono-iodo-tyrosine.

In various embodiments, the peptide comprises one or more of YBrCRTSC (SEQ ID NO: 10), YBrCRQSC (SEQ ID NO: 11), YmICRTSC (SEQ ID NO: 13), and YmICRQSC (SEQ ID NO: 14).

In some embodiments, the insoluble material comprises a peptide and has a structure selected from F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5-RESIN), F4ICDICPNHC-RESIN (SEQ ID NO: 6-RESIN), F4ICQRCERWC-RESIN (SEQ ID NO: 7-RESIN), F4ICHTCFQTC-RESIN (SEQ ID NO: 8-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)), and YmICR(T/Q)SC-RESIN (SEQ ID NO: 12-RESIN) (e.g. YmICRTSC-RESIN (SEQ ID NO: 12-RESIN), YmICRQSC-RESIN (SEQ ID NO: 13-RESIN)) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)), and RESIN-YmICR(T/Q)SC (RESIN-SEQ ID NO: 12) (e.g. RESIN-YmICRTSC (RESIN-SEQ ID NO: 13), RESIN-YmICRQSC (RESIN-SEQ ID NO: 14)). In various embodiments the RESIN is PEG$_n$-polystyrene, where n is 1-10, e.g. 1, 2, 3, 4, 5, 6, 7, 8, 9, and 10 (e.g. a TENTAGEL resin) or variants thereof.

In some embodiments, the invention provides for variants of the sequences listed. In some embodiments, the variants are functionally comparable variants.

For example, the present peptides may comprise alterations that do not substantially affect suitability for the uses described herein. For example, one, or two, or three, or four, or five amino acids may be mutated. In some embodiments, the mutation is a substitution. In some embodiments, the mutation is a deletion. In some embodiments, the mutation is an addition. Illustrative mutations are substitutions or additions, which can be conservative or non-conservative in nature.

Conservative substitutions may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gin; (3) acidic: Asp, Glu; (4) basic: His, Lys, Arg; (5) residues that influence chain orientation: Gly, Pro; and (6) aromatic: Trp, Tyr, Phe. Conservative substitutions may be as exchanges of an amino acid by another amino acid listed within the same group of the six standard amino acid groups shown above. For example, glycine and proline may be substituted for one another based on their ability to disrupt a-helices.

Non-conservative substitutions may be exchanges of an amino acid by another amino acid listed in a different group of the six standard amino acid groups (1) to (6) shown above.

In some embodiments, the peptide comprises at least one non-classical amino acid. Illustrative non-classical amino acids include selenocysteine, pyrrolysine, N-formylmethionine p-alanine, GABA and 6-Aminolevulinic acid, 4-aminobenzoic acid (PABA), D-isomers of the common amino acids, 2,4-diaminobutyric acid, a-amino isobutyric acid, 4-aminobutyric acid, Abu, 2-amino butyric acid, y-Abu, E-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, p-alanine, fluoro-amino acids, designer amino acids such as P methyl amino acids, C a-methyl amino acids, N a-methyl amino acids, and amino acid analogs in general).

Further, in various embodiments, mutations, inclusive of substitutions and additions, may also include non-classical amino acids as described herein.

In some embodiments, the peptide comprises a non-classical amino acid which is a phenylalanine derivative at the four position, as follows:

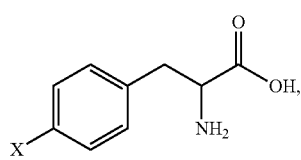

where X is any element. In some embodiments, X is a halogen. In some embodiments, X is one or more of F, Cl, Br, I and At. In some embodiments, the non-classical amino acid is 4-bromophenylalanine and/or 4-iodophenylalanine.

In some embodiments, the peptide is one or more of F41CDICPNHCF4Br (SEQ ID NO: 1), F41CQRCERWCF4Br (SEQ ID NO: 2), F41CFHCFSECF4Br (SEQ ID NO: 3), F41CAGCFTGCF4Br (SEQ ID NO: 4), F41CQLCNVLCF4Br (SEQ ID NO: 5), F41CDICPNHC (SEQ ID NO: 6), F41CQRCERWC (SEQ ID NO: 7), F41CHTCFQTC (SEQ ID NO: 8), or variants thereof and the F4Br may be substituted for 4-iodophenylalanine (F41), 4-chlorophenylalanine (F4CI), or 4-fluorophenylalanine (F4F). In some embodiments, the peptide is one or more of F41CDICPNHCF4Br (SEQ ID NO: 1), F41CQRCERWCF4Br (SEQ ID NO: 2), F41CFHCFSECF4Br (SEQ ID NO: 3), F41CAGCFTGCF4Br (SEQ ID NO: 4), F41CQLCNVLCF4Br (SEQ ID NO: 5), or variants thereof and the F41 may be substituted for 4-fluorophenylalanine (F4F), 4-chlorophenylalanine (F4CI), or 4-bromophenylalanine (F4Br). In some embodiments, the peptide is one or more of F41CDICPNHCF4Br (SEQ ID NO: 1), F41CQRCERWCF4Br (SEQ ID NO: 2), F41CFHCFSECF4Br (SEQ ID NO: 3), F41CAGCFTGCF4Br (SEQ ID NO: 4), F41CQLCNVLCF4Br (SEQ ID NO: 5), or variants thereof and the F4Br may be substituted for 4-iodophenylalanine (F41), 4-chlorophenylalanine (F4CI), or 4-fluorophenylalanine (F4F) and the F41 may be substituted for 4-fluorophenylalanine (F4F), 4-chlorophenylalanine (F4CI), or 4-bromophenylalanine (F4Br).

In some embodiments, the peptide comprises a non-classical amino acid which is a tyrosine derivative at the three and five positions, as follows:

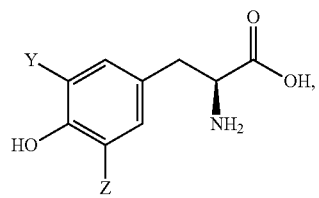

where Y and Z are each independently any element. In some embodiments, Y and/or Z are a halogen. In some embodiments, one of X or Y is a halogen and the other is a hydrogen. In some embodiments, Y and/or Z is one or more of F, Cl, Br, I and At. In some embodiments, one of Y and Z is hydrogen and one of Y and Z is selected from F, Cl, Br, I and At. In a specific embodiment, Y is hydrogen and Z is selected from F, Cl, Br, I and At. In some embodiments, the non-classical amino acid is mono-iodo-tyrosine, a/k/a N-lodo-L-tyrosine ("Yml"). In some embodiments, the non-classical amino acid is 3,5-dibromotyrosine. In specific embodiments, the tyrosine derivative precedes the sequence CRTSC (SEQ ID NO: 15) or CRQSC (SEQ ID NO: 16).

Alternatively, or additionally, the insoluble material, e.g. the chelator molecule (e.g. peptide) includes an element having an atomic number greater 11. In yet another embodiment of the method, the insoluble material, e.g. resin, comprises a chemical element having an atomic number greater than 11. Optionally, the method can also include measuring a sample of the element. Optionally, the method can further include calculating the ratio between a soluble target and an element. In various embodiments, the chemical element having an atomic number greater than 11 is useful as an internal quantitative standard for the measurement methods of the present invention (e.g. the element is present at a known stoichiometry). In various embodiments, the chemical element having an atomic number greater than 11 is useful as a barcoding system for identification of the chelator in a mixture or unordered array.

In various embodiments, the element may be one or more of 12: Magnesium, 13: Aluminum, 14: Silicon, 15: Phosphorus, 16: Sulfur, 17: Chlorine, 18: Argon, 19: Potassium, 20: Calcium, 21: Scandium, 22: Titanium, 23: Vanadium, 25: Manganese, 26: Iron, 27: Cobalt, 28: Nickel, 29: Copper, 30: Zinc, 31: Gallium, 32: Germanium, 33: Arsenic, 35: Bromine, 36: Krypton, 37: Rubidium, 38: Strontium, 39: Yttrium, 40: Zirconium, 41: Niobium, 42: Molybdenum, 43: Technetium, 44: Ruthenium, 45: Rhodium, 46: Palladium, 47: Silver, 48: Cadmium, 49: Indium, 50: Tin, 51: Antimony, 52: Tellurium, 53: Iodine, 54: Xenon, 55: Cesium, 56: Barium, 57: Lanthanum, 58: Cerium, 59: Praseodymium, 60: Neodymium, 61: Promethium, 62: Samarium, 63: Europium, 64: Gadolinium, 65: Terbium, 66: Dysprosium, 67: Holmium, 68: Erbium, 69: Thulium, 70: Ytterbium, 71: Lutetium, 72: Hafnium, 73: Tantalum, 74: Tungsten, 75: Rhenium, 76: Osmium, 77: Iridium, 78: Platinum, 79: Gold, 80: Mercury, 81: Thallium, 82: Lead, 83: Bismuth, 84: Polonium, 85: Astatine, 86: Radon, 87: Francium, 88: Radium, 89: Actinium, 90: Thorium, 91: Protactinium, 92: Uranium, 93: Neptunium, 94: Plutonium, 95: Americium, 96: Curium, 97: Berkelium, 98: Californium, 99: Einsteinium, 100: Fermium, 101: Mendelevium, 102: Nobelium, 103: Lawrencium, 104: Rutherfordium, 105: Dubnium, 106: Seaborgium, 107: Bohrium, 108: Hassium, 109: Meitnerium, 110: Darmstadtium, 111: Roentgenium, 112: Copernicium, 113: Ununtrium, 114: Flerovium, 115: Ununpentium, 116: Livermorium, 117: Ununseptium, and 118: Ununoctium.

In some embodiments, the element is Se, Br, I, Cl, S, or P.

For example, in some embodiments, the present invention is used to determine a ratio of selenium to a second element, or third element, or fourth element or fifth element.

In some embodiments, the insoluble material comprises a peptide and has a structure selected from F41CDICPNHCF4Br-RESIN (SEQ ID NO: 1-RESIN), F41CQRCERWCF4Br-RESIN (SEQ ID NO: 2-RESIN), F41CFHCFSECF4Br-RESIN (SEQ ID NO: 3-RESIN), F41CAGCFTGCF4Br-RESIN (SEQ ID NO: 4-RESIN), F41CQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)), F41CDICPNHC-RESIN (SEQ ID NO: 6-RESIN), F41CQRCERWC-RESIN (SEQ ID NO: 7-RESIN), F41CHTCFQTC-RESIN (SEQ ID NO: 8-RESIN), and YmlCR(T/Q)SC-RESIN (SEQ ID NO: 12-RESIN) (e.g. YmlCRTSC (SEQ ID NO: 13)-RESIN, YmlCRQSC (SEQ ID NO: 14)-RESIN) or RESIN-F41CDICPNHCF4Br (RESIN-SEQ ID NO: 1), RESIN-F41CQRCERWCF4Br (RESIN-SEQ ID NO: 2), RESIN-F41CFHCFSECF4Br (RESIN-SEQ ID NO: 3), RESIN-F41CAGCFTGCF4Br (RESIN-SEQ ID NO: 4), RESIN-F41CQLCNVLCF4Br (RESIN-SEQ ID NO: 5), RESIN-F41CDICPNHC (RESIN-SEQ ID NO: 6), RESIN-F41CQRCERWC (RESIN-SEQ ID NO: 7), RESIN-F41CHTCFQTC (RESIN-SEQ ID NO: 8), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)), and RESIN-YmlCR(T/Q)SC (RESIN-SEQ ID NO: 12) (e.g. RESIN-YmlCRTSC (RESIN-SEQ ID NO: 13), RESIN-YmlCRQSC (RESIN-SEQ ID NO: 14)).

In some embodiments, the insoluble material comprises a peptide and has a structure selected from F41CDICPNHCF4Br-PEG4-Polystyrene (SEQ ID NO: 1-PEG4-Polystyrene), F41CQRCERWCF4Br-PEG4-Polystyrene (SEQ ID NO: 2-PEG4-Polystyrene), F41CFHCFSECF4Br-PEG4-Polystyrene (SEQ ID NO: 3-PEG4-Polystyrene), F41CAGCFTGCF4Br-PEG4-Polystyrene (SEQ ID NO: 4-PEG4-Polystyrene), F41CQLCNVLCF4Br-PEG4-Polystyrene (SEQ ID NO: 5-PEG4-Polystyrene), YBrCR(T/Q)SC-PEG4-Polystyrene (SEQ ID NO: 9-PEG4-Polystyrene) (e.g. YBrCRTSC-PEG4-Polystyrene (SEQ ID NO: 10-PEG4-Polystyrene), YBrCRQSC-PEG4-Polystyrene (SEQ ID NO: 11-PEG4-Polystyrene)) and YmlCR(T/Q)SC-PEG4-Polystyrene (SEQ ID NO: 12-PEG4-Polystyrene) (e.g. YmlCRTSC-PEG4-Polystyrene (SEQ ID NO: 13-PEG4-Polystyrene), YmlCRQSC-PEG4-Polystyrene (SEQ ID NO: 14-PEG4-Polystyrene) or Polystyrene-PEG4-F41CDICPNHCF4Br (Polystyrene-PEG4-SEQ ID NO: 1), Polystyrene-PEG4-F41CQRCERWCF4Br (Polystyrene-PEG4-SEQ ID NO: 2), Polystyrene-PEG4-F41CFHCFSECF4Br (Polystyrene-PEG4-SEQ ID NO: 3), Polystyrene-PEG4-F41CAGCFTGCF4Br (Polystyrene-PEG4-SEQ ID NO: 4), Polystyrene-PEG4-F41CQLCNVLCF4Br (Polystyrene-PEG4-SEQ ID NO: 5), Polystyrene-PEG4-YBrC R(T/Q)SC (Polystyrene-PEG4-SEQ ID NO: 9) (e.g. Polystyrene-PEG4-YBrC RTSC (Polystyrene-PEG4-SEQ ID NO: 10), Polystyrene-PEG4-YBrCRQSC (Polystyrene-PEG4-SEQ ID NO: 11)) and Polystyrene-PEG4-YmlCR(T/Q)SC (Polystyrene-PEG4-SEQ ID NO: 12) (e.g. Polystyrene-PEG4-YmlCRTSC (Polystyrene-PEG4-SEQ ID NO: 13), Polystyrene-PEG4-YmlCRQSC (Polystyrene-PEG4-SEQ ID NO: 14)).

In a specific embodiment, the invention provides a composition comprising an insoluble material, which is comprises a peptide. In a specific embodiment, the invention provides a composition comprising an insoluble material, which comprises a peptide, the peptide comprising one or more of F41CDICPNHCF4Br (SEQ ID NO: 1), F41CQRCERWCF4Br (SEQ ID NO: 2), F41CFHCFSECF4Br (SEQ ID NO: 3), F41CAGCFTGCF4Br (SEQ ID NO: 4), F41CQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)) and YmlCR(T/Q)SC (SEQ ID NO: 12) (e.g. YmlCRTSC (SEQ ID NO: 13), YmlCRQSC (SEQ ID NO: 14)), or variants thereof. In some embodiments, the composition comprises two or more of F41CDICPNHCF4Br (SEQ ID NO: 1), F41CQRCERWCF4Br (SEQ ID NO: 2), F41CFHCFSECF4Br (SEQ ID NO: 3), F41CAGCFTGCF4Br (SEQ ID NO: 4), F41CQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmlCR(T/Q)SC (SEQ ID NO: 12) (e.g. YmlCRTSC (SEQ ID NO: 13), YmlCRQSC (SEQ ID NO: 14)), or variants thereof. In some embodiments, the composition comprises three or more of F41CDICPNHCF4Br (SEQ ID NO: 1), F41CQRCERWCF4Br (SEQ ID NO: 2), F41CFHCFSECF4Br (SEQ ID NO: 3), F41CAGCFTGCF4Br (SEQ ID NO: 4), F41CQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmlCR(T/Q)SC (SEQ ID NO: 12) (e.g. YmlCRTSC (SEQ ID NO: 13), YmlCRQSC (SEQ ID NO: 14)) or variants thereof. In some embodiments, the composition comprises four of F41CDICPNHCF4Br (SEQ ID NO: 1), F41CQRCERWCF4Br (SEQ ID NO: 2), F41CFHCFSECF4Br (SEQ ID NO: 3), F41CAGCFTGCF4Br (SEQ ID NO: 4), F41CQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmlCR(T/Q)SC (SEQ ID NO: 12) (e.g. YmlCRTSC (SEQ ID NO: 13), YmlCRQSC (SEQ ID NO: 14)) or variants thereof. In some embodiments, the composition comprises five of F41CDICPNHCF4Br (SEQ ID NO: 1), F41CQRCERWCF4Br (SEQ ID NO: 2), F41CFHCFSECF4Br (SEQ ID NO: 3), F41CAGCFTGCF4Br (SEQ ID NO: 4), F41CQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmlCR(T/Q)SC (SEQ ID NO: 12) (e.g. YmlCRTSC (SEQ ID NO: 13), YmlCRQSC (SEQ ID NO: 14)) or variants thereof. In some embodiments, the composition comprises six of F41CDICPNHCF4Br (SEQ ID NO: 1), F41CQRCERWCF4Br (SEQ ID NO: 2), F41CFHCFSECF4Br (SEQ ID NO: 3), F41CAGCFTGCF4Br (SEQ ID NO: 4), F41CQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmlCR(T/Q)SC (SEQ ID NO: 12) (e.g. YmlCRTSC (SEQ ID NO: 13), YmlCRQSC (SEQ ID NO: 14)) or variants thereof. Such peptides may bind an analyte at differing affinities as described elsewhere herein.

The present invention provides for use of an insoluble material that may comprise one or more of F41CDICPNHCF4Br-RESIN (SEQ ID NO: 1-RESIN), F41CQRCERWCF4Br-RESIN (SEQ ID NO: 2-RESIN), F41CFHCFSECF4Br-RESIN (SEQ ID NO: 3-RESIN), F41CAGCFTGCF4Br-RESIN (SEQ ID NO: 4-RESIN), F41CQLCNVLCF4Br-RESIN (SEQ ID NO: 5), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmlCR(T/Q)SC-RESIN (SEQ ID NO: 12-RESIN) (e.g. YmlCRTSC-RESIN (SEQ ID NO: 13-RESIN), YmlCRQSC-RESIN (SEQ ID NO: 14-RESIN)) or RESIN-F41CDICPNHCF4Br (RESIN-SEQ ID NO: 1), RESIN-F41CQRCERWCF4Br (RESIN-SEQ ID NO: 2), RESIN-F41CFHCFSECF4Br (RESIN-SEQ ID NO: 3), RESIN-F41CAGCFTGCF4Br (RESIN-SEQ ID NO: 4), RESIN-F41CQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmlCR(T/Q)SC (RESIN-SEQ ID NO: 12) (e.g. RESIN-YmlCRTSC (RESIN-SEQ ID NO: 13), RESIN-YmlCRQSC (RESIN-SEQ ID NO: 14)). The present invention provides for use of an insoluble material that may comprise one of F41CDICPNHCF4Br-RESIN (SEQ ID NO: 1-RESIN), F41CQRCERWCF4Br-RESIN (SEQ ID NO: 2-RESIN), F41CFHCFSECF4Br-RESIN (SEQ ID NO: 3-RESIN), F41CAGCFTGCF4Br-RESIN (SEQ ID NO: 4-RESIN), F41CQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmlCR(T/Q)SC-RESIN (SEQ ID NO: 12-RESIN) (e.g. YmlCRTSC-RESIN (SEQ ID NO: 13-RESIN), YmlCRQSC-RESIN (SEQ ID NO: 14-RESIN)) or RESIN-F41CDICPNHCF4Br (RESIN-SEQ ID NO: 1), RESIN-F41CQRCERWCF4Br (RESIN-SEQ ID NO: 2), RESIN-F41CFHCFSECF4Br (RESIN-SEQ ID NO: 3), RESIN-F41CAGCFTGCF4Br (RESIN-SEQ ID NO: 4), RESIN-F41CQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmlCR(T/Q)SC (RESIN-SEQ ID NO: 12) (e.g. RESIN-YmlCRTSC (RESIN-SEQ ID NO: 13), RESIN-YmlCRQSC (RESIN-SEQ ID NO: 14)). The present invention provides for use of an insoluble material that may comprise two of F41CDICPNHCF4Br-RESIN (SEQ ID NO: 1-RESIN), F41CQRCERWCF4Br-RESIN (SEQ ID NO: 2-RESIN), F41CFHCFSECF4Br-RESIN (SEQ ID NO: 3-RESIN), F41CAGCFTGCF4Br-RESIN (SEQ ID NO: 4-RESIN), F41CQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmlCR(T/Q)SC-RESIN (SEQ ID NO: 12-RESIN) (e.g. YmlCRTSC-RESIN (SEQ ID NO: 13-RESIN), YmlCRQSC-RESIN (SEQ ID NO: 14-RESIN)) or RESIN-F41CDICPNHCF4Br (RESIN-SEQ ID NO: 1), RESIN-F41CQRCERWCF4Br (RESIN-SEQ ID NO: 2), RESIN-F41CFHCFSECF4Br (RESIN-SEQ ID NO: 3), RESIN-F41CAGCFTGCF4Br (RESIN-SEQ ID NO: 4), RESIN-F41CQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmlCR(T/Q)SC (RESIN-SEQ ID NO: 12) (e.g. RESIN-YmlCRTSC (RESIN-SEQ ID NO: 13), RESIN-YmlCRQSC (RESIN-SEQ ID NO: 14)). The present invention provides for use of an insoluble material that may comprise three of F41CDICPNHCF4Br-RESIN (SEQ ID NO: 1-RESIN), F41CQRCERWCF4Br-RESIN (SEQ ID NO: 2-RESIN), F41CFHCFSECF4Br-RESIN (SEQ ID NO: 3-RESIN), F41CAGCFTGCF4Br-RESIN (SEQ ID NO: 4-RESIN), F41CQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmlCR(T/Q)SC-RESIN (SEQ ID NO: 12-RESIN) (e.g. YmlCRTSC-RESIN (SEQ ID NO: 13-RESIN), YmlCRQSC-RESIN (SEQ ID NO: 14-RESIN)) or RESIN-F41CDICPNHCF4Br (RESIN-SEQ ID NO: 1), RESIN-F41CQRCERWCF4Br (RESIN-SEQ ID NO: 2), RESIN-F41CFHCFSECF4Br (RESIN-SEQ ID NO: 3), RESIN-F41CAGCFTGCF4Br (RESIN-SEQ ID NO: 4), RESIN-F41CQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmlCR(T/Q)SC (RESIN-SEQ ID NO: 12) (e.g. RESIN-YmlCRTSC (RESIN-SEQ ID NO: 13), RESIN-YmlCRQSC (RESIN-SEQ ID NO: 14)). The present invention provides for use of an insoluble material that may comprise four of F41CDICPNHCF4Br-RESIN (SEQ ID NO: 1-RESIN), F41CQRCERWCF4Br-RESIN (SEQ ID NO: 2-RESIN), F41CFHCFSECF4Br-RESIN (SEQ ID NO: 3-RESIN), F41CAGCFTGCF4Br-RESIN (SEQ ID NO: 4-RESIN), F41CQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC- RESIN (SEQ ID NO: 11-RESIN)) and YmlCR(T/Q)SC-RESIN (SEQ ID NO: 12-RESIN) (e.g. YmlCRTSC-RESIN (SEQ ID NO: 13-RESIN), YmlCRQSC-RESIN (SEQ ID NO: 14-RESIN)) or RESIN-F41CDICPNHCF4Br (RESIN-SEQ ID NO: 1), RESIN-F41CQRCERWCF4Br (RESIN-SEQ ID NO: 2), RESIN-F41CFHCFSECF4Br (RESIN-SEQ ID NO: 3), RESIN-F41CAGCFTGCF4Br (RESIN-SEQ ID NO: 4), RESIN-F41CQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmlCR(T/Q)SC (RESIN-SEQ ID NO: 12) (e.g. RESIN-YmlCRTSC (RESIN-SEQ ID NO: 13), RESIN-YmlCRQSC (RESIN-SEQ ID NO: 14)). The present invention provides for use of an insoluble material that may comprise five of F41CDICPNHCF4Br-RESIN (SEQ ID NO: 1-RESIN), F41CQRCERWCF4Br-RESIN (SEQ ID NO: 2-RESIN), F41CFHCFSECF4Br-RESIN (SEQ ID NO: 3-RESIN), F41CAGCFTGCF4Br-RESIN (SEQ ID NO: 4-RESIN), F41CQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmlCR(T/Q)SC-RESIN (SEQ ID NO: 12-RESIN) (e.g. YmlCRTSC-RESIN (SEQ ID NO: 13-RESIN), YmlCRQSC-RESIN (SEQ ID NO: 14-RESIN)) or RESIN-F41CDICPNHCF4Br (RESIN-SEQ ID NO: 1), RESIN-F41CQRCERWCF4Br (RESIN-SEQ ID NO: 2), RESIN-F41CFHCFSECF4Br (RESIN-SEQ ID NO: 3), RESIN-F41CAGCFTGCF4Br (RESIN-SEQ ID NO: 4), RESIN-F41CQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmlCR(T/Q)SC (RESIN-SEQ ID NO: 12) (e.g. RESIN-YmlCRTSC (RESIN-SEQ ID NO: 13), RESIN-YmlCRQSC (RESIN-SEQ ID NO: 14)). The present invention provides for use of an insoluble material that may comprise six of F41CDICPNHCF4Br-RESIN (SEQ ID NO: 1-RESIN), F41CQRCERWCF4Br-RESIN (SEQ ID NO: 2-RESIN), F41CFHCFSECF4Br-RESIN (SEQ ID NO: 3-RESIN), F41CAGCFTGCF4Br-RESIN (SEQ ID NO: 4-RESIN), F41CQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmlCR(T/Q)SC-RESIN (SEQ ID NO: 12-RESIN) (e.g. YmlCRTSC-RESIN (SEQ ID NO: 13-RESIN), YmlCRQSC-RESIN (SEQ ID NO: 14-RESIN)) or RESIN-F41CDICPNHCF4Br (RESIN-SEQ ID NO: 1), RESIN-F41CQRCERWCF4Br (RESIN-SEQ ID NO: 2), RESIN-F41CFHCFSECF4Br (RESIN-SEQ ID NO: 3), RESIN-F41CAGCFTGCF4Br (RESIN-SEQ ID NO: 4), RESIN-F41CQLCNVLCF4Br (RESIN-SEQ ID NO: 5), RESIN-YBrCR(T/Q)SC (RESIN-SEQ ID NO: 9) (e.g. RESIN-YBrCRTSC (SEQ ID NO: 10-RESIN), RESIN-YBrCRQSC (RESIN-SEQ ID NO: 11)) and RESIN-YmlCR(T/Q)SC (RESIN-SEQ ID NO: 12) (e.g. RESIN-YmlCRTSC (RESIN-SEQ ID NO: 13), RESIN-YmlCRQSC (RESIN-SEQ ID NO: 14)).

In some embodiments, the insoluble material is composed of oxides, such as ferrites, maghemite, magnetite, or iron oxide, optionally modified by surfactants, silica, silicones or phosphoric acid derivatives.

In some embodiments, the nanoparticle (e.g. nanobead) is a quantum dot. Examples of quantum dots, e.g. produced by colloidal methods, include, but are not limited to, cadmium-selenide (CdSe), cadmium-sulfide (CdS), indium-arsenide (InAs), and indium-phosphide (InP) cadmium-tellurium-sulfide (CdTeS). The number of atoms that comprise a quantum dot can range from 100 to 100,000, typically with a diameter ranging from 2 to 20 nm (e.g., 2, 3, 4, 5, 6, 7, 8, 9, 10, 11, 12, 13, 14, 15, 16, 17, 18, 19, 20, 2.5, 3.5, 4.5, 5.5, 6.5, 7.5, 8.5, 9.5, 10.5, 11.5, 12.5, 13.5, 14.5, 15.5, 16.5, 17.5, 18.5, 19.5, 20.5 nm).

In an illustrative embodiment, the insoluble material comprises a polystyrene bead, as described, for example, in U.S. Pat. No. 9,157,875, the entire disclosure is hereby incorporated by reference.

In some embodiments, the insoluble material comprises a chemical functionality. Illustrative chemical functionalities include, but are not limited to, a chelator, a biological molecule such as a peptide, modified peptide, peptoid, protein, nucleic acid, oligonucleotide, liposome, micelle, or proteoliposome. In some embodiments, the insoluble material comprises a biological cell such as a plant cell, a bacterial cell, a yeast cell, an insect cell, a mammalian cell such as a human cell, a primary cell, a cultured cell, or an immortal cell line. In an illustrative embodiment, the insoluble material comprises a non-adherent cell. In another illustrative embodiment, the insoluble material comprises a receptor. In another illustrative embodiment, the insoluble material comprises a chelator such as a peptide chelator. Illustrative chemical functionalities that may be used in the present invention are provided in US Patent Publication No. 2015/0309021, the entire disclosure is hereby incorporated by reference.

In various embodiments, the chemical functionalities are attached to a particle such as a polystyrene bead. The attachment of a chemical functionality to beads is described in, for example, U.S. Patent Application No. 20030027129, the entire disclosure of which is hereby incorporated by reference.

In some embodiments, the insoluble material comprises at least one chemical element having an atomic number of about 9 or higher. In some embodiments, the chemical element is a heavy element having an atomic number of about 9, about 10, about 11, about 12, about 13, about 14, about 15, about 16, about 17, about 18, about 19, or higher. In illustrative embodiments, the chemical element is sulfur, phosphorus, silicon, potassium, calcium, manganese, iron, cobalt, nickel, copper, zinc, arsenic, rhodium, molybdenum, chromium, selenium, bromine, silver, cadmium, platinum, gold, mercury, lead, gadolinium, dysprosium, terbium, europium, strontium, cesium, barium, or iodine. In some embodiment, the insoluble material comprises a chemical element that is not contained in the first solution, the soluble target, or the modulator.

In various embodiments, the amount of insoluble material used has a volume of between about 0.1 μL and about 2 μL. For example, the amount of the insoluble material used may have a volume of about 0.1 μL, about 0.2 μL, about 0.3 μL, about 0.4 μL, about 0.5 μL, about 0.6 μL, about 0.7 μL, about 0.8 μL, about 0.9 μL, about 1.0 μL, about 1.1 μL, about 1.2 μL, about 1.3 μL, about 1.4 μL, about 1.5 μL, about 1.6 μL, about 1.7 μL, about 1.8 μL, about 1.9 μL, or about 2.0 μL.

In some embodiments, the insoluble material is known to bind the soluble target. In other embodiments, the ability of the insoluble material to bind the soluble target is unknown and can be assessed using methods of the invention.

In various embodiments, the soluble target is present within a first solution that serves to buffer the pH of the soluble target, buffer the redox state of the soluble target, preserve the soluble target, fix the soluble target, sterilize the soluble target, or otherwise render the soluble safe or prepared for reading. In various embodiments, the first solution is free of at least one chemical element having an atomic number of greater than four, where that chemical element is present in the sample. In various embodiments, the first solution is free of at least one chemical element having an atomic number of greater than eight, where that chemical element is present in the sample. In some embodiments, the first solution is free of at least one of the following chemicals or functional groups: dimethylsulfoxide, thiols, sulfate anion, sulfonate anions, chloride anion, bromide anion, fluoride anion, iodide anion, perchlorate anion, phosphate anion, and phosphonate anions. In some embodiments, the first solution comprises one or more of the following chemical or functional groups: amine, imine, nitrate anion, nitrite anion, ammonium cation, acetate anion, carboxylate anion, conjugate bases of carboxylic acids, carbonate anion, formalin, formaldehyde, ethanol, 2-propanol, and iminium cation. In some embodiments, these chemicals offer the correct chemical properties with minimal XRF interference. In some embodiments, the first solution is substantially free of phosphorus and/or sulfur.

In various embodiments, the methods of the invention comprise a step of exposing the insoluble material to the first solution comprising the soluble target so as to test the binding of the soluble target to the insoluble material. In various embodiments, methods of the invention are amenable to multiplexing. In various embodiments, a sample comprising the soluble target and the insoluble material is deposited onto a sample holder or into a sample holder for analysis, such as multiplex analysis.

Illustrative sample holders include, but are not limited to, slides, films, or well plates. In various embodiments, the methods of the invention involve multiplexing analysis that are carried out in a multi-well plate such as a 96-, 384-, or 1536-well plate. Illustrative well plates that may be used in the present invention include those described in U.S. Pat. Nos. 8,238,515, 8,873,707, and 9,476,846, the entire disclosure is hereby incorporated by reference.

In some embodiments, the well plate has at least one hole penetrating the plate; a film covering the hole oriented normal to the film; and the hole having a diameter between 10 micrometers and two millimeters in at least one dimension parallel to the film at the location where the hole adjoins the film; and where the film is permanently attached to the plate; and the film has less than about 10%, about 9%, about 8%, about 7%, about 6%, about 5%, about 4%, about 3%, about 2%, or about 1% by weight of at least one of the elements selected from sulfur, phosphorus, and chlorine. In a particular embodiment, the film has less than about 4% by weight of at least one of the elements selected from sulfur, phosphorus, and chlorine.

In some embodiments, the well plate has at least one hole penetrating the well plate; the at least one hole passing through the well plate from one face to the other face, a film covering the hole, the film being at least 10%, at least 9%, at least 8%, at least 7%, at least 6%, at least 5%, at least 4%, at least 3%, at least 2%, or at least 1% translucent to 2,900 eV X-rays, 2,800 eV X-rays, 2,700 eV X-rays, 2,600 eV X-rays, 2,500 eV X-rays, 2,400 eV X-rays, 2,300 eV X-rays, 2,200 eV X-rays, 2,100 eV X-rays, 2,000 eV X-rays, 1,900 eV X-rays, 1,800 eV X-rays, or 1,700 eV X-rays oriented normal to the film, characterized in that the hole has a diameter less than 1,000 micrometers, less than 900 micrometers, less than 800 micrometers, less than 700 micrometers, less than 600 micrometers, less than 500 micrometers, less than 400 micrometers, less than 300 micrometers, less than 200 micrometers, or less than 100 micrometers in at least one dimension parallel to the film at the location where the hole adjoins the film and a cross sectional area of less than 0.010 square centimeters, less than 0.009 square centimeters, less than 0.008 square centimeters, less than 0.007 square centimeters, less than 0.006 square centimeters, less than 0.005 square centimeters, less than 0.004 square centimeters, less than 0.003 square centimeters, less than 0.002 square centimeters, or less than 0.001 square centimeters where the hole adjoins the film, and wherein the walls of the hole have an RMS roughness of less than 50 micrometers, less than 45 micrometers, less than 40 micrometers, less than 35 micrometers, less than 30 micrometers, less than 25 micrometers, less than 24 micrometers, less than 23 micrometers, less than 22 micrometers, less than 21 micrometers, less than 20 micrometers, less than 19 micrometers, less than 18 micrometers, less than 17 micrometers, less than 16 micrometers, or less than 15 micrometers. In a particular embodiment, the film covering the hole is at least 5% translucent to 2,300 eV X-rays oriented normal to the film, characterized in that the hole has a diameter less than 500 micrometers in at least one dimension parallel to the film at the location where the hole adjoins the film and a cross sectional area of less than 0.005 square centimeters where the hole adjoins the film, and wherein the walls of the hole have an RMS roughness of less than 20 micrometers.

In some embodiments, the sample holder is used to concentrate the sample to increase XRF signals. In some embodiments, the sample holder is preferably substantially free of at least one of the elements selected from sulfur, phosphorus, silicon, potassium, calcium, manganese, iron, cobalt, nickel, copper, zinc, arsenic, rhodium, molybdenum, chromium, selenium, bromine, silver, cadmium, platinum, gold, mercury, lead, gadolinium, dysprosium, terbium, europium, strontium, cesium, barium, and iodine. These elements are commonly present in samples to be measured, or X-rays derived from these elements are commonly present in measurements. Examples of suitable materials present in the sample holder include, but are not limited to, Porvair #229302, Porvair #229112, Porvair #229058, Porvair #229304, and Porvair #229301 (all of which are available from Porvair plc, Brampton House, 50 Bergen Way, King's Lynn, Norfolk PE30 2JG, U.K.); aluminum foils (examples: Microseal 'F' Foil from Bio-Rad Laboratories, 1000 Alfred Nobel Drive, Hercules, Calif. 94547); polyvinylidene difluoride, polyvinylidene fluoride, cellulose, filter paper, polystyrene, agarose, Super-Thin Polyester Surface-Protection Tape, Chemical-Resistant Surlyn Surface-Protection Tape, Abrasion-Resistant Polyurethane Surface-Protection Tape, Heat-Resistant Kapton Tape with Silicone Adhesive or with Acrylic Adhesive, UV-Resistant Polyethylene Surface-Protection Tape, Clean-Release Polyethylene Surface-Protection Tape, Low-Static Polyimide Tapeall (all available from McMaster-Carr, 6100 Fulton Industrial Blvd., Atlanta, Ga. 30336-2852); polypropylene (available from Lebow Company, 5960 Mandarin Ave., Goleta, Calif. 93117 U.S.A.); AP1, AP3, ProLINE Series 10, ProLINE Series 20, Dura-Beryllium substrates (from Moxtek, 452 West 1260 North, Orem, Utah 84057); Ultralene®, mylar, polycarbonate, prolene, and kapton (available from SPEX CertiPrep Ltd, 2 Dalston Gardens, Stanmore, Middlesex HA7 1BQ, England); Hostaphan®, polyester, and Etnom® (available from Chemplex Industries, Inc., 2820 SW 42nd Avenue, Palm City, Fla. 34990-5573 USA); Zone Free Film Part ZAF-PE-50 (available from Excel Scientific, 18350 George Blvd, Victorville, Calif., 92394); glass, and silicon. This list is not exhaustive, and other materials may be used as part of the sample holder.

In various embodiments, the sample holder comprises materials which are substantially free of elements which have XRF emission peaks having energies of between about 1.9 KeV and about 3 KeV, because these peaks tend to interfere with the signals of most interest to biochemical and biological applications. Elements which have XRF emission peaks having energies of between 1.9 KeV and 3 KeV include: osmium, yttrium, iridium, phosphorus, zirconium, platinum, gold, niobium, mercury, thallium, molybdenum, sulfur, lead, bismuth, technetium, ruthenium, chlorine, rhodium, palladium, argon, silver, and thorium. In some embodiments, if an XRF spectrometer is used which uses an X-ray detector which comprises silicon, then the sample holder may also be free of elements which have XRF escape peaks (i.e. XRF emission peaks minus 1.74 KeV) having energies of between about 1.9 KeV and about 3 KeV, because these escape peaks tend to interfere with the signals of most interest for biochemical and biological applications. Elements which have XRF escape peaks having energies of between 1.9 KeV and 3 KeV are: calcium, tellurium, iodine, scandium, xenon, cesium, barium, titanium, and lanthanum. As used herein, "substantially free" may be defined as being less than about 4% by weight. In some embodiments, the sample holder should be substantially free of the element or elements which are being used to quantify the sample. In some embodiments, the sample holder also comprises at least one element that is not present in the sample at concentrations above one weight percent in any pixel of the sample.

In various embodiments, an apparatus for preparing samples (i.e., a sample comprising the soluble target and the insoluble material) for XRF analysis in multi-well plate is provided. In some embodiments, the apparatus comprises a multi-well plate having one or more holes passing through the plate. In some embodiments, the holes are covered on one side of the plate by a detachable cover forming a water-tight seal against the plate. In some embodiments, the cover is substantially free of the elements osmium, yttrium, iridium, phosphorus, zirconium, platinum, gold, niobium, mercury, thallium, molybdenum, sulfur, lead, bismuth, technetium, ruthenium, chlorine, rhodium, palladium, argon, silver, and thorium. In some embodiments, the holes are less than about 500 micrometers across in one dimension where the cover covers the holes. In an illustrative embodiment, the holes are covered by a film on one side of the plate. In an illustrative embodiment, the holes are less than 500 micrometers across in one dimension where the film covers the holes. In some embodiments, the cover or the film is translucent to x-rays emitted by the elements being measured.

In various embodiments, the methods of the invention comprise the step of removing the first solution comprising unbound soluble targets while retaining the insoluble material comprising bound soluble targets. In some embodiments, the first solution may be removed by methods known in the art such as, without limitation, centrifugation, aspiration, decanting, and pipetting. In an embodiment, the first solution is removed by filtration. In an illustrative embodiment, the first solution is removed using a multi-well filter plate comprising a chemically inert filter with a pore size selected to retain the insoluble material. In some embodiments, the solution that is removed is also retained for analysis.

In various embodiments, methods of the invention may be expedited using a centrifuge (e.g., the IEC CL40 available from Thermo Fisher Scientific, product #11210923, 450 Fortune Blvd, Milford, Mass., 01757) or a vacuum manifold (e.g., a Vacuum apparatus such as the MultiScreen Vacuum manifold with Direct Stack from Millipore, 290 Concord Road, Billerica, Mass. 01821), which is attached to a standard vacuum pump.

In various embodiments, the methods of the invention comprise the step of resuspending the insoluble material comprising the bound soluble target in a second solution thereby resulting in a resuspension solution. In some embodiments, the second solution comprises at least one non-volatile component. In some embodiments, the non-volatile component is liquid at room temperature when dehydrated. In some embodiments, the insoluble material is present in the resuspension solution at a concentration of about 0.1% to about 10% (v/v). For example, the insoluble material may be present in the resuspension solution at a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% (v/v).

In some embodiments, the mechanical agitation is utilized to maintain the insoluble material in suspension. In some embodiments, the mechanical agitation is provided by, for example, an incubator shaker, vortexer, rotator, rocker plate, or the like.

In some embodiments, the resuspension solution is dried resulting in a preparation of non-volatile solute. In some embodiments, the final volume of non-volatile solute following drying is between about 0.05 µl and 5.0 µl. For example, the final volume of non-volatile solute following drying may be about 0.05 µl, 0.06 µl, 0.07 µl, 0.08 µl, 0.09 µl, 0.1 p1, 0.2 µl, 0.3 µl, 0.4 µl, 0.5 µl, 0.6 µl, 0.7 µl, 0.8 µl, 0.9 µl, 1 µl, 2 µl, 3 µl, 4 µl, or 5 µl. In various embodiments, the drying of the insoluble material is conducted in a multi-well plate.

In various embodiments, the method of the invention is directed to an analysis of the binding between a soluble target and an insoluble material. In some embodiments, the measured binding affinity depends on the chemical environment and temperature. In some embodiments, the binding affinity does not change when the chemical environment does not change. In some embodiments, the external factors may have an effect on the measured binding affinity.

In some embodiments, the free energy of binding of a soluble target and an insoluble material is represented by the following equation:

$$\Delta G = \Delta H - T\Delta S$$

where $\Delta G$ is the change in the Gibbs free energy of the binding reaction, $\Delta H$ is the change in enthalpy of the binding reaction, T is the temperature, and $\Delta S$ is the change in entropy of the binding reaction (see, for example: Gordon M. Barrow, Physical Chemistry, 5th Ed., McGraw-Hill, N.Y., 1988, Chapter 7). The temperature should be constant to avoid changing the $T\Delta S$ term, because changes to the $T\Delta S$ term would introduce temperature derived artifacts into the measurements. $\Delta G$ will also be affected by, for example, the presence of modulators that modulate binding between the soluble target and the insoluble material. In some embodiments, the chemical environment for the soluble target and the insoluble material is not changed. In some embodiments, the temperature is not varied between measurements and all measurements is taken at substantially the same temperature, i.e. within +3° C., such as within ±1° C.

In various embodiments, the present methods may be utilized for measuring the amount of soluble target present in the sample of insoluble material using XRF.

The present methods provide the advantage of being amenable to high-throughput and/or multiplexing formats. In various embodiments, the present methods allow for multiplexing in which multiple varying conditions, for example, multiple concentrations, multiple targets, or multiple insoluble materials, may be tested in parallel. For example, in some embodiments, the methods of the invention may be carried out to perform multiple measurements in parallel that vary either the identity or amount of the insoluble material. In some embodiments, the methods of the invention may be carried out to perform multiple measurements in parallel that vary either the identity or concentration of the soluble target. In some embodiments, the methods of the invention may be carried out to perform multiple measurements in parallel that vary either the identity or concentration of a soluble modulator that modules the binding of the soluble target to the insoluble material.

In various embodiments, the methods of the invention allow for various applications due to its high-throughput and multiplexing nature.

In some embodiments, the present methods of may be utilized to measure the binding affinity between a soluble target and the insoluble material. In some embodiments, the present methods comprise using multiple parallel reactions which differ with respect to the concentration of the soluble target so as to measure concentration-dependent binding.

In some embodiments, the methods of the invention may be utilized for identifying novel interactions by screening different combinations of soluble targets and insoluble test materials. In some embodiments, the methods comprise using multiple parallel reactions that differ with respect to the identity of the soluble target so as to assess the ability of different soluble targets to bind a single insoluble material. In some embodiments, the methods comprise using multiple parallel reactions that differ with respect to the identity of the insoluble material so as to assess the ability of different insoluble test materials to bind a single soluble target. In some embodiments, the methods comprise using multiple parallel reactions that differ with respect to the concentration or identity of a modulating compound so as to measure the ability of one or more modulating compounds to modulate the binding between a soluble target and an insoluble material.

Figure 2:
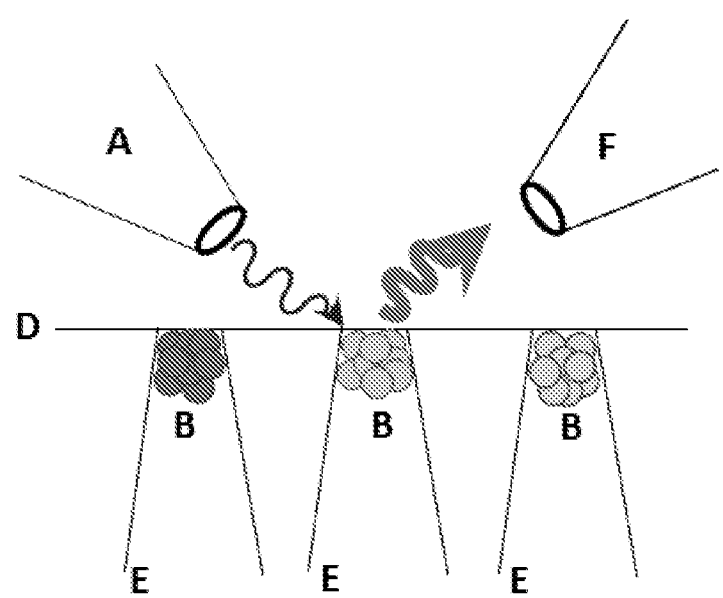
FIG. 2 provides an illustration of a measurement of multiple insoluble materials by XRF. As shown, a focusing optic is represented as (A), insoluble materials are represented as (B), an X-ray transparent bottom is represented as (D), a well plate is represented as (E), and an X-ray detector is represented as (F).

An illustrative analysis of multiple insoluble materials by XRF is provided in FIG. 2. As shown, a focusing optic is represented as (A), insoluble materials are represented as (B), an X-ray transparent bottom is represented as (D), a well plate is represented as (E), and an X-ray detector is represented as (F).

In various embodiments, the methods of the invention may be utilized for biological assays. In some embodiments, the methods may comprise using non-adherent biological cells as the insoluble material. In some embodiments, the methods comprise measuring the binding and/or internalization of a soluble target in the cell material. In some embodiments, the methods comprise using multiple parallel reactions that differ with respect to the concentration or identity of a modulator compound to measure the ability of one or more modulator compounds to alter binding between the soluble target and the biological cell. In some embodiments, the methods comprise using multiple parallel reactions that differ with respect to the biological cells to measure the ability of multiple cell types to interact with a single soluble target.

In an illustrative embodiment, methods of the invention are used to measure the binding of soluble metal ions to chelator molecules.

Illustrative metal elements are as follows: 3: Lithium, 4: Beryllium, 11: Sodium, 12: Magnesium, 13: Aluminum, 19: Potassium, 20: Calcium, 21: Scandium, 22: Titanium, 23: Vanadium, 24: Chromium, 25: Manganese, 26: Iron, 27: Cobalt, 28: Nickel, 29: Copper, 30: Zinc, 31: Gallium, 37: Rubidium, 38: Strontium, 39: Yttrium, 40: Zirconium, 41: Niobium, 42: Molybdenum, 43: Technetium, 44: Ruthenium, 45: Rhodium, 46: Palladium, 47: Silver, 48: Cadmium, 49: Indium, 50: Tin, 55: Cesium, 56: Barium, 57: Lanthanum, 58: Cerium, 59: Praseodymium, 60: Neodymium, 61: Promethium, 62: Samarium, 63: Europium, 64: Gadolinium, 65: Terbium, 66: Dysprosium, 67: Holmium, 68: Erbium, 69: Thulium, 70: Ytterbium, 71: Lutetium, 72: Hafnium, 73: Tantalum, 74: Tungsten, 75: Rhenium, 76: Osmium, 77: Iridium, 78: Platinum, 79: Gold, 80: Mercury, 81: Thallium, 82: Lead, 83: Bismuth, 87: Francium, 88: Radium, 89: Actinium, 90: Thorium, 91: Protactinium, 92: Uranium, 93: Neptunium, 94: Plutonium, 95: Americium, 96: Curium, 97: Berkelium, 98: Californium, 99: Einsteinium, 100: Fermium, 101: Mendelevium, 102: Nobelium, 103: Lawrencium, 104: Rutherfordium, 105: Dubnium, 106: Seaborgium, 107: Bohrium, 108: Hassium, 109: Meitnerium, 110: Darmstadtium, 111: Roentgenium, 112: Copernicium, 113: Ununtrium, 114: Flerovium, 115: Ununpentium, and 116: Livermorium.

In another illustrative embodiment, methods of the invention are used to characterize metal accumulation in biological cells, such as non-adherent cells.

The present invention finds use, in some embodiments, in environmental detection and protection. For instance, the present invention may be used to assess metal contamination (in soil and/or groundwater (e.g. at current or abandoned industrial sites). In some embodiments, the invention relates to environmental cleanup and remediation, e.g. the treatment of brownfield land. The present invention finds use, in some embodiments, in detection of metal and/or concentrations in wastewater. The present invention finds use, in some embodiments, in detection of metal concentrations in wastewater near power plants and industrial sources.

The present invention finds use, in some embodiments, in monitoring human consumption of metal elements. For instance, the present invention, in various embodiments, relates to analysis of drinking water. For instance, the present invention, in various embodiments, relates to analysis of the potability of water. In other embodiments, the present invention allows for measuring metal elements in food or soil (e.g. of agricultural spaces).

Further, and relatedly, the present invention, in various embodiments, relates to analysis, e.g. quality monitoring, of one or more of environmental water, ground water, surface water, and wastewater.

The present invention finds use, in some embodiments, in the analysis of a biological fluid. The biological fluids can be, or be formulated to simulate, the fluids extracted or produced from plants, animals, humans, yeast and/or bacteria. Such fluids can be naturally sourced or are simulated (e.g., including using naturally source ingredients and/or unnaturally sourced ingredients). For example, such fluids can include blood plasma, synovial fluid, urine, gastric fluid (e.g., fasted-state gastric fluid or fed-state gastric fluid), intestinal fluid, (e.g., fasted-state intestinal fluid, fed-state intestinal fluid) colonic fluid, fasted-state colonic fluid, fed-sate colonic fluid, saliva, lung fluid, fluid from exhaled breath, vaginal fluid, semen, tears, sweat, cerebrospinal fluids, cerumen, endolymph, perilymph, feces, milk, bronchial fluids, amniotic fluid, aqueous humor, vitreous humor, bile, chyle, chyme, exudate, intracellular fluid, interstitial fluid, lymphatic fluid, transcellular fluid, plant exudates, female ejaculate, gastric acid, gastric juice, mucus, pericardial fluid, pleural fluid, pus, rheum, sebum, sputum, vomit, and mixtures of these. Such fluids can be derived from an animal, e.g. human, believed to have been exposed a soluble target. Such fluids can include many compounds and can be undefined or uncharacterized.

XRF System

In various embodiments, the present invention provides methods of detecting the binding of a soluble target to an insoluble material using XRF analysis.

XRF spectroscopy can be a useful method for the implementation of some of the embodiments herein described. XRF spectrometry is a spectroscopic technique that can be used to determine one or more chemical elements (e.g., heavy metals) that are present in a sample, such as can be present in an analyte, a molecule, a polymer, a mineral, an organelle, a tissue, a biological fluid, an organ, an inorganic materials (e.g., clays, sands, silt, rocks and low organic containing soils), organic material (e.g., biomass such as plants, animals, insects, yeast, bacterial and/or high organic containing soil) or other substrates. The method can be used to qualitatively identify and also quantify the elements present and relies on the underlying physical principle that when an atom of a particular element is irradiated with x-ray radiation, the atom ejects a core electron such as a K, L or M shell electron. The resulting atom is in an excited state, such as a $1S^1$ excited state, and it can return to the ground state by replacing the ejected electron with an electron from a higher energy orbital. This transition is accompanied by the emission of a photon, in the process known as XRF, and the photon energy is equal to the difference in the energies of the two orbitals. Each element has a characteristic set of orbital energies and therefore, a characteristic XRF spectrum. For example, each element will have a characteristic x-ray energy signal corresponding to the energies of the K, L and M electron shells of each element.

XRF can be generated by excitation of atoms by a beam of electrons, particles and/or x-rays. Samples, such as described herein, subjected to such excitation can produce XRF due to the elements in the samples and one or more of the elements can be monitored. For example, Particle-Induced X-ray Emission (PIXE) and XRF can be used. In some embodiments, XRF is used in the embodiments described herein. In embodiments, p-XRF is used.

In some embodiments, the XRF is energy dispersive XRF. Optionally, the XRF utilizes polychromatic x-rays for exciting the sample. In some embodiments the analysis method is an XRF that utilizes a micro-focus x-ray tube. Optionally, the XRF utilizes a focusing optic.

In energy dispersive XRF, the characteristic radiation of a particular line can be described approximately as a Gaussian function (e.g., a detector response function). The spectral background results from a variety of processes such as incoherent scattered primary radiation and therefore depends on the shape of the excitation spectrum and on the sample composition. In embodiments, the characteristic signal of an analyte (e.g., element) of interest such as a heavy metal produces a signal in at least one area of the spectrum such as a peak with a signal to noise ratio of at least 3. One method to obtain the net data area under a line of interest consists of interpolating the background under the peak and summing the background-corrected channel contents in a window over the peak. This approach can be limited by the curvature of the background and by the presence of other peaks and other peak deconvolution methods can be used to better resolve the spectrum. A resolved peak is understood that the peak energy (e.g., position) and counts under a peak (e.g., integrated area) can be determined and associated to a particular element.

A widely used method for peak resolution (e.g., deconvolution) is non-linear least squares fitting of the spectral data with an analytical function. This algebraic function, including all important parameters (e.g., net areas of the fluorescent lines, their energy and resolution) is used as a model for the measured spectrum. It consists of the contribution from all peaks (e.g., modified Gaussian peaks with corrections for low-energy tailing and escape peaks) within a certain region of interest and the background (e.g., described by, for example, linear or exponential polynomials). The optimum values of the parameters are those for which the difference between the model and the measured spectrum is minimal. Some of the parameters are nonlinear, and a minimization procedure is selected such as the Marquardt algorithm.

Another method for peak resolution applies a top-hat filter to suppress low frequency components in the spectrum. This method reduces or even eliminates the background but also can distort the spectrum. In the method, the top hat filter is applied to a well-defined reference spectrum (e.g., of known concentrations of elements) as well as the experimental spectrum with unknowns and the two are compared. The comparison can be, for example, by applying a multiple linear least-squares fitting to the filtered spectra resulting in the net peak areas of interest.

Other deconvolution protocols can be used to resolve the peaks of interest. Backgrounds can vary between about zero counts per second (cps) and about 10,000 cps dependent at least in part on the deconvolution protocol used. It is to be understood by those skilled in the art what protocol can be utilized.

Further methods involving XRF are described in U.S. Pat. Nos. 7,858,385; 7,519,145; 7,929,662, and 9,063,066 and U.S. Patent Publication No. 2008-0220441, the entire contents of which are incorporated herein.

In various embodiments, the XFR analysis is performed using an XRF spectrometer. An XRF spectrometer is an apparatus capable of irradiating a sample (e.g., a sample comprising a soluble targeting and an insoluble material) with an X-ray beam, detecting the XRF from the sample, and using the XRF to determine the presence of elements in the sample and measuring the quantity of the elements. The irradiation can be produced by various sources, such as synchrotron radiation, a radioactive source or an x-ray tube. Synchrotron radiation can produce a monochromatic x-ray beam with a very high intensity. The bending, beam focusing and particle acceleration needed to produce synchrotron radiation requires a larger scale facility with concomitant expenses. Regarding radioactive sources, x-rays from radioactive primary sources such as $^{55}$Fe, $^{109}$Cd and $^{241}$Am can be made to strike a secondary exciter target, e.g., tin, and the characteristic x-rays from the exciter target are aimed at the unknown sample. Radioactive sources produce beams with the characteristic lines of the secondary exciter target and have very low energies elsewhere. X-ray tubes produce polychromatic x-rays including a very broad "Bremsstrahlung" radiation band and characteristic emission peaks. X-ray tubes offer analytical flexibility in the beam energies, for example by changing the applied voltage and target material of the x-ray tube. Filters can also be added to narrow or exclude certain energies (e.g., high pass, low pass or band pass filters). Focusing optics can be used such as collimators and/or concentrators (e.g., mono capillary and polycapillary) to produce spot sizes smaller than a millimeter in diameter. The fluorescence can be detected in at least two ways, using wavelength dispersive or energy dispersive methods. Wavelength dispersive detectors work by reflecting sample radiation onto an analyzing crystal and measurement of the angle of reflection followed by calculation of the wavelength using Bragg's Law. Energy dispersive detectors work by generating a signal that is proportional to the absorbed energy of a single photon. For example, solid state detectors include gas filled detectors and semiconductor detectors (e.g., PIN diode, silicon drift detectors, Si(Li), SI PIN detector, silicon drift detector, SiLi detector, CdTe, Diamond, Germanium detectors, ion chamber detectors, and the like). The angle of excitation and detector can be between about 0 and about 180 deg. For example, angles can be between about 5 DEG and about 95 DEG such as for XRF and μ-XRF. In some instances very low angles, such as below 0.5 DEG can be used, such as when using Total Reflection X-ray Fluorescence (TXRF) and grazing emission XRF. The above methods and components can be utilized to detect XRF in the samples described herein, including using modified commercial equipment. In some embodiments, the methods use at least one x-ray tube (e.g., having Cu, Mo, Cr, W or Rh targets), polycapillary focusing optics and one or more solid state detectors (e.g., one or two detectors). For example, polychromatic x-rays generated from an x-ray tube can be focused to less than 5 mm diameter (e.g., less that about 4 mm diameter, less than about 3 mm diameter, less than about 2 mm diameter, less than about 1 mm diameter, less than about 750 μm diameter, less than about 500 μm diameter, less than about 100 μm diameter or even less than about 50 μm diameter) spot size and detected using a silicon drift detector.

An example of an XRF spectrometer which may be used with the present invention includes, but is not limited to, the EDAX Eagle XPL energy dispersive XRF spectrometer, equipped with a microfocus X-ray tube, lithium drifted silicon solid-state detector, a sample stage, processing electronics, and vendor supplied operating software, available from the EDAX division of Ametek, 91 McKee Drive Mahwah, N.J. 07430. Another example of an XRF spectrometer which may be used with the present invention includes, but is not limited to, the ZSX Primus, available from Rigaku Americas, 9009 New Trails Drive, The Woodlands, Tex. 77381.

In some embodiments, the XRF instrument comprises at least one of the following: a monocapillary focusing optic, a polycapillary focusing optic, a doubly curved crystal focusing optic, a collimator, a microfocus X-ray tube, a synchrotron X-ray source, a linear accelerator X-ray source, a rhodium X-ray tube, a molybdenum X-ray tube, a chromium X-ray tube, a silver X-ray tube, a palladium X-ray tube, a monochromatic X-ray source, a polychromatic X-ray source, a polarized X-ray source, a confocal XRF spectrometer focusing arrangement, a PIN diode detector, a semiconductor X-ray detector, a germanium or doped germanium X-ray detector, a silicon or doped silicon X-ray detector, a wavelength dispersive XRF spectrometer, an energy dispersive XRF spectrometer, and total reflectance XRF spectrometer.

In some embodiments, the X-ray excitation source emits X-ray having a polychromatic X-ray excitation spectrum. In some embodiments, the X-ray excitation source emits X-rays having a spectrum with at least two maxima. Excitation with polychromatic X-rays increases the efficiency for exciting more than one chemical element in the sample (e.g., a sample comprising a soluble targeting and an insoluble material) being analyzed, or for exciting more than one spectral feature in the chemical analyte being analyzed.

In some embodiments, the XRF spectrometer comprises an X-ray tube. In some embodiments, the X-ray tube consumes less than about 20 kilowatts of power, or less than about 15 kilowatts of power, or less than about 10 kilowatts of power, or less than about 5 kilowatts of power, or less than about 1 kilowatt of power. In some embodiments, the X-ray tube consumes less than about 500 watts of power. The significance of these power levels is that benchtop equipment may be conveniently shielded against X-ray leakage when the X-ray tube has these power levels.

Many x-ray sources will function with the present invention. In some embodiments, a rhodium or molybdenum x-ray source is employed. In some embodiments, a chromium, palladium or silver x-ray source is used. In various embodiments, the x-ray tube has a characteristic K-alpha or L-alpha line at or above about 2.838 KeV and less than about 9.441 KeV. X-ray M lines are frequently broad and less efficient. In some embodiments, the x-ray source does not have an M line above 2.120 KeV. X-rays that impinge on the sample may be generated by x-ray tubes directly or indirectly by the excitation of a target by x-rays.

In various embodiments, excitation photons used with the present invention should have energies of at least 300 eV. In various embodiments, the excited atoms should have a fluorescence half-life of 10 ns or less. The importance of having such a short fluorescence lifetime is related to the "dead time", which is a period of time after the XRF is measured. No additional XRF can be measured during the dead time. In some embodiments, the fluorescence lifetime of the type of atom being measured should be less than the dead time of the detector. In some embodiments, the fluorescence being measured has a fluorescence half-life of 10 nanoseconds (ns) or less. In some embodiments, the fluorescence being measured has a half-life of 100 picoseconds (ps) or less.

In some embodiments, the XRF spectrometer comprises one or more filters disposed between the X-ray excitation source and the sample (e.g., a sample comprising a soluble targeting and an insoluble material). The filter or filters serve to attenuate the different energy X-rays in the X-ray excitation beam to different degrees. Filters are useful because they can reduce unwanted X-ray signals from the sample, which often has the effect of dramatically speeding up the XRF analysis. In some embodiments, filters are used to decrease the dead time of the XRF detector. In some embodiments, the dead time is less than about 66%, less than about 50%, less than about 40%, less than about 30%, less than about 20%, less than 10%, less than about 5%, or less than about 1%. In some embodiments, the deadtime is between about 0.5% and about 50%. Examples of filters include, but are not limited to, aluminum, titanium, iron, cellulose, chromium, nickel and rhodium. In some embodiments, the filters have a thickness of between about 2 microns and about 1000 microns.

In some embodiments, the XRF analysis is performed on multiple spatial points on the sample. In such embodiments, the XRF analysis may be performed at a rate of at least one pixel per five seconds. In some embodiments, the X-ray excitation beam preferably has a spatial cross section of less than about 500 microns, less than about 400 microns, less than about 300 microns, less than about 200 microns, or less than 100 microns, for X-rays having an energy of 5,000 electron volts at the point at which the excitation beam impinges on the sample. In XRF microscopy, the most efficient (strongest signal with lowest noise) X-ray beam size, ceteris paribus, is one that is essentially matched to the sample size. This situation has not arisen previously because the samples used in the past have been larger than the beam size, so many systems use a small beam size and rastering or scanning across the sample. Also, many samples are not homogenous, so having a beam size matched to the sample size has not previously made much sense. For the samples analyzed and/or measured (e.g., a sample comprising a soluble targeting and an insoluble material), the samples are generally circular and tend to have diameters between 40 μm and 2 mm (i.e., areas of about between 1 square nanometer and 3 square microns). These samples are also homogenous or otherwise have no need to be sampled in subregions. In such cases, matching the beam size to the spot size provides the strongest signal to noise ratio. Thus, in some embodiments, a preferred XRF source for measuring a sample comprises an X-ray source, where the transmitted X-ray beam has a cross-sectional area essentially the same surface area as the sample. "Matching" would preferentially be as close a match as practical, but "mismatching," for example an imperfect match where the beam has a cross-sectional area of between 25% and 250% of the surface area of the sample, is also acceptable. This area matching and/or mismatching may be accomplished in rare cases by having an X-ray source whose transmitted beam cross-sectional area matches the sample area without any modification of the beam. More typically, the beam size will have to be modified to match the sample size. Modification is typically carried out by means of focusing optics or by a collimator. Thus, the source further comprises a focusing means or collimator disposed between the source and the sample.

In some embodiments, the sample (e.g., a sample comprising a soluble targeting and an insoluble material) is measured using XRF spectrometry at multiple emission wavelengths, which allows multiple elements to be measured simultaneously. In some embodiments, the XRF spectrometer performs XRF spectrometry, which is used to identify chemical elements by the energy or energies of signals in the XRF spectrogram. In such embodiments, XRF spectrometry may be used to quantify chemical elements by the amplitude of the signals, also referred to as peaks, in the XRF spectrogram. The area under the peaks is proportional to the quantity of the element that produces that peak, corrected for the sensitivity for that element for the XRF spectrometer being used. The area under each peak is typically derived from counting the x-rays fluoresced or scattered from the sample having energies associated with the element being measured. In some embodiments, the XRF spectrometer presents the quantity of each element measured as a spreadsheet or database with numerical data. In some embodiments, the XRF spectrometer is calibrated so that the amount of an element that produces a peak may be correlated to the area under that peak. In some embodiments, it is not necessary to generate a spectrogram and measure the area under each peak. In some embodiments, X-rays may also be measured as a count rate, typically counts of x-rays having the appropriate energies per second. In some embodiments, the amount of x-rays at appropriate energies may also be counted. Mathematical manipulations of the data are typically performed, for example to remove background and noise and to allow statistics to be determined and to allow algorithms to be used for diagnostic, prognostic, response, and/or health status biomarkers. For example, means, ratios, and/or principal component analysis may be used to differentiate signals and noise and background.

In some embodiments, the sample (e.g., a sample comprising a soluble targeting and an insoluble material) is analyzed by XRF mapping. In some embodiments, the mapping comprises obtaining multiple XRF measurements of one or more elements, at multiple locations on the sample. In some embodiments, the sample may be mapped while it is oriented in at least two different angles relative to the X-ray excitation beam. The angle at which the sample is oriented to the X-ray beam may be conveniently adjusted, for example, by tilting the stage or placing a shim underneath the sample or sample holder, or using a sample mount capable of rotating in one or more axes. If the sample is measured in this manner, the XRF data may be displayed to appear three dimensional, for example, by projecting the images from each location in a different color or with imaged displayed with different polarizations. The image may then viewed with glasses having different polarized lenses, different colored lenses, as cross-eye or wall-eye stereo image pairs, or using other standard three dimensional imaging techniques. The image may also be reconstructed using computer tomography to construct a three dimensional image or a tomogram.

In various embodiments, additional instruments that may be utilized for the present invention include, but are not limited to inductively coupled plasma mass spectrometry (ICP-MS) and Flame Atomic Absorption Spectrometry.

The following EXAMPLES provide an illustration of various aspects of this invention.

EXAMPLES

Example 1. Analysis of Cesium Binding to Peptide Chelators on Solid Support

Figure 3:
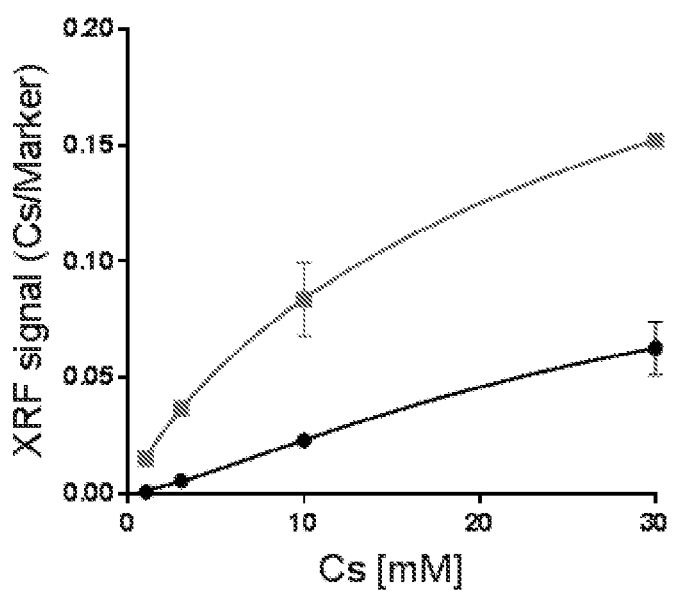
FIG. 3 shows application of the method of the invention for measuring cesium ($Cs^+$) binding to solid-supported peptide chelators. Example data are shown using the method of the invention to measure the binding of $Cs^+$, a monovalent ion, to two insoluble materials that comprise chelator compounds.

Methods of the invention were used to measure the binding of cesium ($Cs^+$), a monovalent ion, to two insoluble materials that comprise chelator compounds. In this example, $Cs^+$ was the soluble chemical, and the chelator compounds were peptides covalently attached to synthesis resins (insoluble beads) with an approximate diameter of 60 μm. The beads were exposed to $Cs^+$ solution in a 96-well plate format. Excess solution was removed via vacuum filtration using a 384-well filter plate. Beads were resuspended in a solution containing 1% glycerol, transferred to a well plate and dried. XRF signals for $Cs^+$ and a marker element included in the target peptide were measured using XRF as shown in FIG. 3. Data were fit to a binding isotherm to determine $K_D$ values. Altogether, the data demonstrate that methods of the invention effectively measured binding of a soluble chemical (i.e., $Cs^+$) to an insoluble material (i.e., chelator compounds).

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

---

What is claimed is:

1. A method for measuring binding of a soluble target to an insoluble material comprising:
   exposing a solution comprising the soluble target to the insoluble material thereby allowing the formation of a complex comprising the soluble target and the insoluble material;
   removing the solution comprising unbound soluble target and retaining the insoluble material;
   resuspending the insoluble material in a second solution comprising at least one non-volatile component;
   drying the insoluble material in a well plate; and
   measuring the X-ray fluorescence (XRF) of the soluble target bound to the dried insoluble material within the well plate.

2. The method of claim 1, wherein the soluble target comprises at least one chemical element with an atomic number greater than 9.

3. The method of claim 1, wherein the soluble target is selected from an inorganic ion or inorganic compound, an organic ion or organic compound, and a biological molecule.

4. The method of claim 3, wherein the soluble target is a metal ion.

5. The method of claim 1, wherein the insoluble material comprises a particle.

6. The method of claim 5, wherein the particle has an average diameter between about 1 μm and 500 μm.

7. The method of claim 1, wherein the insoluble material is selected from a chelator, a biological molecule such as a peptide, modified peptide, peptoid, protein, nucleic acid, oligonucleotide, liposome, micelle, and proteoliposome.

8. The method of claim 1, wherein the insoluble material is a cell.

9. The method of claim 1, wherein the insoluble material comprises at least one chemical element with an atomic number greater than 9.

10. The method of claim 1, wherein volume of insoluble material used is between about 0.1 μl and about 2 μL.

11. The method of claim 1, wherein the removing is carried out by centrifugation, aspiration, decanting, pipetting, and/or filtrating.

12. The method of claim 1, wherein the well plate is a 96, 384, or 1536 multiwell plate.

13. The method of claim 1, wherein the well plate comprises a film or a surface that is largely transparent to X-rays.

14. The method of claim 1, wherein multiple soluble targets are tested.

15. The method of claim 1, wherein multiple concentrations of a single soluble target are tested.

16. The method of claim 1, wherein multiple insoluble materials are tested.

17. The method of claim 1, wherein multiple concentrations of a single insoluble material are tested.

18. The method of claim 1, wherein solution further comprises a modulator that modulates the binding between the soluble target and the insoluble material.

19. The method of claim 18, wherein multiple modulators are tested.

20. The method of claim 18, wherein multiple concentrations of a single modulator are tested.

21. The method of claim 1, wherein the method is utilized to measure the binding affinity of the soluble target and the insoluble material.

22. The method of claim 1, wherein the method is utilized to characterize the binding between different combinations of soluble targets and insoluble materials.

23. The method of claim 1, wherein the method is utilized to characterize the binding of a soluble metal ion to a chelator.

24. The method of claim 1, wherein the method is utilized to characterize the binding of a soluble target to a cell.

25. The method of claim 8, wherein the insoluble material is a non-adherent cell.

26. The method of claim 24, wherein the method is utilized to characterize the binding of a soluble target to a non-adherent cell.

* * * * *

UNITED STATES PATENT AND TRADEMARK OFFICE
CERTIFICATE OF CORRECTION

Page 1 of 1

| | |
|---|---|
| PATENT NO. | : 11,573,224 B2 |
| APPLICATION NO. | : 16/646736 |
| DATED | : February 7, 2023 |
| INVENTOR(S) | : Nathan H. Zahler |

It is certified that error appears in the above-identified patent and that said Letters Patent is hereby corrected as shown below:

In the Specification

Column 1, Line 11 (Approx.), add:
--STATEMENT REGARDING FEDERALLY SPONSORED R&D
This invention was made with government support under R43 A1091186 awarded by the National Institutes of Health. The government has certain rights in the invention.--.

Signed and Sealed this
Thirty-first Day of December, 2024

Derrick Brent
*Acting Director of the United States Patent and Trademark Office*